United States Patent
Holmes et al.

(10) Patent No.: US 9,120,761 B2
(45) Date of Patent: Sep. 1, 2015

(54) SELECTIVE FAK INHIBITORS

(75) Inventors: Ian Peter Holmes, Bundoora (AU);
Ylva Bergman, Parkville (AU); Gillian Elizabeth Lunniss, Parkville (AU);
Marica Nikac, Parkville (AU); Neil Chol, Parkville (AU); Catherine Fae Hemley, Parkville (AU); Scott Raymond Walker, Parkville (AU);
Richard Charles Foitzik, Parkville (AU); Danny Ganame, Bundoora (AU);
Romina Lessene, Bundoora (AU)

(73) Assignee: Cancer Therapeutics CRC PTY LTD, Bundoora (AU)

( * ) Notice: Subject to any disclaimer, the term of this patent is extended or adjusted under 35 U.S.C. 154(b) by 81 days.

(21) Appl. No.: 13/542,917

(22) Filed: Jul. 6, 2012

(65) Prior Publication Data
US 2013/0022594 A1  Jan. 24, 2013

Related U.S. Application Data

(63) Continuation-in-part of application No. PCT/GB2012/000176, filed on Feb. 17, 2012.

(60) Provisional application No. 61/443,773, filed on Feb. 17, 2011, provisional application No. 61/523,489, filed on Aug. 15, 2011, provisional application No. 61/579,729, filed on Dec. 23, 2011.

(51) Int. Cl.
*A61K 31/506* (2006.01)
*C07D 239/42* (2006.01)
*C07D 403/12* (2006.01)
*C07D 401/12* (2006.01)
*C07D 401/14* (2006.01)

(52) U.S. Cl.
CPC ............ *C07D 239/42* (2013.01); *C07D 401/12* (2013.01); *C07D 401/14* (2013.01); *C07D 403/12* (2013.01)

(58) Field of Classification Search
CPC .............................. C07D 401/12; C07D 403/12
USPC ............. 544/295, 330, 331, 332; 514/252.13, 514/252.18, 253.09, 253.13
See application file for complete search history.

(56) References Cited

U.S. PATENT DOCUMENTS

| 2005/0256125 A1 | 11/2005 | Kath et al. |
| 2005/0256144 A1 | 11/2005 | Kath et al. |
| 2005/0256145 A1 | 11/2005 | Kath et al. |
| 2010/0113475 A1 | 5/2010 | Adams et al. |

FOREIGN PATENT DOCUMENTS

| WO | WO 97/22596 A1 | 6/1997 |
| WO | WO 97/30035 A1 | 8/1997 |
| WO | WO 97/32856 A1 | 9/1997 |
| WO | WO 98/13354 A1 | 4/1998 |
| WO | WO 98/35985 A1 | 8/1998 |
| WO | WO 99/02166 A1 | 1/1999 |
| WO | WO 00/12485 A1 | 3/2000 |
| WO | WO 00/39101 A1 | 7/2000 |
| WO | WO 00/40529 A1 | 7/2000 |
| WO | WO 00/41669 A2 | 7/2000 |
| WO | WO 00/47212 A1 | 8/2000 |
| WO | WO 00/53595 A1 | 9/2000 |
| WO | WO 01/32651 A1 | 5/2001 |
| WO | WO 01/60814 A2 | 8/2001 |
| WO | WO 01/64653 A1 | 9/2001 |
| WO | WO 01/64655 A1 | 9/2001 |
| WO | WO 01/64656 A1 | 9/2001 |
| WO | WO 01/92224 A1 | 12/2001 |
| WO | WO 01/94341 A1 | 12/2001 |
| WO | WO 02/04434 A1 | 1/2002 |
| WO | WO 02/08213 A1 | 1/2002 |
| WO | WO 03/078404 A1 | 9/2003 |
| WO | WO 2004/056786 A2 | 7/2004 |
| WO | WO 2004/056807 A1 | 7/2004 |
| WO | WO 2004/080980 A1 | 9/2004 |
| WO | WO 2005/016894 A1 | 2/2005 |
| WO | WO 2005/023780 A1 | 3/2005 |
| WO | WO 2006/021454 A2 | 3/2006 |
| WO | WO 2006/021457 A2 | 3/2006 |

(Continued)

OTHER PUBLICATIONS

Bagi, C.M. et al., "Dual Focal Adhesion Kinase/Pyk2 Inhibitor Has Positive Effects on Bone Tumors", Cancer May 15, 2008, vol. 112, No. 10, pp. 2313-2321.
Abstracts/Bone 48, 2011, S54.
Bagi, C.M. et al., "Sunitinib and PF-562,271 (FAK/Pyk2 inhibitor) effectively block growth and recovery of human hepatocellular carcinoma in a rat xenograft model", Cancer Biology & Therapy, vol. 8, No. 9, pp. 856-865, May 1, 2009.
Ebos, J.M et al., "Tumor and Host—Mediated Pathways of Resistance and Disease Progression in Response to Antiangiogenic Therapy", Clinical Cancer Researh, 2009, vol. 15, pp. 5020-5025.

(Continued)

*Primary Examiner* — Brian McDowell
(74) *Attorney, Agent, or Firm* — W. David Wallace; Holland & Knight LLP

(57) ABSTRACT

A compound of the formula (I):

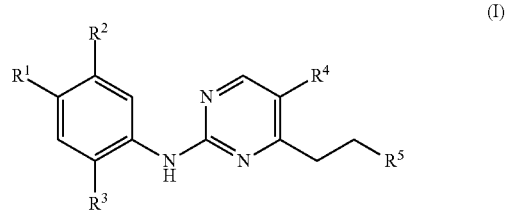

where $R^1$ or $R^2$ is a cyclc amine group and $R^5$ is an aromatic group with a carbonyl containing substituent for use as a FAK inhibitor.

22 Claims, 4 Drawing Sheets

(56) References Cited

FOREIGN PATENT DOCUMENTS

| | | |
|---|---|---|
| WO | WO 2006/076442 A2 | 7/2006 |
| WO | WO 2007/063384 A2 | 6/2007 |
| WO | WO 2007/140222 A2 | 12/2007 |
| WO | WO 2008/115369 A2 | 9/2008 |
| WO | WO 2008/115443 A1 | 9/2008 |
| WO | WO 2008/129380 A1 | 10/2008 |
| WO | WO 2009/024332 A1 | 2/2009 |
| WO | WO 2009/071535 A1 | 6/2009 |
| WO | WO 2009/105498 A1 | 8/2009 |
| WO | WO 2009/143389 A1 | 11/2009 |
| WO | WO 2009/153589 A1 | 12/2009 |
| WO | WO 2010/055117 A1 | 5/2010 |
| WO | WO 2010/058030 A1 | 5/2010 |
| WO | WO 2010/058032 A2 | 5/2010 |
| WO | WO 2010/106097 A1 | 9/2010 |
| WO | WO 2010/126922 A1 | 11/2010 |
| WO | WO 2010/136559 A1 | 12/2010 |
| WO | WO 2010/141406 A2 | 12/2010 |
| WO | WO 2010/141796 A2 | 12/2010 |
| WO | WO 2011/019943 A1 | 2/2011 |
| WO | WO 2011/039344 A1 | 4/2011 |
| WO | WO 2011/049332 A2 | 4/2011 |
| WO | WO 2012/006081 A1 | 1/2012 |
| WO | WO 2012/012139 A1 | 1/2012 |
| WO | WO 2012/022408 A1 | 2/2012 |
| WO | WO 2012/041796 A1 | 4/2012 |
| WO | WO 2012/045194 A1 | 4/2012 |
| WO | WO 2012/045195 A1 | 4/2012 |

OTHER PUBLICATIONS

Halder, J et al., "Therapeutic Efficacy of a Novel Focal Adhesion Kinase Inhibitor TAE226 in Ovarian Carcinoma", Cancer Research, Nov. 15, 2007, vol. 67, No. 22, pp. 10976-10983.
Nagashima, S. et al., "Identification of 4-benzylamino-2-[(4-morpholin-4-ylphenyl) amino] pyrimidine-5-carboxamide derivatives as potent and orally bioavailable STAT6 inhibitors", Bioorganic & Medicinal Chemistry, vol. 16, 2008, pp. 6509-6521.
Angelucci, A. et al., "Targeting Vascular Cell Migration as a Strategy for Blocking Angiogenesis: The Central Role of Focal Ashesion Protein Tyrosine Kinase Family", Current Pharmaceutical Design, 2007, vol. 13, pp. 2129-2145.
Benlimame, N. et al., "FAK signaling is critical for ErbB-2/ErbB-3 receptor cooperation for oncogenic transformation and invasion", The Journal of Cell Biology, Nov. 7, 2005, vol. 171, No. 3, pp. 505-516.
Bolos, V. et al., "The dual kinase complex FAK-Src as a promising therapeutic target in cancer", Onco Targets and Therapy, 2010, vol. 3, pp. 83-97.
Bouchard, V. et al., "β1 integrin/Fak/Src signaling in intestinal epithelial crypt cell survival: integration of complex regulatory mechanism", Apoptosis, 2008, vol. 13, pp. 531-542.
Brunton, V.G. et al., "Identification of Src-Specific Phosphorylation Site on Focal Adhesion Kinase: Dissection of the Role of Src SH2 and Catalystic Functions and Their Consequences for Tumor Cell Behavior", Cancer Research, Feb. 15, 2005, vol. 65, No. 4, pp. 1335-1342.
Chatzizacharias, N.A. et al., "Focal adhesion kinase: a promising target for anticancer therapy", Expert Opinion on Therapeutic Targets, 2007, vol. 11, No. 10, pp. 1315-1328.
Choi, H. et al., Design and synthesis of 7H-pyrrolo [2,3-d] pyrimidines as focal adhesion kinase inhibitors. Part 1, Bioorganic & Medicinal Chemistry Letters, vol. 16, 2006, pp. 2173-2176.
Choi, H. et al., Design and synthesis of 7H-pyrrolo [2,3-d] pyrimidines as focal adhesion kinase inhibitors. Part 2, Bioorganic & Medicinal Chemistry Letters, vol. 16, 2006, pp. 2689-2692.
Cohen, L.A. et al., "Mechanisms of Focal Adhesion Kinase Regulation", Current Cancer Drug Targets, 2005, vol. 5, pp. 629-643.
Contestabile, A. et al., "Localization of focal adhesion kinase isoforms in cells of the central nervous system", International Journal of Development Neuroscience, vol. 21, 2003, pp. 89-93.

Frisch, S.M, et al., "Control of Adhesion-dependent Cell Survival by Focal Adhesion Kinase", The Journal of Cell Biology, vol. 134, No. 3, Aug. 1996, pp. 793-799.
Golubovskaya, V.M. et al., "A Small Molecule Inhibitor, 1,2,4,5-Benzenetetraamine Tetrahydrochloride, Targeting the Y397 Site of Focal Adhesion Kinase Decreases Tumor", The Journal of Medicinal Chemistry, 2008, vol. 51, pp. 7405-7416.
Brunton, V.G. et al., "Src and focal adhesion kinase as therapeutic targets in cancer", Current Opinion in Pharmacology, 2008, vol. 8, pp. 427-432.
Burgaya, F. et al., "Alternatively Spliced Focal Adhesion Kinase in Rat Brain with Increased Autophosphorylation Activity",The Journal of Biological Chemistry, vol. 272, No. 45, Nov. 7, 1997, pp. 28720-28725.
Hirt, U. et al., AACR Poster, 2011, #A249.
Hu, X. et al., "Apigenin inhibited migration and invasion of human ovarian cancer A2780 cells through focal adhesion kinase", Carcinogenesis, vol. 29, No. 12, 2008, pp. 2369-2376.
Huanwen, W. et al., "Intrinsic chemoresistance to gemcitabine is associated with constitutive and laminin-induced phosphorylation of FAK in pancreatic cancer cell lines", Molecular Cancer, 2009, vol. 8, No. 125, pp. 1-16.
Llic, D. et al., "Reduced cell motility and enhanced focal adhesion contact formation in cells from FAK-deficient mice", Nature, vol. 377, Oct. 1995, pp. 539-544.
Lagares, D. et al., "Inhibition of Focal Adhesion Kinase Prevents Experimental Lung Fibrosis and Myofibroblast Information", Arthritis & Rheumatism, vol. 64, No. 5, May 2012, pp. 1653-1664.
Lahlou, H. et al., "Mammary epithelial-specific disruption of the focal adhesion kinase blocks mammary tumor progression", PNAS, vol. 104, No. 51, Dec. 18, 2007, pp. 20302-20307.
Liao, C. et al., "CSE I L/CAS, the cellular apoptosis susceptibility protein, enhances invasion and metastasis but not proliferation of cancer cells", Journal of Experimental & Clinical Cancer Research, 2008, vol. 27, No. 15, pp. 1-12.
Lietha, D. et al., "Structural Basis for the Autoinhibition of Focal Adhesion Kinase", Cell, vol. 129, Jun. 15, 2007, pp. 1177-1187.
Lietha, D. et al., "Crystal Structures of the FAK Kinase in Complex with TAE226 and Related Bis-Anilino Pyrimidine Inhibitors Reveal a Helical DFG Conformation", PLOS ONE, vol. 3, No. 11, Nov. 2008, pp. 1-7.
Long, W. et al., "SRC-3Δ4 Mediates the Interaction of EGFR with FAK to Promote Cell Migration", Molecular Cell , vol. 37, Feb. 12, 2010, pp. 321-332.
McLean, G.W. et al., "Decreased Focal Adhesion Kinase Suppresses Papilloma Formation during Experimental Mouse Skin Carcinogens", Cancer Research, vol. 61, Dec. 1, 2001, pp. 8385-8389.
Messina, S. et al., "Specific interactions of neuronal focal adhesion kinase isoforms with Src kinases and amphiphysin", Journal of Neurochemistry, vol. 84, 2003, pp. 253-265.
Mitra, S.K. et al., "Focal Adhesion Kinase: In Command and Control of Cell Motility", Nature Reviews Molecular Cell Biology, Jan. 2005, vol. 6, pp. 56-68.
Mitra, S.K. et al., "Intrinsic focal adhesion kinase activity controls orthotopic breast carcinoma metastasis via the regulation of urokinase plasminogen activator expression in a syngeneic tumor model", Oncogene, vol. 25, 2006, pp. 4429-4440.
Mitra, S.K. et al., "Intrinsic FAK activity and Y925 phosphorylation facilitate an angiogenic switch in tumors", Oncogene, vol. 25, 2006, pp. 5969-5984.
Richardson, A. et al., "A mechanism for regulation of the adhesion-associated protein tyrosine kinase pp125", Nature, vol. 380,Apr. 1996, pp. 538-540.
Yamamoto, D. et al., "FAK overexpression upregulates cyclin D3 and enhances cell proliferation via the PKC and PI3-kinase-Akt pathways", Cellular Signalling, vol. 15, 2003, pp. 575-583.
Zhao, X. et al., "Focal adhesion kinase and its signaling pathways in cell migration and angiogenesis", Advanced Drug Delivery Reviews, vol. 63, 2011, pp. 610-615.
Zificsak, C.A. et al., "Optimization of a novel kinase inhibitor scaffold for the dual inhibition of JAK2 and FAK kinases", Bioorganic & Medicinal Chemistry Letters, vol. 22, 2012, pp. 133-137.

(56) References Cited

OTHER PUBLICATIONS

Zouq, N.K. et al., "FAK engages multiple pathways to maintain survival of fibroblasts and epithelia-differential roles for paxillin and p130Cas", Journal of Cell Science, 2009, vol. 122, pp. 357-367.

Roberts, W.G. et al., "Antitumor Activity and Pharmacology of a Selective Focal Adhesion Kinase Inhibitor, PF-562,271", Cancer Research, Mar. 15, 2008, vol. 68, No. 6, pp. 1935-1944.

Schultze, A. et al., "Clinical Importance and Potential Use of Small Molecule Inhibitors of Focal Adhesion Kinase", Anti-Cancer Agents in Medicinal Chemistry, 2011, vol. 11, pp. 593-599.

Schultze, A. et al., "TAE226-mediated inhibition of focal adhesion kinase interferes with tumor angiogenesis and vasculogenesis", Invest New Drugs, 2010, vol. 28, pp. 825-833.

Schwock, J. et al., "Targeting focal adhesion kinase signaling in tumor growth and metastasis", Expert Opinion Therapy Targets, 2010, vol. 14, No. 1, pp. 77-94.

Shibue, T. et al., "Integrin β1-focal adhesion kinase signaling directs the proliferation of metastatic cancer cells disseminated in the lungs", PNAS Early Edition, 2009, pp. 1-6.

Sieg, D.J. et al., "FAK integrates growth-factor and integrin signals to promote cell migration", Nature Cell Biology, vol. 2, May 2000, pp. 249-257.

Siesser, P. et al., "The Signaling and Biological Implications of FAK Overexpression in Cancer", Clinical Cancer Research, Jun. 1, 2006, vol. 12, No. 11, pp. 3233-3237.

Slack-Davis, J.K. et al., "Cellular Characterization of a Novel Focal Adhesion Kinase Inhibitor", The Journal of Biological Chemistry vol. 282, No. 20, May 18, 2007, pp. 14845-14852.

Sood, A.K. et al., "Biological Significance of Focal Adhesion Kinase in Ovarian Cancer", American Journal of Pathology, vol. 165, No. 4, Oct. 2004, pp. 1087-1095.

Sun, H. et al., "Differences in CYP3A4 catalyzed bioactivation of 5-aminooxindole and 5-aminobenzsultam scaffolds in proline-rich tyrosine kinase 2 (PYK2) inhibitors: Retrospective analysis by CYP3A4 molecular docking, quantum chemical calculations and glutathione adduct detection using linear ion trap/orbitrap mass spectrometry", Bioorganic & Medicinal Letters, 2009, vol. 19, pp. 3177-3182.

Tanjoni, I. et al., "PND-1186 FAK inhibitor selectively promotes tumor cell apoptosis in three-dimensional environments", Cancer Biology & Therapy, May 15, 2010,vol. 9, No. 10, pp. 1-14.

Tomar, A. et al., "Focal adhesion kinase: switching between GAPs and GEFs in the regulation of cell mobility", Current Opinion in Cell Biology, 2009, vol. 21, pp. 676-683.

Hess, A.R. et al., "Focal Adhesion Kinase Promotes the Aggressive Melanoma Phenotype", Cancer Research, Nov. 1, 2005, vol. 65, No. 21, pp. 9851-9860.

Toutant, M. et al., Autophosphorylation of Tyr 397 and its phosphorylation by Src-family kinases are altered in focal-adhesion-kinase neuronal isoforms, Biochem J., 2000, vol. 348, pp. 119-128.

Van Nimwegen, M.J. et al., "Focal adhesion kinase: A potential target in cancer therapy", Biochemical Pharmacology, 2007, vol. 73, pp. 597-609.

Van Nimwegen, M.J. et al. "Requirement for Focal Adhesion Kinase in the Early Phase of Mammary Adenocarcinoma Lung Metastasis Formation", Cancer Research, Jun. 1, 2005, vol. 65, No. 11, pp. 4698-4706.

Villedieu, M. et al., "Acquisition of chemoresistance following discontinuous exposures to cisplatin is associated in ovarian carcinoma cells with progressive alteration of FAK, ERK and p38 activation in response to treatment", Gynecologic Oncology, 2006, vol. 101, pp. 507-519.

Walker, D.P. et al., "Trifluoromethylpyrimidine-based inhibitors of proline-rich tyrosine kinase 2 (PYK2): Structure-activity relationships and strategies for the elimination of reactive metabolite formation", Bioorganic & Medicinal Chemistry Letters, 2008, vol. 18, pp. 6071-6077.

Walsh, C. et al., "Oral delivery of PND-1186 FAK inhibitor decreases tumor growth and spontaneous breast to lung metastasis in pre-clinical models", Cancer Biology Therapy, May 15, 2010, vol. 9, No. 10, pp. 1-13.

Berge, S.M. et al., "Pharmaceutical Salts", Journal of Pharmaceutical Sciences, Jan. 1977, vol. 66, No. 1, pp. 1-10.

Cary, L.A. et al., "Stimulation of cell migration by overexpression of focal adhesion kinase and its association with Src and Fyn", Journal of Cell Science, 1996, vol. 109, pp. 1787-1794.

De Heer, p. et al., "Combined expression of the non-receptor protein tyrosine kinases FAK and Src in primary colorectal cancer is associated with tumor recurrence and metastasis formation", EJSO, 2008, vol. 34, pp. 1253-1261.

Gilmore, A.P. et al., "Inhibition of Focal Adhesion Kinase (FAK) Signaling in Focal Adhesions Decreases Cell Motility", Molecular Biology of the Cell, Aug. 1996, vol. 7, pp. 1209-1224.

Golas, J.M. et al., "SKI-606, a 4-Anilino-3-quinolinecarbonitrile Dual Inhibitor of Src and Abl Kinases, Is a Potent Antiproliferative Agent against Chronic Myelogenous Luekemia Cells in Culture and Causes Regression of K562 Xenografts in Nude Mice", Cancer Research, 2003, vol. 63, pp. 375-381.

Lombardo, L.J. et al., "Discovery of N-(2-Chloro-6-methyl-phenyl)-2-(6-(4-(2-hydroxyethyl)-piperazin-1-yl)-2-methylpyrirnidin-4-ylamino)thiazole-5-carboxamide(BMS-354825), a Dual Src/Abl Kinase Inhibitor with Potent Antitumor Activity in Preclinical Assays", Journal of Medicinal Chemistry, 2004, vol. 47, No. 27, pp. 6658-6661.

Mouawad, R. et al., "Tumoural expression and circulating level of VEGFR-3 (Flt-4) in metastatic melanoma patients: Correlation with clinical parameters and outcome", European Journal of Cancer, 2009, vol. 45, pp. 1407-1414.

Peng, C. et al., "Sequential Copper(I)-Catalyzed Reaction of Amines with o-Acetylenyl-Substituted Phenyldiazoacetates", Adv. Synth. Catal, 2008, vol. 350, pp. 2359-2364.

Stern, M. et al., "Overview of monoclonal antibodies in cancer therapy: present and promise", Critical Reviews in Oncology/Hematology, 2005, vol. 54, pp. 11-29.

Tremblay, L. et al., "Focal Adhesion Kinase (pp125FAK) Expression, Activation and Association with Paxillin and p50CSK in Human Metastatic Prostate Carcinoma", Int. J. Cancer, 1996, vol. 68, pp. 164-171.

Tsutsumi, K. et al., "Tumor growth inhibition by synthetic and expressed siRNA targeting focal adhesion kinase", International Journal of Oncology, 2008, vol. 33, pp. 215-224.

Watermann, D. et al., "Specific induction of pp 125 focal adhesion kinase in human breast cancer", British Journal of Cancer, 2005, vol. 93, No. 6, pp. 694-698.

Xu, L. et al., "Attenuation of the Expression of the Focal Adhesion Kinase Induces Apoptosis in Tumor Cells", Cell Growth & Differentiation, Apr. 1996, vol. 7, pp. 413-418.

Halder, J. et al., "Focal Adhesion Kinase Silencing Augments Docetaxel-Mediated Apoptosis in Ovarian Cancer Cells", Clinical Cancer Research, 2005, vol. 11, pp. 8829-8836.

Hong, K. et al., "Inhibition of Akt activity induces the mesenchymal-to-epithelial reverting transition with restoring E-cardherin expression in KB and KOSCC-25B oral squamous cell carcinoma cells", Journal of Experimental & Clinical Cancer Research, 2009, vol. 28, pp. 1-11.

Halder, J. et al., "Focal Adhesion Kinase Targeting Using In vivo Short Interfering RNA Delivery in Neural Liposomes for Ovarian Carcinoma Therapy", Clinical Cancer Research, Aug. 2006, vol. 12, No. 16, pp. 4916-4924.

Toutant, M. et al., "Alternative Splicing Controls fro the Mechanisms of FAK Autophosphorylation", Molecular and Cellular Biology, Nov. 2002, vol. 22, No. 22, pp. 7731-7743.

Fincham, VJ. et al., "v-Src-induced degradation of focal adhesion kinase during morphological transformation of chicken embryo fibroblasts", Oncogene, 1995, vol. 10, pp. 2247-2252.

Gan, Hui K., et al. "Focal Adhesion Kinase as a Therapeutic Target in Cancer", Jan. 2009, American Society of Clinical Oncology.

Chan, Keefe T, et al., "FAK alters invadopodia and focal adhesion composition and dynamics to regulate breast cancer invasion", J. Cell Biol. vol. 185, No. 2, p. 357-370, Apr. 13, 2009.

(56) References Cited

OTHER PUBLICATIONS

Sood, Anil K., et al., "Adrenergic modulation of focal adhesion kinase protects human ovarian cancer cells from annoikis", The Journal of Clinical Investigation, vol. 120, No. 5, May 2010.

Bottsford-Miller, Justin, et al. "Abstract LB-230: Enhancing anti-angiogenic therapy by blocking focal adhesion kinase", Cancer Research: Apr. 15, 2011; vol. 71, Issue 8, Supplement 1.

Street, I, et al., "Inhibition of Focal Adhesion Kinase in Combination with Bevacizumab Reduces the Rate of Tumor Revascularization and Increases Survival in a Pre-Clinical Model of Basal Breast Cancer", Cancer Therapeutics, CRC, Abstract 846, Jul. 2012.

SELECTIVE FAK INHIBITORS

CROSS-REFERENCE TO RELATED APPLICATIONS

This application is a continuation-in-part of International Application No. PCT/GB2012/000176, filed Feb. 17, 2012, which claims the benefit of U.S. Provisional Appl. Nos. 61/443,773, filed Feb. 17, 2011; 61/523,489, filed Aug. 15, 2011; and 61/579,729, filed Dec. 23, 2011. These prior applications are hereby incorporated by reference herein in their entirety.

SEQUENCE LISTING

The instant application contains a Sequence Listing which has been submitted in ASCII format via EFS-Web and is hereby incorporated by reference in its entirety. Said ASCII copy, created on Sep. 18, 2012, is named 02479400.txt and is 962 bytes in size.

INTRODUCTION

This invention relates to 2,4,5-substituted pyrimidines that inhibit Focal Adhesion Kinase (FAK), also known as protein tyrosine kinase 2 (PTK2), and to pharmaceutical compositions containing such compounds. This invention also relates to a method of using such compounds for the prevention and/or treatment of proliferative diseases, such as cancer.

BACKGROUND

Directional cell migration is important in many physiological and pathological processes including embryonic development, wound healing, angiogenesis, tumour invasion and metastasis. Transduction of extracellular signals, that stimulate cells to move directionally, may be induced by a number of processes including trans-membrane integrins binding to extra cellular matrix proteins and the action of growth factors (for example EGF, IGF and VEGF) on the extracellular domains of their cognate receptors.

FAK is a non receptor tyrosine kinase that mediates signals from both trans-membrane integrins and growth factor receptors. FAK has been reported to play a central role in coordinating these diverse extra cellular signals, integrating them in a fashion that results in directional movement of cells through their external environment (Tomar and Schlaepfer. Current Opinion in Cell Biology: 2009, 21, 676-683).

Integrin clustering or the activation of a growth factor receptor (for example EGFR, IGF-1R, Her2 and VEGFR) promotes FAK autophosphorylation at Y397. Phosphorylated Y397 FAK then binds to c-Src (referred to as Src herein) and Src mediated phosphorylation of FAK at Y576 and Y577 occurs to give rise to an active FAK-Src complex. Active FAK-Src then facilitates signaling via a number of biochemical pathways which influence processes such as cell adhesion, migration, invasion, cell survival, proliferation, acquisition of chemotherapy resistance and metastasis (Brunton and Frame. Current Opinion in Pharmacology: 2008, 8, 437-432 and Chatzizacharias et al. Expert Opinion in Therapeutic Targets: 2007, 11(10), 1315-1328).

Cell Adhesion

Functional studies addressing the role of FAK in cell adhesion suggest that it contributes to both focal adhesion assembly (Richardson and Parsons. Nature: 1996, 380, 538-540) and focal adhesion turnover (Fincham et al. Oncogene: 1995, 10(11), 2247-2252). Inhibition of FAK by RNAi in both human and mouse cell lines, resulting in decreased FAK protein levels, has been shown to reduce cell adhesion to a fibronectin/laminin-coated plate in vitro (Tsutsumi et al. International Journal of Oncology: 2008, 33(1), 215-224).

Cell Migration

There is strong evidence that FAK is a key regulator of cell migration (Angelucci and Bologna. Current Pharmaceutical Design: 2007, 13, 2129-2145 and Mitra et al. Nature Reviews Molecular Cell Biology: 2005, 6, 56-68). Cells derived from FAK −/− mouse embryos exhibit reduced migration as a result of impaired adhesion turnover (Ilic et al. Nature: 1995, 377, 539-544). Moreover, displacement of FAK from focal adhesions reduces cell migration (Gilmore and Romer. Molecular Biology of the Cell: 1996, 7(8), 1209-1224), whilst over-expression in CHO cells stimulates migration (Cary et al. Journal of Cell Science: 1996, 7, 1787-1794). In addition, inhibition of FAK by RNAi in both human and mouse cell lines, resulting in decreased FAK protein levels, has been shown to reduce cell migration in an in vitro haptotactic migration assay (Tsutsumi et al. International Journal of Oncology: 2008, 33(1), 215-224).

Cell Invasion

FAK activation has been shown to enhance matrix degrading invasive behaviour. FAK-Src signaling through cellular apoptosis susceptibility protein (CAS) (Liao et al. Journal of Experimental and Clinical Cancer Research: 2008, 27:15) leads to the expression of matrix metalloproteases (MMPs) including MMP2 and MMP9. FAK-Src activation also promotes cell surface expression of MMP14 via phosphorylation of endophilin A2. MMP14 then activates MMP2 by cleavage of pro-MMP2 to its active form (Siesser and Hanks. Clinical Cancer Research: 2006, 12(11), 3233-3237). Highly invasive cancer cells form specialized actin-rich extra cellular matrix degrading membrane protrusions known as invadopodia which are rich in matrix-degrading proteases such as MMPs. Both FAK and Src have been shown to be instrumental in the formation of invadopodia (Chan et al. Journal of Chemical Biology: 2009, 185(2), 357-370).

Cell Survival

FAK has been shown to play an important role in cell survival. Activation of FAK has been shown to result in suppression of anoikis (apoptosis in response to an inappropriate extra cellular matrix environment) (Frisch et al Journal of Cell Biology. 1996, 134(3), 793-799 and Xu et al Cell Growth and Differentiation. 1996, 7(4), 413-418). Studies have demonstrated that FAK activates multiple downstream pathways to suppress anoikis in both fibroblasts and epithelial cells (Zouq et al. Journal of Cell Science: 2008, 122, 357-367). In human intestinal crypt cells signalling via the association of FAK with β1 integrin and subsequent binding with Src up regulates expression of the anti-apoptotic proteins Bcl-$X_L$ and Mcl-1 via PI3-K/Akt-1 signalling. PI3-K/Akt-1 signalling also down regulates expression of the pro-apoptotic activators Bax and Bak, causes phosphorylation of the pro-apoptotic sensitizer Bad and antagonizes p38β activation. Dissociation of FAK/Src results in a sustained/enhanced activation of p38β which is an apoptosis/anoikis driver (Bouchard et al. Apoptosis: 2008, 13, 531-542).

Cell Proliferation

Reduction in the expression of either FAK or β1 integrin and hence disruption of the β1-FAK signalling axis results in decreased initial proliferation of micro-metastatic cells distributed in the lung. Using 3D cultured D2 cells a strong correlation was observed between FAK Y397 and Y861 phosphorylation and proliferative ability (Shibue and Weinberg. PNAS 2009, 106(25), 10290-10295). HL-60 Cells, transfected to over express FAK, have been shown to double at a rate 1.5 times faster than control HL-60 cells. Studies revealed a marked induction of cyclin D3 expression and CDK activity in the cells over expressing FAK. Activation of PI3-K/Akt-1 signalling, a process associated with FAK activation in a number of studies, was identified as a probable cause of the cyclin expression/activation (Yamamoto et al. Cellular Signaling: 2003, 15. 575-583).

Acquisition of Chemotherapy Resistance

Exposure of the cisplatin sensitive ovarian cancer cell line OAW42 to repeated cycles of cisplatin treatment and subsequent recovery resulted in the formation of chemo-resistant OAW42-R cells. Studies aimed at identifying the cause of this chemo-resistance revealed that FAK was constituently active in both the sensitive and chemo-resistant cells. However, inhibition of phosphorylation of Y397 FAK was induced by treatment with cisplatin in OAW42 cells but not in OAW42-R cells (Poulain and co-workers. Gynaecologic oncology: 2006, 101, 507-519). The effects of FAK inhibition on chemo-resistance has also been studied in vitro and in vivo using the FAK inhibitor TAE226, alone and in combination with docetaxel, in taxane-sensitive (SKOV3ip1 and HeyA8) and taxane-resistant (HeyA8-MDR) ovarian cancer cell lines. TAE226 has the structure:

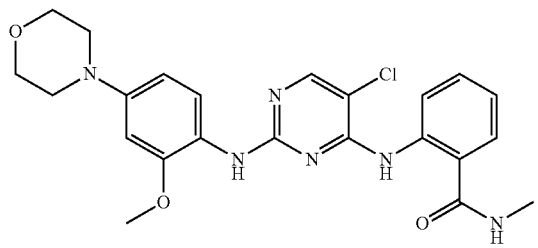 [SMILES: CNC(=O)c1ccccc1Nc1nc(Nc2ccc(N3CCOCC3)cc2OC)ncc1Cl]

and is described in WO 2004/080980 and WO 2005/016894. In vitro, TAE226 inhibited the phosphorylation of FAK at both Y397 and Y861 sites, inhibited cell growth in a time- and dose-dependent manner, and enhanced docetaxel-mediated growth inhibition by 10- and 20-fold in the taxane-sensitive and taxane-resistant cell lines, respectively. In vivo, FAK inhibition by TAE226 significantly reduced tumour burden in the HeyA8, SKOV3ip1, and HeyA8-MDR models (46-64%) compared with vehicle-treated controls. However, the greatest efficacy was observed with concomitant administration of TAE226 and docetaxel in all three models (85-97% reduction). In addition, TAE226 in combination with docetaxel significantly prolonged survival in tumour-bearing mice (Halder et al. Cancer Res: 2007, 67(22), 10976-10983).

Metastatic Potential

Several studies have examined the role of FAK protein levels and it's relation to tumor progression in animal models. In a mouse skin carcinogenesis model using FAK +/- mice, reduced FAK protein expression correlated with decreased papilloma formation (46%), compared with FAK +/+ wild-type control mice (McLean et al. Cancer Research: 2001, 61, 8385-8389). Using human breast carcinoma cells, researchers showed that FAK siRNA treated cells were inhibited from metastasizing to the lung after orthotopic implantation in nude mice (Benlimame et al. Journal of Cell Biology: 2005, 171, 505-516). Similar experiments using short hairpin RNA (shRNA) against FAK in 4T1 mouse breast carcinoma cells resulted in an inhibition of metastasis to the lungs after orthotopic implantation in mammary pads (Mitra et al. Oncogene: 2006, 25, 4429-4440). Inhibition of FAK by dominant negative expression in 4T1 mouse breast carcinoma cells reduced tumour growth and angiogenesis in mice (Mitra et al. Oncogene: 2006, 25, 5969-5984). Use of a Cre/loxP recombination system to disrupt FAK function in the mammary epithelium of a transgenic model of breast cancer has demonstrated that FAK expression is required for the transition of premalignant hyperplasias to carcinomas and their subsequent metastases. The observed decrease in tumor progression was further correlated with impaired mammary epithelial proliferation suggesting that FAK plays a critical role in mammary tumor progression (Lahlou et al. PNAS USA: 2007, 104(51), 20302-20307).

In accordance with the above observations over expression of FAK mRNA and/or protein has been reported in numerous human cancers including colorectal cancer (de Heer. European Journal of Surgical Oncology: 2008, 34(11), 1253-1261), prostate cancer (Tremblay, L., W. Hauck, et al. International Journal of Cancer: 1996, 68(2), 164-171), breast cancer (Watermann et al. British Journal of Cancer 2005, 93(6), 694-698) and melanomas (Hess et al. Cancer Research: 2005, 65(21), 9851-60). Furthermore FAK over expression is frequently correlated with more aggressive phenotypes of these cancers.

Thus, there is strong evidence to suggest that a FAK inhibitor would have application for the reduction of cell adhesion, cell migration, cell invasion, cell proliferation and chemo-resistance. Furthermore, a FAK inhibit would have applicability to induce apoptosis for cells in inappropriate extra cellular matrix environments and reduce angiogenesis.

A compound which is a seltective FAK inhibitor would enable the targeting of specific biological pathways, without any potential issues caused by the inhibition of any targets, such as other protein kinases.

Accordingly, compounds that selectively inhibit FAK would be useful for the treatment of proliferative diseases, such as cancer.

Two compounds reported to inhibit FAK are PF-562,271 and PF-573,228.

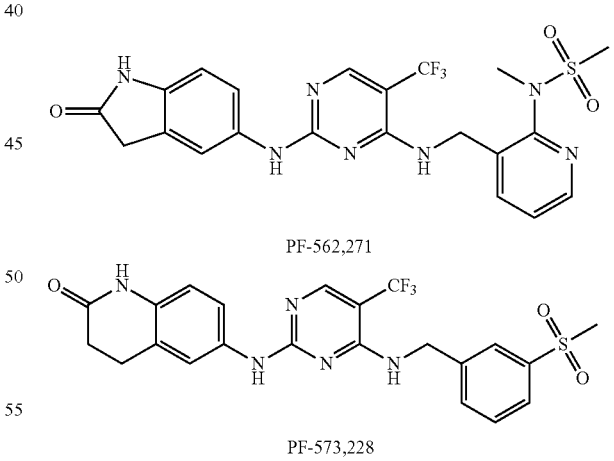

PF-562,271 is described in WO2004/056786, WO2004/056807, WO2005/023780, WO2007/063384 and Roberts et al. Cancer Res 2008, 68(6), 1935-1944.

PF-573,228 is described in Slack-Davis et al. J. Biol. Chem. 2007, 282(20), 14845-14852.

In addition to these specifically described compounds, further classes of FAK inhibitors are disclosed in WO2008/129380, WO2008/115369, WO2009/105498, US2010/113475, WO2009/143389, WO2009/071535, WO2010/

055117, WO2010/058030, WO2010/058032, WO2007/140222, and WO2009/024332.

SUMMARY OF THE INVENTION

The present inventors have discovered a particular class of compounds which are effective as selective FAK inhibitors. These compounds may exhibit selectivity for FAK over kinases such as IGF-1R (Insulin-like growth factor 1 receptor), IR (insulin receptor) and CDKs (cyclin-dependent kinases), as well as over other kinases, such as VEGFR1, VEGFR2 and VEGFR3. Additionally, the compounds of the invention may have enhanced selectivity for the inhibition of cytochrome p450 enzymes, specifically the 2C9 and 3A4 isoforms. Furthermore, the compounds of the invention may be less prone to the formation of adducts with glutathione.

In a first aspect, the present invention provides compounds of the following formula (I):

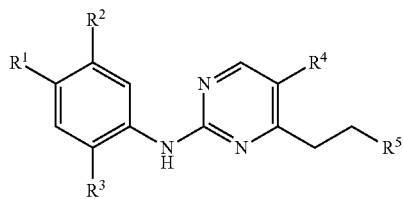

(I)

wherein:
$R^1$ is selected from: H and

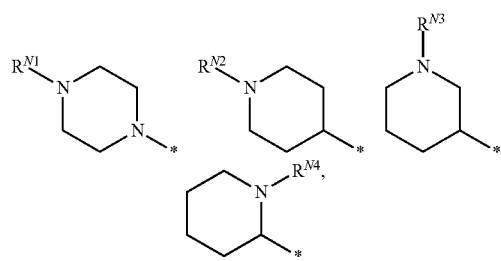

wherein:
$R^{N1}$ is selected from H, $C_{1-3}$ alkyl and $C(=O)Me$;
$R^{N2}$ is selected from H, $C_{1-3}$ alkyl and $C(=O)Me$;
$R^{N3}$ is selected from H, $C_{1-3}$ alkyl and $C(=O)Me$;
$R^{N4}$ is selected from H and $CH_3$;
$R^2$ is selected from H and

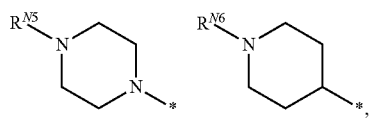

wherein:
$R^{N5}$ is selected from H, $C_{1-3}$ alkyl and $C(=O)Me$;
$R^{N6}$ is selected from H, $C_{1-3}$ alkyl and $C(=O)Me$;
and wherein only one of $R^1$ and $R^2$ is H;
$R^3$ is selected from O—$C_{1-2}$ alkyl, $C_{1-2}$ alkyl, halo, cyano, where the $C_{1-2}$ alkyl group may be substituted by one or more fluoro groups;
$R^4$ is selected from $CF_3$, halo, $CF_2H$ and CN; and $R^5$ is selected from groups of the following formulae:

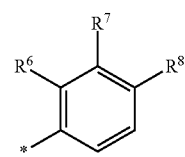

($R^{5a}$)

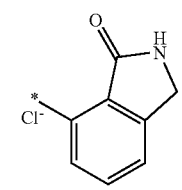

($R^{5b}$)

wherein:
$R^6$ is selected from H, $(CHR^{C1})_{n1}C(O)N(R^{N6})Z^1$ and $(CH_2)_{n2}C(O)OZ^2$; wherein:
n1 is 1;
$R^{C1}$ is H or Me;
$R^{N6}$ is H or $CH_3$;
$Z^1$ is H, $CH_3$ or $OCH_3$;
n2 is 1; and
$Z^2$ is $CH_3$;
and where only one of $R^{N6}$ and $Z^1$ can be $CH_3$,
$R^7$ is selected from H, and $(CH_2)_{m1}C(O)N(R^{M1})Y^1$, wherein:
m1 is 0 or 1;
$R^{M1}$ is H; and
$Y^1$ is H, Me or $OCH_3$;
and only one of $R^6$ and $R^7$ is H; and
$R^8$ is H or, when $R^7$ is $C(=O)NH_2$, $R^8$ is selected from H and $C_{1-2}$ alkyl.

A second aspect of the present invention provides a composition comprising a compound of the first aspect and a pharmaceutically acceptable carrier or diluent.

A third aspect of the invention provides a compound of the first aspect for use in a method of therapy.

A fourth aspect of the invention provides for the use of a compound of the first aspect in the preparation of a medicament for treating a disease ameliorated by the inhibition of FAK. The fourth aspect of the invention also provides a compound of the first aspect for use in the method of treatment of a disease ameliorated by the inhibition of FAK.

A further aspect of the invention provides an active compound as described herein for use in a method of treatment of the human or animal body, preferably in the form of a pharmaceutical composition.

Another aspect of the invention provides a method of inhibiting FAK in vitro or in vivo, comprising contacting a cell with an effective amount of an active compound as described herein.

Each of the groups $R^1$ to $R^8$ will be discussed in more detail below.

$R^1$ $R^1$ may have one of the following structures:

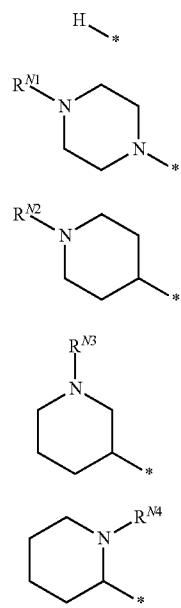

(R$^{1a}$)
(R$^{1b}$)
(R$^{1c}$)
(R$^{1d}$)
(R$^{1e}$)

When $R^1$ is H, $R^2$ (discussed below) is not H.

Each of $R^{N1}$, $R^{N2}$ and $R^{N3}$ is independently selected from H, $C_{1-3}$ alkyl (i.e. methyl, ethyl, prop-1-yl and prop-2-yl) and C(=O)Me and $R^{N4}$ is selected from either H or methyl.

$R^2$ $R^2$ may have one of the following structures:

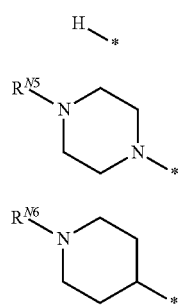

(R$^{2A}$)
(R$^{2B}$)
(R$^{2C}$)

When $R^2$ is H, $R^1$ (discussed above) is not H.

$R^{N5}$ and $R^{N6}$ are independently is selected from H, $C_{1-3}$ alkyl (i.e. methyl, ethyl, prop-1-yl and prop-2-yl) and C(=O)Me.

$R^3$ $R^3$ is selected from O—$C_{1-2}$ alkyl, $C_{1-2}$ alkyl, halo, cyano, where the $C_{1-2}$ alkyl group may be substituted by one or more fluoro groups. Thus, $R^3$ may be:
a) halo: F, Cl, Br, I;
b) cyano: CN
c) $C_{1-2}$ alkyl, optionally substituted by one or more fluoro groups: $CH_3$, $CH_2F$, $CHF_2$, $CF_3$, $CH_2CH_3$, $CH_2CH_2F$, $CH_2CHF_2$, $CH_2CF_3$, $CHFCH_3$, $CHFCH_2F$, $CHFCHF_2$, $CHFCF_3$, $CF_2CH_3$, $CF_2CH_2F$, $CF_2CHF_2$, $CF_2CF_3$;
d) O—$C_{1-2}$ alkyl, wherein the $C_{1-2}$ alkyl group is optionally substituted by one or more fluoro groups: O—$CH_3$, O—$CH_2F$, O—$CHF_2$, O—$CF_3$, O—$CH_2CH_3$, O—$CH_2CH_2F$, O—$CH_2CHF_2$, O—$CH_2CF_3$, O—$CHFCH_3$, O—$CHFCH_2F$, O—$CHFCHF_2$, O—$CHFCF_3$, O—$CF_2CH_3$, O—$CF_2CH_2F$, O—$CF_2CHF_2$, O—$CF_2CF_3$.

$R^4$ $R^4$ is selected from $CF_3$, halo (i.e. F, Cl, Br, I), $CF_2H$ and CN.

In some embodiments, the halo group is either Cl or Br.

$R^5$ $R^5$ is selected from groups of the following formulae:

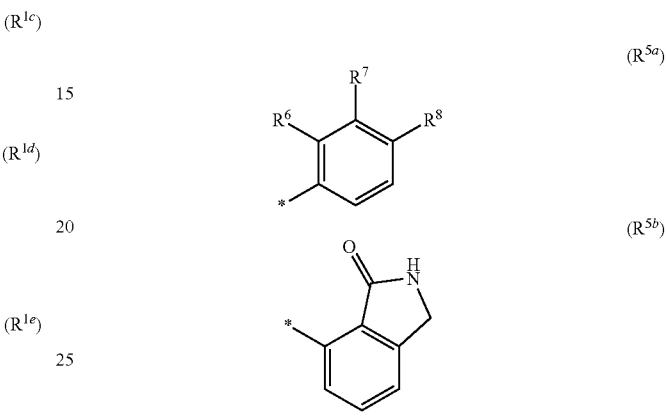

(R$^{5a}$)
(R$^{5b}$)

$R^6$ $R^6$ is selected from H, $(CHR^{C1})_{n1}C(O)N(R^{N6})Z^1$ and $(CH_2)_{n2}C(O)OZ^2$; wherein:
n1 is 1;
$R^{C1}$ is H or Me;
$R^{N6}$ is H or $CH_3$;
$Z^1$ is H, $CH_3$ or $OCH_3$;
n2 is 1; and
$Z^2$ is $CH_3$;
wherein only one of $R^{N6}$ and $Z^1$ may be $CH_3$.

When $R^6$ is H, $R^7$ (discussed below) is not H.

If $R^6$ is $(CHR^{C1})_{n1}C(O)N(R^{N6})Z^1$, it may be selected from: $CH_2C(O)NH_2$, $CH_2C(O)NHCH_3$, $CH_2C(O)NHOCH_3$, $CH_2C(O)NCH_3OCH_3$, $CHCH_3C(O)NH_2$, $CHCH_3C(O)NHCH_3$, $CHCH_3C(O)NHOCH_3$, and $CHCH_3C(O)NCH_3OCH_3$.

If $R^6$ is $(CH_2)_{n2}C(O)OZ^2$, it is $CH_2C(O)OCH_3$.

$R^7$

H, and $(CH_2)_{m1}C(O)N(R^{M1})Y^1$, wherein:
m1 is 0 or 1;
$R^{M1}$ is H; and
$Y^1$ is H, Me or $OCH_3$;
When $R^7$ is H, $R^6$ (discussed above) is not H.

When $R^7$ is $(CH_2)_{m1}C(O)N(R^{M1})Y^1$, it may be selected from $C(O)NH_2$, $C(O)NHCH_3$, $C(O)NHOCH_3$, $CH_2C(O)NH_2$, $CH_2C(O)NHCH_3$ and $CH_2C(O)NHOCH_3$.

$R^8$ $R^8$ is H, except for when $R^7$ is $C(=O)NH_2$, it may alternatively be $C_{1-2}$ alkyl. i.e. methyl or ethyl.

Includes Other Forms

Included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and isopropyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

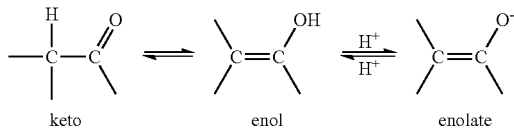

keto    enol    enolate

Note that specifically included in the term "isomer" are compounds with one or more isotopic substitutions. For example, H may be in any isotopic form, including ¹H, ²H (D), and ³H (T); C may be in any isotopic form, including ¹²C, ¹³C and ¹⁴C; O may be in any isotopic form, including ¹⁶O and ¹⁸O; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al. J. Pharm. Sci., 66, 1-19 (1977).

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as $Ca^{2+}$ and $Mg^{2+}$, and other cations such as $Al^{3+}$. Examples of suitable organic cations include, but are not limited to, ammonium ion (i.e., $NH^{4+}$) and substituted ammonium ions (e.g., $NH_3R^+$, $NH_2R^{2+}$, $NHR^{3+}$, $NR^{4+}$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)^{4+}$.

If the compound is cationic, or has a functional group which may be cationic (e.g., —NH₂ may be —NH³⁺), then a salt may be formed with a suitable anion. Examples of suitable inorganic anions include, but are not limited to, those derived from the following inorganic acids: hydrochloric, hydrobromic, hydroiodic, sulphuric, sulphurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc. It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH₃, —OAc).

For example, an aldehyde or ketone group may be protected as an acetal or ketal, respectively, in which the carbonyl group (>C=O) is converted to a diether (>C(OR)₂), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as an ester for example, as: an C$_{1-7}$ alkyl ester (e.g. a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties. For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is C1-7 alkyl (e.g. -Me, -Et); C$_{1-7}$ aminoalkyl (e.g. aminoethyl; 2-(N,N-diethylamino)ethyl; 2-(4-morpholino)ethyl); and acyloxy-C$_{1-7}$ alkyl (e.g. acyloxymethyl; acyloxyethyl; e.g. pivaloyloxymethyl; acetoxymethyl; 1-acetoxyethyl; 1-(1-methoxy-1-methyl) ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl) carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Selectivity

The selectivity of the compounds for inhibiting FAK over other kinases such as VEGFR1, VEGFR2 and/or VEGFR3, IGF-1R, IR and CDKs can be demonstrated by biochemical assay results (see, for example, the FAK kinase assay and VEGFR3 assays described below).

The selectivity of the compounds for FAK over the inhibition of cytochrome p450 enzymes, specifically the 2C9 and 3A4 isoforms may be determined using standard inhibition assays.

How prone the compounds of the invention may be to the formation of adducts with glutathione may be determined by the protocol described in Walker, et al. Biorg. Med. Chem. Letts. 2008, 18, 6071-6077.

The selectivity of compounds for inhibiting FAK over other enzymes may be expressed as ratio of other enzyme's inhibition (IC$_{50}$) to the FAK inhibition (IC$_{50}$). For example, to determine the selectivity of a compound for inihibitng FAK over VEGFR3, the compound's IC$_{50}$ for VEGFR3 is divided by the compound's IC$_{50}$ for FAK to give a ratio. The higher the ratio, the more selective the compound is.

Avastin-open squares; compound 3 +Avastin-open triangles. All symbols represent the mean ±SEM of 8 mice per group. * p <0.05 compared to Avastin alone by t-test.

Figure 5:
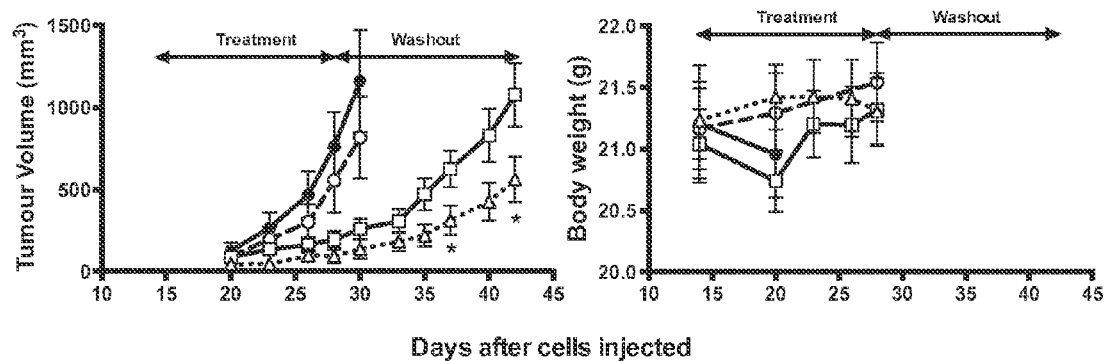
FIG. 5 shows (a) tumour volume and (b) body weight of tumour bearing mice treated with Compound 3 80mg/kg p.o. OD) and/or avastin (12.5mg/kg i.p. twice weekly); HPMC-SV (vehicle, control)-closed circles; compound 3-open circles.
Figure 6:
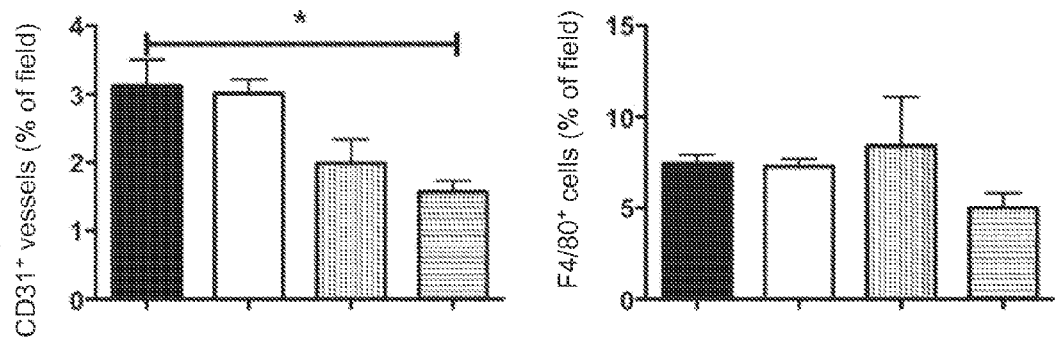

FIG. 6 shows quantitated CD31+blood vessel staining (left panel) and F4/80+mature macrophage staining (right panel) in the tumours from FIG. 5; HPMC-SV control-black bar; compound 3-white bar; Avastin-vertical striped bar; Avastin +compound 3-horizontal striped bar. All bars represent the mean ±S.E.M of n =8 per group. * p <0.05 by one-way ANOVA.

FURTHER EMBODIMENTS

The following embodiments and preferences may be combined with one another as appropriate.

In some embodiments, $R^2$ is H and $R^1$ is:

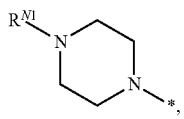

wherein $R^{N1}$ is selected from H, $C_{1-3}$ alkyl (i.e. methyl, ethyl, prop-1-yl and prop-2-yl) and C(=O)Me. In some of these embodiments, it may be preferred that $R^{N1}$ is C(=O)Me. In others of these embodiments, it may be preferred that $R^{N1}$ is methyl or ethyl. In further of these embodiments, it may be preferred that $R^{N1}$ is H.

In other embodiments, $R^2$ is H and $R^1$ is:

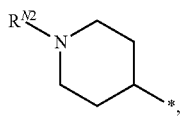

wherein $R^{N2}$ is selected from H and $C_{1-3}$ alkyl (i.e. methyl, ethyl, prop-1-yl and prop-2-yl). In these embodiments, it may be preferred that $R^{N2}$ is selected from H and methyl. In these embodiments, it may also be preferred that $R^{N2}$ is ethyl.

In other embodiments, $R^2$ is H and $R^1$ is:

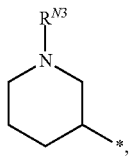

wherein $R^{N3}$ is selected from H and $C_{1-3}$ alkyl (i.e. methyl, ethyl, prop-1-yl and prop-2-yl). In these embodiments, it may be preferred that $R^{N3}$ is selected from H and methyl.

In other embodiments, $R^2$ is H and $R^1$ is:

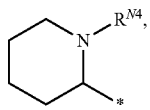

wherein $R^{N4}$ is selected from H and methyl. In these embodiments, it may be preferred that $R^{N4}$ is H.

In some embodiments, $R^1$ is H and $R^2$ is:

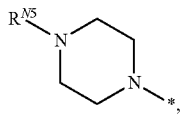

where $R^{N5}$ is selected from H and $C_{1-3}$ alkyl (i.e. methyl, ethyl, prop-1-yl and prop-2-yl). In these embodiments, it may be preferred that $R^{N5}$ is selected from H and methyl.

It may be preferred that $R^1$ is selected from:

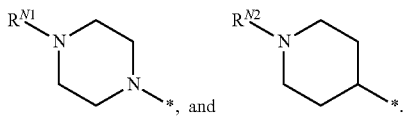

In some embodiments, $R^1$ is H and $R^2$ is:

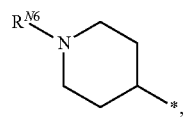

where $R^{N6}$ is selected from H and $C_{1-3}$ alkyl (i.e. methyl, ethyl, prop-1-yl and prop-2-yl). In these embodiments, it may be preferred that $R^{N6}$ is selected from H and methyl.

It may be further preferred that $R^1$ is H and $R^2$ is:

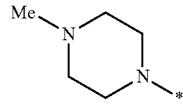 [SMILES: *N1CCN(C)CC1]

In some embodiments, $R^3$ is selected from F, Me, Et, OMe and $OCF_3$. In some of these embodiments, $R^3$ is OMe.

In some embodiments, $R^4$ is selected from $CF_3$, Cl, Br, $CF_2H$, and CN.

In further embodiments, $R^4$ is selected from $CF_3$, $C_1$ and $CF_2H$. In further embodiments, $R^4$ is selected from $CF_3$ and Cl. It may be preferred that $R^4$ is $CF_3$.

In some embodiments, it may be preferred that $R^5$ is a group of the following formulae:

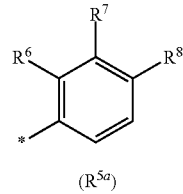

$(R^{5a})$

In some embodiments, $R^7$ is H and $R^6$ is $(CHR^{C1})_{n1}C(O)N(R^{N6})Z^1$.

In further embodiments, $R^7$ is H and $R^6$ is selected from $CH_2C(O)NH_2$, $CH_2C(O)NHCH_3$, $CHCH_3C(O)NH_2$ and $CHCH_3C(O)NHCH_3$.

It may be preferred that $R^7$ is H and $R^6$ is selected from $CH_2C(O)NH_2$, $CHCH_3C(O)NH_2$ and $CH_2C(O)NHCH_3$, and more preferably from $CH_2C(O)NH_2$, and $CHCH_3C(O)NH_2$. Most preferably $R^6$ is $CH_2C(O)NH_2$.

In some embodiments, $R^6$ is H and $R^7$ is $(CH_2)_{m1}C(O)N(R^{M1})Y^1$.

In further embodiments, $R^6$ is H and $R^7$ is selected from $C(O)NH_2$, $C(O)NHCH_3$, $CH_2C(O)NH_2$ and $CH_2C(O)NHCH_3$.

It may be preferred that $R^6$ is H and $R^7$ is $C(O)NH_2$.

In some embodiments where $R^6$ is H and $R^7$ is $C(O)NH_2$, $R^8$ is methyl.

In some embodiments, it may be preferred that $R^5$ is a group of the following formula:

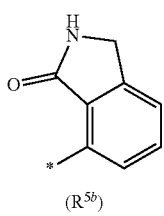 [SMILES: *c1cccc2c1C(=O)NC2]

(R$^{5b}$)

In selected embodiments of the invention, the compounds may of formula Ia:

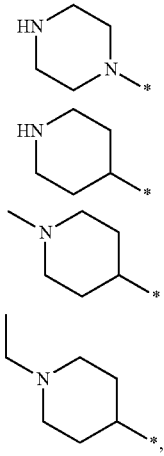

(Ia)

wherein R$^{1a}$ is selected from:

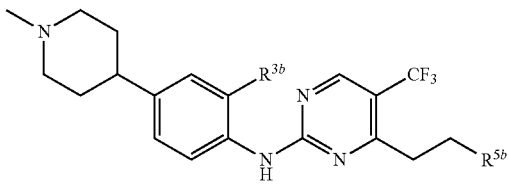

and R$^{3a}$ is selected from Me, Et, OMe, OCF$_3$, and F.

In selected embodiments of the invention, the compounds may of formula Ib:

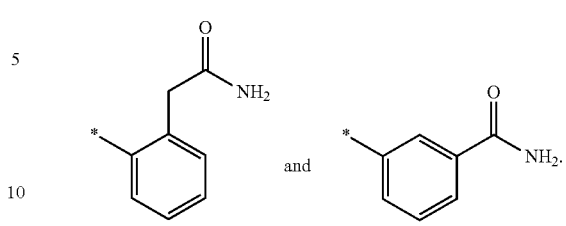

(Ib)

wherein R$^{3b}$ is selected from OMe and OCF$_3$, and R$^{5b}$ is selected from:

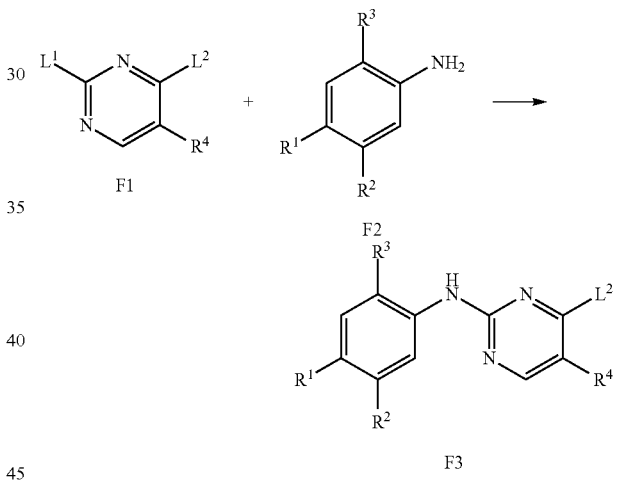

Embodiments of the inventions are compounds of the examples, including compounds 1 to 13. Embodiments of particular interest include compounds 3, 6 and 11.

General Synthesis Methods

The compounds of the invention can be prepared employing the following general methods and using procedures described in detail in the experimental section. The reaction conditions referred to are illustrative and non-limiting.

Compounds of formula I, as described above, can be prepared by synthetic strategies outlined below, wherein the definitions above apply:

Scheme A

Compounds of formula F1 may be reacted with substituted synthetic anilines of formula F2 (as prepared in scheme C, D, E, F, G and H) to form intermediates of formula F3 where L$^1$ and L$^2$ may be the same or different and include Cl, Br, I, SMe, SO$_2$Me and R$^4$=CF$_3$, halogen, CF$_2$H or CN.

Compounds of the formula F1 may be prepared where L$^1$ and L$^2$ are different (see scheme B) to allow regioselective substitution or when L$^1$=L$^2$ suitable reaction conditions can be employed (choice of solvent, reaction temperature, addition of a Lewis acid, for example ZnCl$_2$ in diethyl ether) to allow L$^1$ to be selectively displaced over L$^2$. Where regiochemical mixtures and di-substitution are obtained the regioisomers may be separated by chromatography.

Compounds of the formula F1 where L$^1$=L$^2$ are either commercially available, for example 2,4-dichloro-5-(trifluoromethyl)pyrimidine, 2,4-dichloro-5-fluoropyrimidine, 2,4,5-trichloropyrimidine, 2,4-dichloro-5-bromopyrimidine, iodopyrimidine, 2,4-dichloro-5-cyanopyrimidine or may be prepared readily from commercial starting materials. Where R$^4$=CF$_3$ and differentiation of L$^1$ and L$^2$ is desirable, the method outlined in scheme B may be employed.

Scheme B

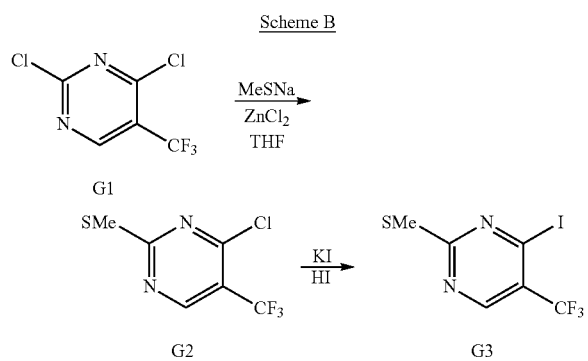

Commercially available 2,4-dichloro-5-(trifluoromethyl) pyrimidine (G1) can be selectively reacted with sodium thiomethoxide in the presence of zinc(II) chloride to give 2-thiomethyl-4-chloro-5-(trifluoromethyl)pyrimidine (G2). 2-Thiomethyl-4-chloro-5-(trifluoromethyl)pyrimidine (G2) can be further reacted, for example by conversion to 2-thiomethyl-4-iodo-5-(trifluoromethyl)pyrimidine (G3) under Finkelstein conditions and/or by oxidation with mCPBA to give the corresponding sulfone if further differentiation of the 2 and 4-position is required or if additional activation is desirable.

Scheme C

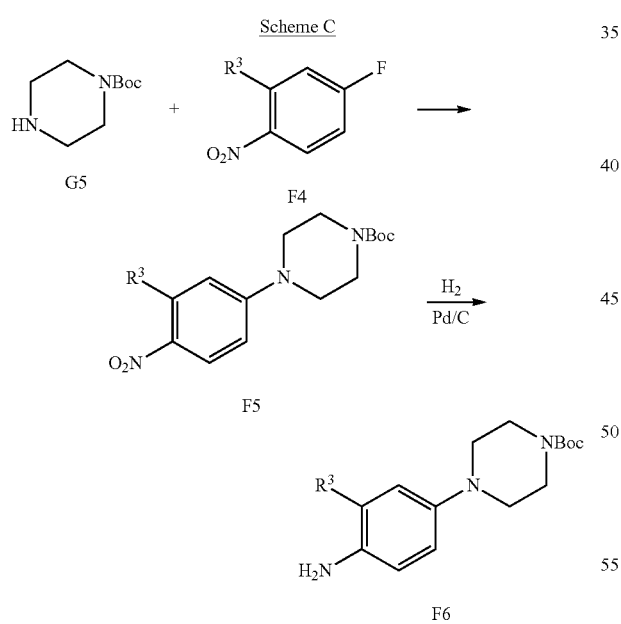

Commercially available tert-butyl piperazine-1-carboxylate (G5) and 4-fluoro-2-substituted-1-nitrobenzenes of the formula F4 can be reacted in an S$_N$Ar reaction to give tert-butyl 4-(3-substituted-4-nitrophenyl)piperazine-1-carboxylates of the formula F5. Subsequent reduction via hydrogenation in the presence of a catalyst, for example palladium on charcoal or platinum oxide when R$^3$ is Cl, Br or I, gives the corresponding anilines of the formula F6.

Scheme D

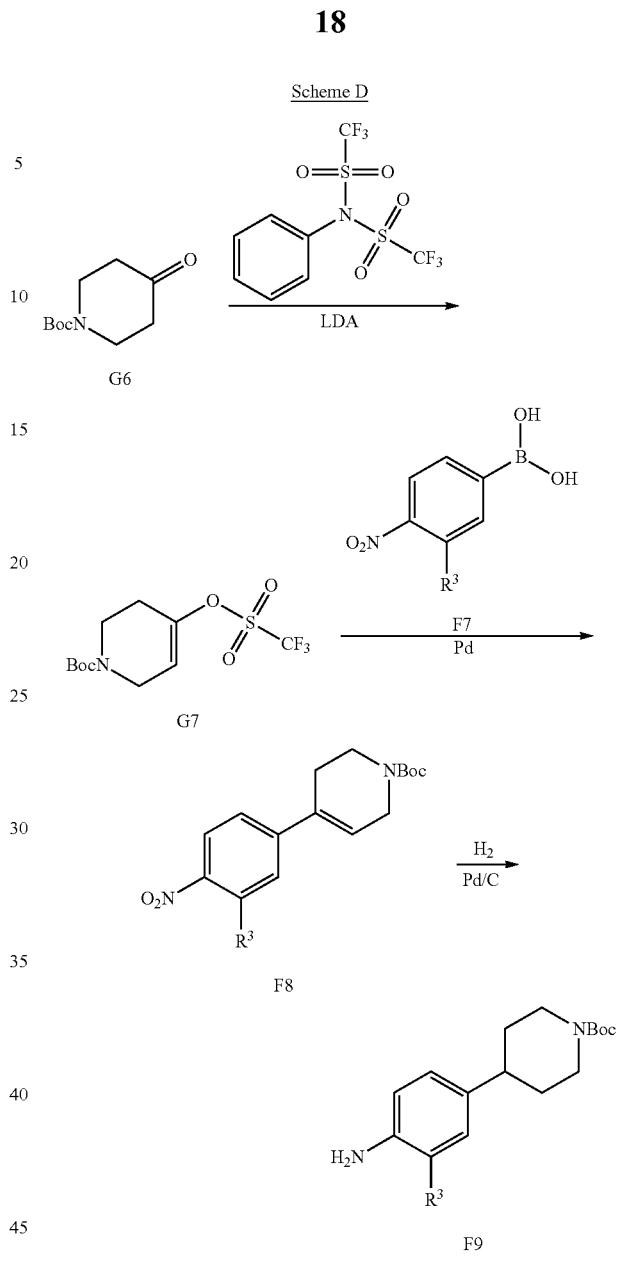

The corresponding 4-piperidine analogues of F6 can be prepared by a sequence of reactions starting with the conversion of commercially available tert-butyl 4-oxopiperidine-1-carboxylate (G6) to vinyl triflate G7. Coupling of G7 in a Suzuki type reaction with aryl boronic acids, or analogous boronic esters, of the formula F7 gives tetrahydropyridines of the formula F8. Subsequent reduction via hydrogenation in the presence of a catalyst, for example palladium on charcoal, gives anilino-piperidines of the formula F9. Alternatively, protected aniline analogues of compounds of the formula F7, for example Boc or CBz protected anilines, can be employed in the Suzuki coupling step. This negates the need for a later reduction step and may be beneficial when R$^3$ is halo.

Scheme E

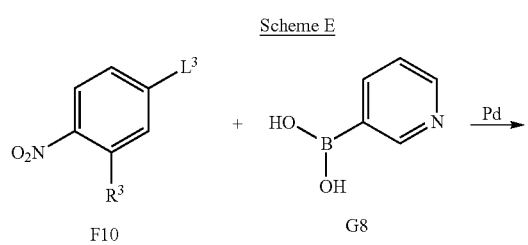

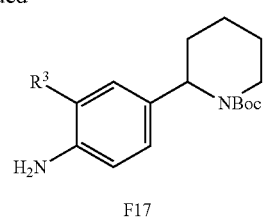

3-Piperidine analogues can be prepared by reaction of commercially available compounds of the formula F10, where $L^3$=I or Br, with pyridin-3-ylboronic acid (G8) in a Suzuki type reaction to form intermediates of the formula F11. Reduction of compounds of the formula F11 with hydrogen in the presence of a catalyst, for example platinum oxide, gives intermediates of the formula F12 which may be protected using Boc anhydride to give compounds of the formula F13.

Scheme F

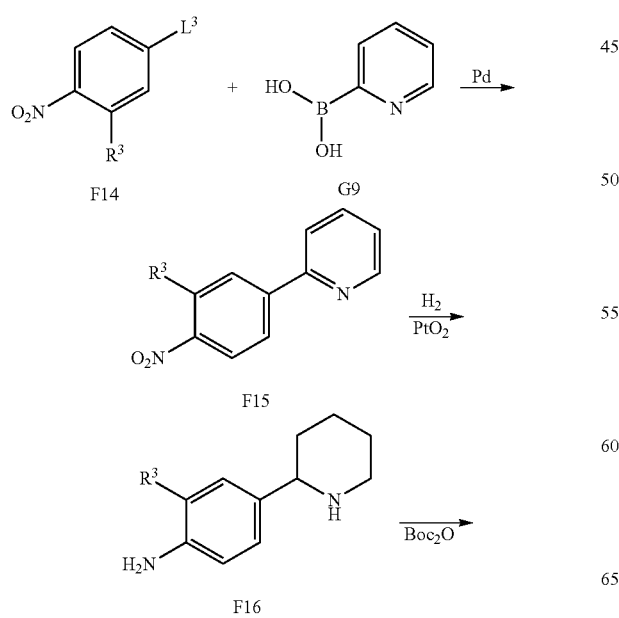

2-Piperidine analogues can be prepared by reaction of commercially available compounds of the formula F14, where $L^3$=I or Br, with pyridin-2-ylboronic acid (G9) in a Suzuki type reaction to form intermediates of the formula F15. Reduction of compounds of the formula F15 with hydrogen in the presence of a catalyst, for example platinum oxide, gives intermediates of the formula F16 which may be protected using Boc anhydride to give compounds of the formula F17.

Scheme G

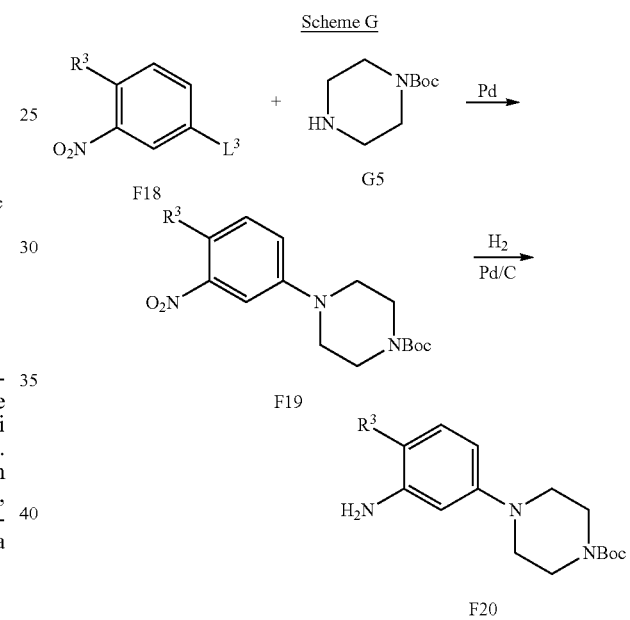

Compounds of the formula F20 can be prepared by coupling of commercially available tert-butyl piperazine-1-carboxylate (G5) and compounds of the formula F18, where $L^3$=I or Br, in a Buchwald type reaction to give intermediates of the formula F19. Compounds of the formula F19 can be reduced with hydrogen in the presence of a catalyst, for example palladium on charcoal or platinum oxide, to give anilines of the formula F20.

Scheme H

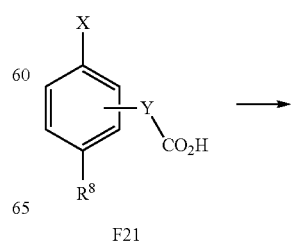

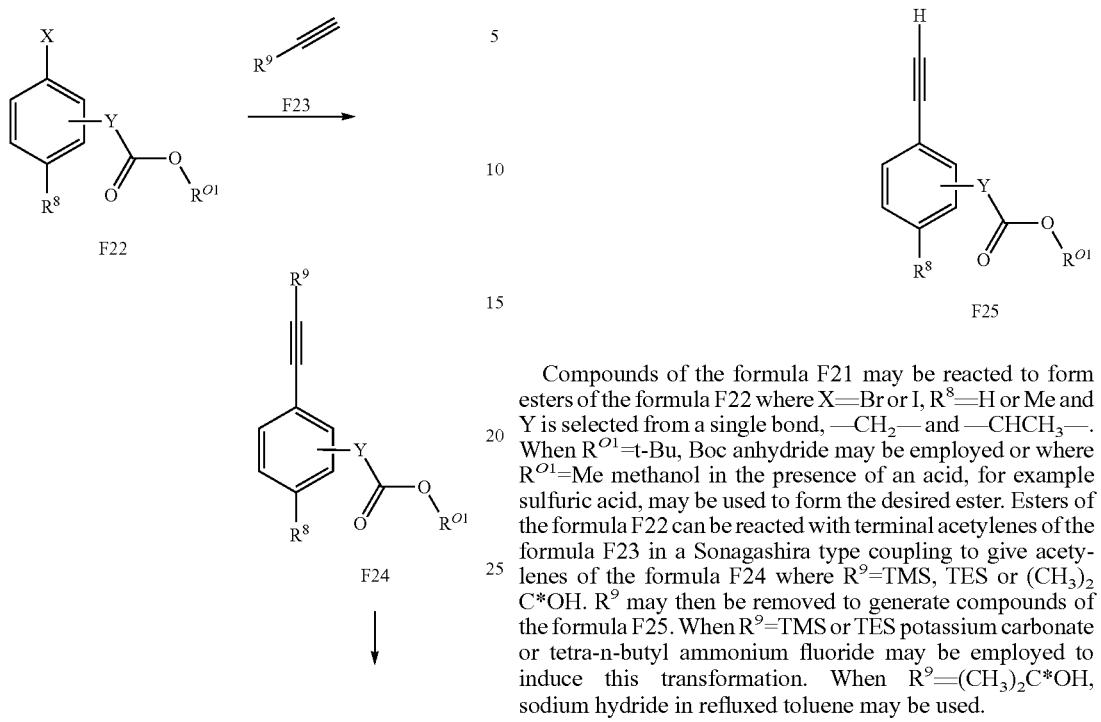

Compounds of the formula F21 may be reacted to form esters of the formula F22 where X=Br or I, $R^8$=H or Me and Y is selected from a single bond, —$CH_2$— and —$CHCH_3$—. When $R^{O1}$=t-Bu, Boc anhydride may be employed or where $R^{O1}$=Me methanol in the presence of an acid, for example sulfuric acid, may be used to form the desired ester. Esters of the formula F22 can be reacted with terminal acetylenes of the formula F23 in a Sonagashira type coupling to give acetylenes of the formula F24 where $R^9$=TMS, TES or $(CH_3)_2$C*OH. $R^9$ may then be removed to generate compounds of the formula F25. When $R^9$=TMS or TES potassium carbonate or tetra-n-butyl ammonium fluoride may be employed to induce this transformation. When $R^9$=$(CH_3)_2$C*OH, sodium hydride in refluxed toluene may be used.

Scheme I

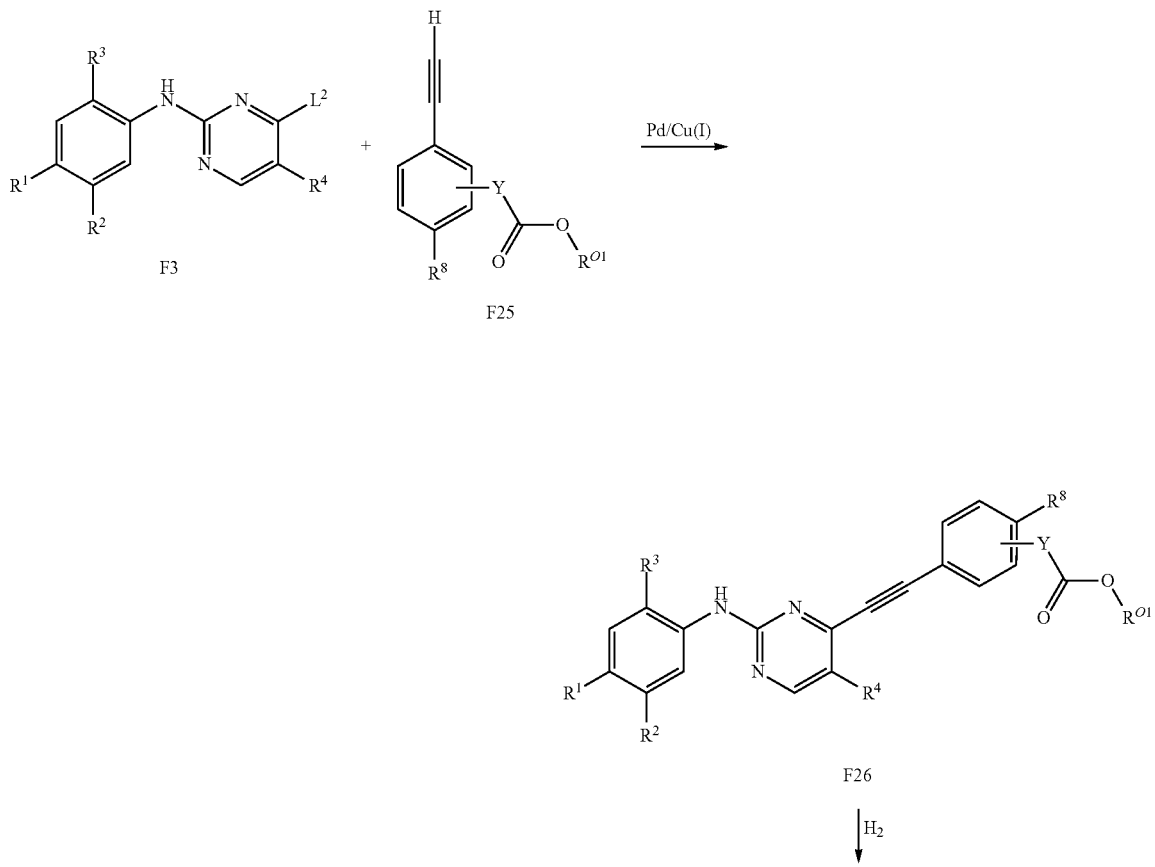

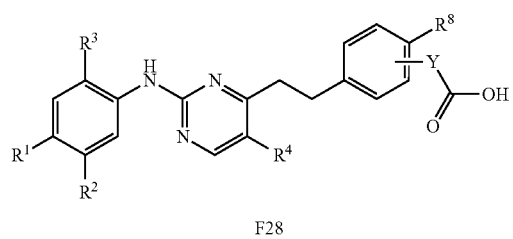

F28

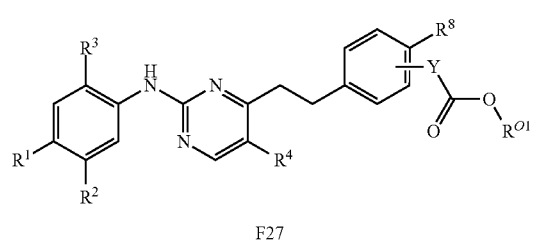

F27

Pyrimidines of the formula F3 may be reacted with terminal acetylenes of the formula F25 to give acetylenes of the formula F26 in a Sonagashira type coupling. The acetylene in compounds of the formula F26 may be reduced to an alkane of the formula F27 using hydrogen gas in the presence of a transition metal catalyst. The exact choice of catalyst and conditions employed is dependant on the nature of $R^4$. For example, where $R^4$=$CF_3$, 10% Pd/C may be used, where $R^4$=Cl, platinum oxide is employed. Esters of the formula F27 may then be deprotected to give carboxylic acids of the formula F28. Where $R^{O1}$=Me or Et, lithium hydroxide solutions may be employed. Where $R^{O1}$=t-Bu, acidic solutions, for example trifluoroacetic acid in dichloromethane may be used. It will be appreciated that under acidic conditions Boc protecting groups in $R^1$ and $R^2$ will also be cleaved.

Scheme J

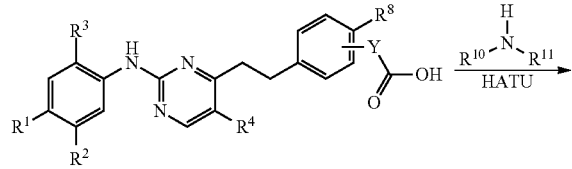

F28

-continued

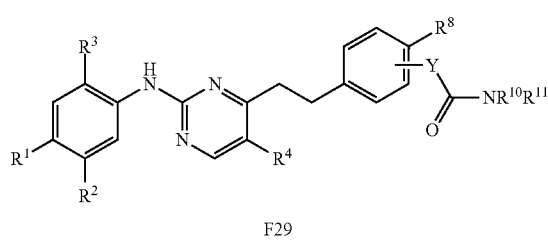

F29

Carboxylic acids of the formula F28 can be converted to amides of the formula F29 using a suitable amine or ammonia salt in the presence of a peptide coupling agent, for example HATU.

Scheme K

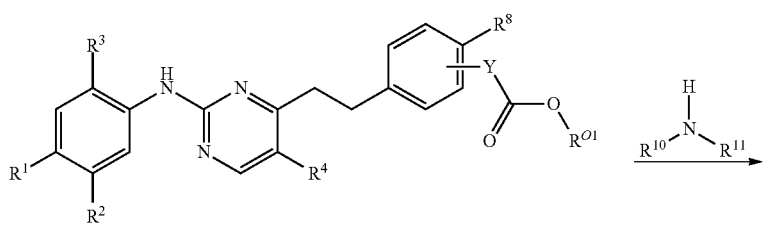

F27

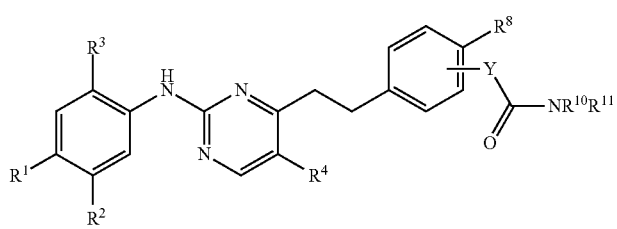

F29

Alternatively, when $R^{O1}$=Me, esters of the formula F27 may be directly converted to amides of the formula F29 by reaction with an amine at elevated temperatures.

Scheme L

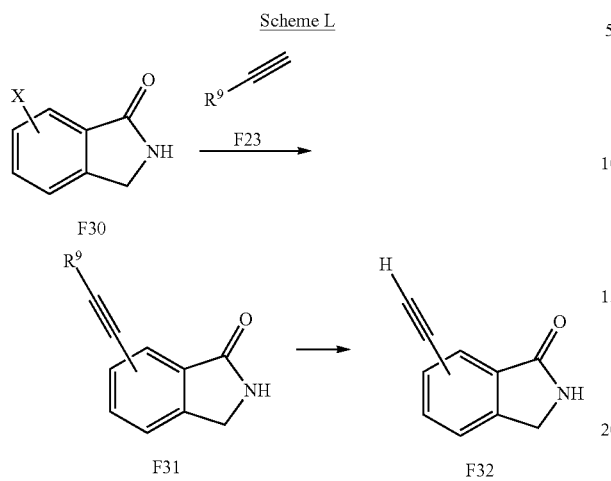

Where molecules with lactams fused to the right hand side aromatic ring are required compounds of the formula F30 can be reacted with terminal acetylenes of the formula F23 in a Sonagashira type coupling to give acetylenes of the formula F31 where $R^9$=TMS, TES or $(CH_3)_2C^*OH$. $R^9$ may then be removed to generate compounds of the formula F32. When $R^9$=TMS or TES, potassium carbonate or tetra-n-butyl ammonium fluoride may be employed to induce this transformation. When $R^9$=$(CH_3)_2C^*OH$, sodium hydride in refluxed toluene may be used.

Compounds of the formula F32 can then be coupled to compounds of the formula F3 and further elaborated as described above and below.

Scheme M

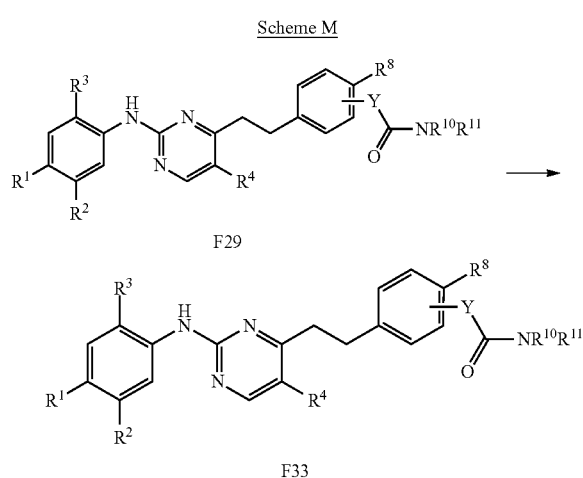

Compounds of the formula F29, or analogues containing lactams, with Boc protecting groups present in $R^1$ or $R^2$ (in the place of $R^{N1}$, $R^{N2}$, $R^{N3}$, $R^{N4}$ and $R^{N5}$) may then be deprotected under acidic conditions, for example using trifluoroacetic acid in dichloromethane solutions, to give the corresponding parent piperazine or piperidine compounds of the formula F33.

Scheme N

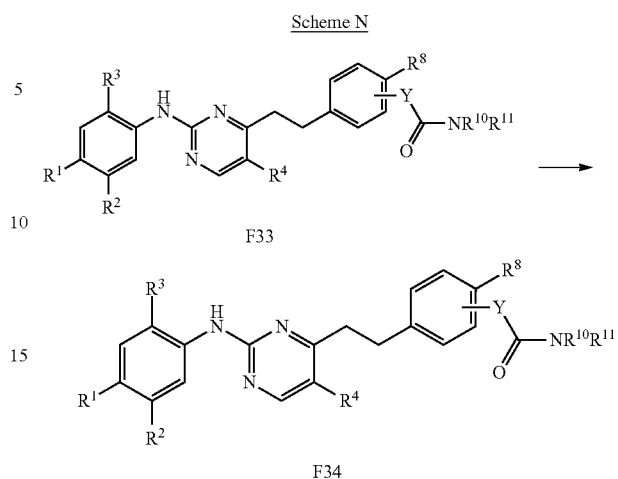

Compounds of the formula F33 may then be further modified by derivitisation of the amine functionality. For example, compounds of the formula F34 where $R^{N1}$, $R^{N2}$, $R^{N3}$, $R^{N4}$, $R^{N5}$ or $R^{N6}$=Me may be prepared by reductive alkylation with formaldehyde in the presence of sodium triacetoxyborohydride. Derivatives were $R^{N1}$, $R^{N2}$, $R^{N3}$, $R^{N5}$ or $R^{N6}$=Et may be prepared by reductive alkylation with acetaldehyde in the presence of sodium triacetoxyborohydride. Compounds of the formula F34 where $R^{N1}$, $R^{N2}$, $R^{N3}$, $R^{N5}$ or $R^{N6}$=acetyl may be prepared by reaction of compounds of the formula F33 with a suitable acylating agent, for example acetic anhydride.

An alternate strategy for the formation of compounds of the formula F27, where $R^3$=$CF_3$ and $R^7$=H, is to prepare compounds of the formula F37, as outlined in scheme N.

Scheme N

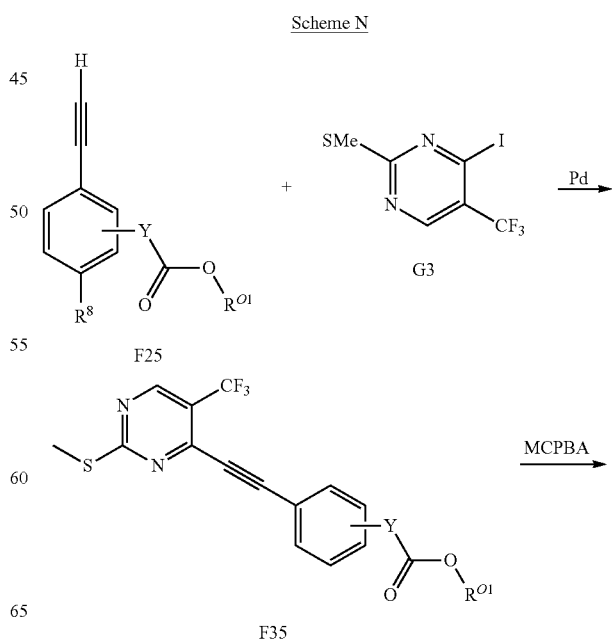

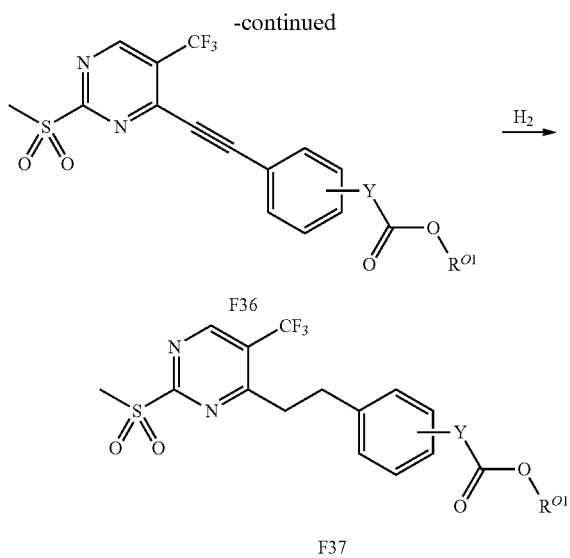

Coupling of esters of the formula F25, where $R^8$=H, with 4-iodo-2-(methylthio)-5-(trifluoromethyl)pyrimidine (G3) under Sonagashira conditions gives acetylenes of the formula F35. Oxidation, using MCPBA, gives sulfones of the formula F36. Reduction of the acetylene using hydrogen, in the presence of a catalyst, for example 10% palladium on charcoal, gives compounds of the formula F37.

Compounds of the formla F37 can be reacted with anilines of the formula F2 under acidic conditions, for example in the presence of trifluoro acetic acid to give compounds of the formula F27 which can then be further elaborated as described above.

Use of Compounds of the Invention

The present invention provides active compounds, specifically, active 2,4,5-substituted pyrimidines.

The term "active", as used herein, pertains to compounds which are capable of inhibiting FAK activity, and specifically includes both compounds with intrinsic activity (drugs) as well as prodrugs of such compounds, which prodrugs may themselves exhibit little or no intrinsic activity.

Assays which may be used in order to assess the FAK inhibition offered by a particular compound are described in the examples below.

The present invention further provides a method of inhibiting FAK inhibition in a cell, comprising contacting said cell with an effective amount of an active compound, preferably in the form of a pharmaceutically acceptable composition. Such a method may be practised in vitro or in vivo.

The present invention further provides active compounds which inhibit FAK activity as well as methods of methods of inhibiting FAK activity comprising contacting a cell with an effective amount of an active compound, whether in vitro or in vivo.

Active compounds may also be used as part of an in vitro assay, for example, in order to determine whether a candidate host is likely to benefit from treatment with the compound in question.

The invention further provides active compounds for use in a method of treatment of the human or animal body. Such a method may comprise administering to such a subject a therapeutically-effective amount of an active compound, preferably in the form of a pharmaceutical composition.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "therapeutically-effective amount" as used herein, pertains to that amount of an active compound, or a material, composition or dosage from comprising an active compound, which is effective for producing some desired therapeutic effect, commensurate with a reasonable benefit/risk ratio.

Cancer

The present invention provides active compounds which are anticancer agents. One of ordinary skill in the art is readily able to determine whether or not a candidate compound treats a cancerous condition for any particular cell type, either alone or in combination.

Examples of cancers include, but are not limited to, bone cancer, brain stem glioma, breast Cancer, cancer of the adrenal gland, cancer of the anal region, cancer of the bladder cancer of the endocrine system, cancer of the oesophagus, cancer of the head or neck, cancer of the kidney or ureter, cancer of the liver, cancer of the parathyroid gland, cancer of the penis, cancer of the small intestine, cancer of the thyroid gland, cancer of the urethra, carcinoma of the cervix, carcinoma of the endometrium, carcinoma of the fallopian tubes, carcinoma of the renal pelvis, carcinoma of the vagina, carcinoma of the vulva, chronic or acute leukemia, colon cancer, cutaneous or intraocular melanoma, haemetological malignancies, Hodgkin's disease, lung cancer, lymphocytic lymphomas, neoplasms of the central nervous system (CNS), ovarian cancer, pancreatic cancer, pituitary adenoma, primary CNS lymphoma, prostate cancer, rectal cancer, renal cell carcinoma, sarcoma of soft tissue, skin cancer, spinal axis tumors, stomach cancer and uterine cancer.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

The anti cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and docetaxel (Taxotere) and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661 and 4-((2,4-dichloro-5-methoxyphenyl)amino)-6-methoxy-7-(3-(4-methylpiperazin-1-yl)propoxy)quinoline-3-carbonitrile (bosutinib, SKI-606; Cancer research (2003), 63(2), 375-81), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (Cl 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti vascular endothelial cell growth factor antibody bevacizumab (AvastinT) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-yl-propoxy)quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies A combination of particular interest is with docetaxel. Other possible combinations of interest include with gemcitabine, cisplatin and the camptothecin prodrug irinotecan.

Further combinations of interest include compounds of the invention, in particular, compound 3, with anti-invasion agents, such as c-Src kinase family inhibitors. Of these inhibitors, combination with dasatinib may be preferred. These combinations may be of particular use in treating basal type breast cancers including triple-negative breast cancers, prostate cancer and or other cancers in which overactivation of FAK and/or Src pathway signaling has been implicated in maintenance and progression of the malignant phenotype.

Further combinations of interest include compounds of the invention, in particular, compound 3, with antiangiogenic agents, such as VEGF receptor tyrosine kinase inhibitors or therapeutic antibodies against vascular endothelial growth factors (VEGFs), for example VEGFA, VEGFC or VEGFD. Of these inhibitors and antibodies, combination with bevacizumab may be preferred. These combinations may be of particular use in treating breast cancer, prostate cancer, ovarian caner, renal cancer, glioblastoma, neuroblastoma, medulloblastoma, colon carcinoma, non-small cell lung cancer, mesothelioma and other cancers in which over-expression of VEGFA or over-activation of VEGFR2 or over-expression of VEGFC/D or over-activation of VEGFR3 has been implicated in maintenance and progression of the malignant phenotype.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences*, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powderscapsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabillser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-Isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 μg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

The following are examples are provided solely to illustrate the present invention and are not intended to limit the scope of the invention, as described herein.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et20), acetic acid (AcOH), dichloromethane (methylene chloride, DCM), trifluoroacetic acid (TFA), dimethylformamide (DMF), tetrahydrofuran (THF), dimethylsulfoxide (DMSO), meta-chloroperoxybenzoic acid (mCPBA), tert-butyloxycarbonyl (Boc), trimethylsilyl (TMS), triethylsilyl (TES), 2-(1H-7-azabenzotriazol-1-yl)-1,1,3,3-tetramethyluronium hexafluorophosphate (HATU), diphenylphosphoryl azide (DPPA), 1,8-diazabicyclo[5.4.0]undec-7-ene (DBU), 1-ethyl-3-(3-dimethylaminopropyl) carbodiimide (EDCl), 4-dimethylaminopyridine (DMAP), tetra-n-butylammonium fluoride (TBAF), N,N-Diisopropylethylamine (DIPEA), 1-hydroxybenzotriazole (HOBt), and 1,2-dichloroethene (DCE).

General Experimental Details

Unless otherwise stated the following generalisations apply.

[1]NMR spectra were recorded on either a Bruker Avance DRX300 (300 MHz), a Bruker Ultrasheild plus (400 MHz) or a Varian Unity Inova 600 (600 MHz) spectrometer. The multiplicity of a signal is designated by the following abbreviations: s, singlet; d, doublet; t, triplet; q, quartet; br, broad; m, multiplet. All observed coupling constants, J, are reported in Hertz. $^{13}$C NMR were recorded on a Bruker Avance DRX300 (75 MHz), a Bruker Ultrasheild plus (100 MHz) or a Varian Unity Inova 600 (150 MHz) spectrometer in a broad band decoupled mode.

LC/MS data was generated using either a Finnigan LCQ Advantage Max (LCMS-A), a Waters ZQ 3100 system (LCMS-B) or an Agilent 6100 Series Single Quad LC/MS (LCMS-C).
LCMS Method A (LCMS-A)
Instrument: Finnigan LCQ Advantage Max
Pump: Finnigan Surveyor LC Pump
Finnigan Surveyor Autosampler
Finnigan Surveyor PDA Detector
LC conditions:
Reverse Phase HPLC analysis
Column: Gemini 3µ C18 20×4.0 mm 110A
Injection Volume 10 µL
Solvent A: Water 0.1% Formic Acid
Solvent B: Acetonitrile 0.1% Formic Acid
Gradient: 10-100% B over 10 min
Detection: 100-600 nm
MS conditions:
Ion Source: Ion trap
Ion Mode: ES positive
Temp: 300° C.
Capillary V—25
Detection: Ion counting
Scan Range: 80-1000 A mu
Scan Time: 0.2 sec
Acquisition time: 10 min
LCMS Method B (LCMS-B)
Instrument: Waters ZQ 3100-Mass Detector
Waters 2545-Pump
Waters SFO System Fluidics Organizer
Waters 2996 Diode Array Detector
Waters 2767 Sample Manager
LC conditions:
Reverse Phase HPLC analysis
Column: XBridge TM C18 5 µm 4.6×100 mm
Injection Volume 10 µL
Solvent A: Water 0.1% Formic Acid
Solvent B: Acetonitrile 0.1% Formic Acid
Gradient: 10-100% B over 10 min
Flow rate: 1.5 mL/min
Detection: 100-600 nm
MS conditions:
Ion Source Single-quadrupole
Ion Mode: ES positive
Source Temp: 150° C.
Desolvation Temp: 350° C.
Detection: Ion counting
Cpillary (KV)—3.00
Cone (V): 30
Extractor (V): 3
RF Lens (V): 0.1
Scan Range: 100-1000 Amu
Scan Time: 0.5 sec
Acquisition time: 10 min
Gas Flow
Desolvation L/hr–650
LCMS Method C (LCMS-C)
Instrument: Agilent 6100 Series Single Quad LC/MS
Agilent 1200 Series HPLC
Pump: 1200 Series G1311A Quaternary pump
Autosampler: 1200 Series G1329A Thermostatted Autosampler
Detector: 1200 Series G1314B Variable Wavelength Detector LC conditions:
Reverse Phase HPLC analysis
Column: Luna C8(2) 5µ 50×4.6 mm 100 A
Column temperature: 30° C.
Injection Volume: 5 µL
Solvent A: Water 0.1% Formic Acid
Solvent B: Acetonitrile 0.1% Formic Acid
Gradient: 5-100% B over 10 min
Detection: 254 nm or 214 nm
MS conditions:
Ion Source: Quadrupole
Ion Mode Multimode-ES
Drying gas temp: 300° C.
Vaporizer temperature: 200° C.
Capillary voltage (V): 2000 (positive)
Capillary voltage (V): 4000 (negative)
Scan Range: 100-1000
Step size: 0.1 sec
Acquisition time: 10 min Analytical thin-layer chromatography was performed on Merck silica gel 60F254 aluminium-backed plates which were visualised using fluorescence quenching under UV light or acidic anisaldehyde or a basic potassium permanganate dip. Flash chromatography was performed using either a Teledyne Isco CombiFlash Rf purifi-cation system using standard RediSep® cartridges or a Biotage Isolera purification system using either Grace or Biotage silica cartridges.

Where necessary, anhydrous solvents were prepared using a Braun purification system or purchased from Sigma-Aldrich.

Example 1

2-(2-(2-(2-((2-Methoxy-4-(piperazin-1-yl)phenyl) amino)-5-(trifluoromethyl)pyrimidin-4-yl)ethyl)phenyl)acetamide (1)

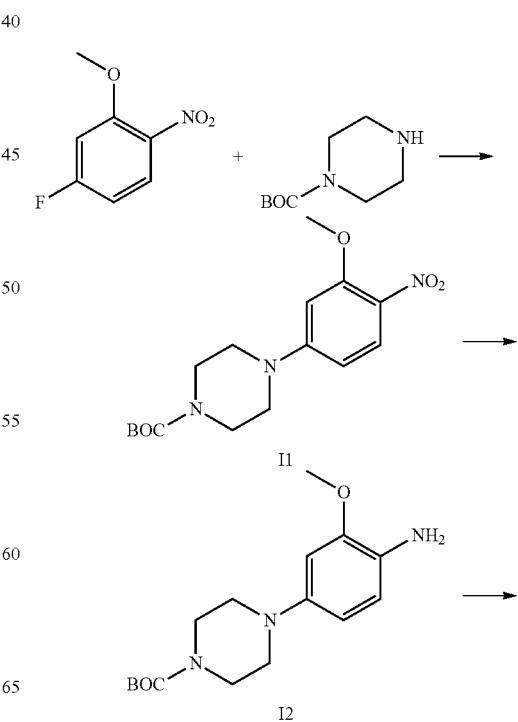

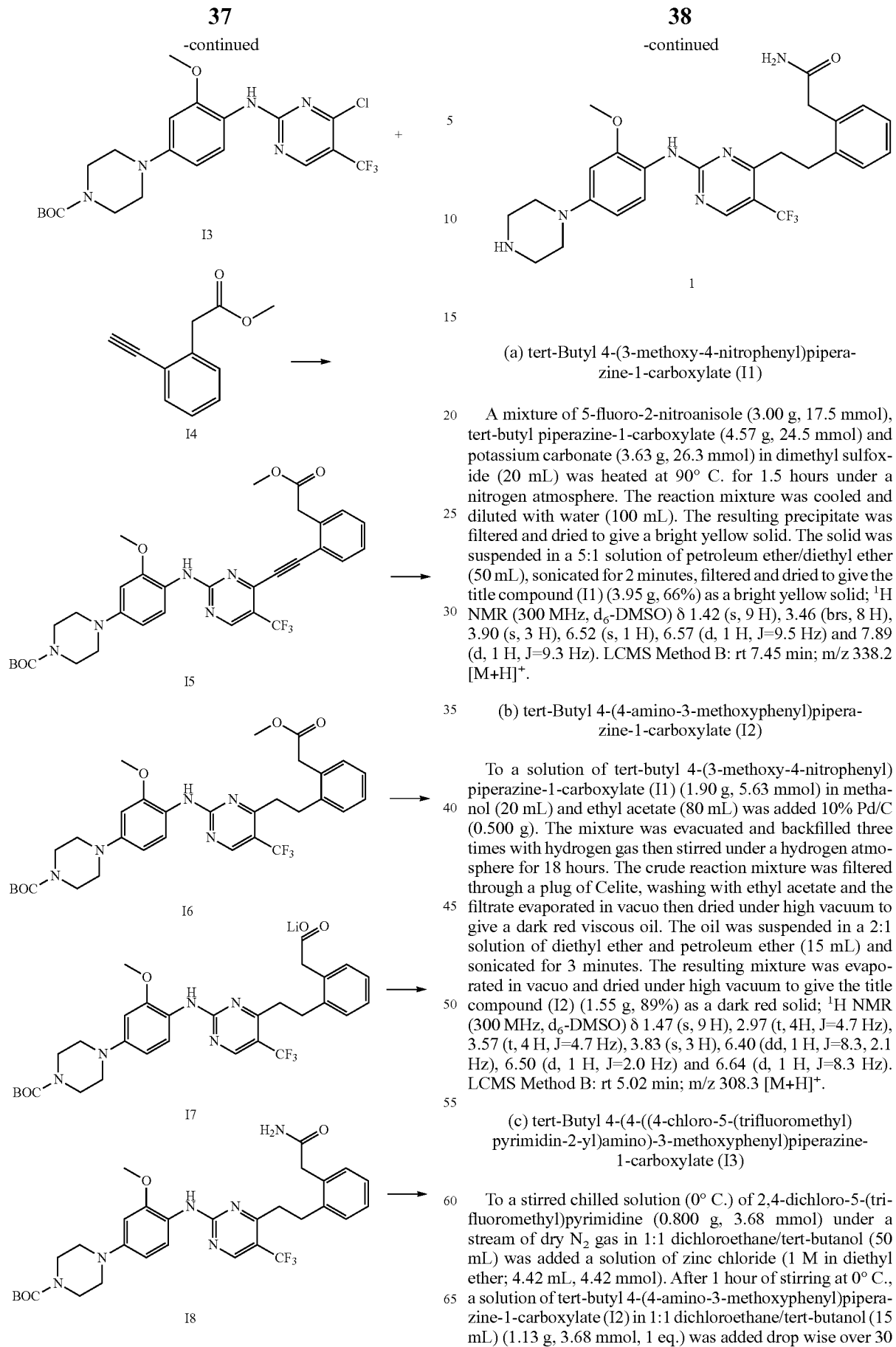

(a) tert-Butyl 4-(3-methoxy-4-nitrophenyl)piperazine-1-carboxylate (I1)

A mixture of 5-fluoro-2-nitroanisole (3.00 g, 17.5 mmol), tert-butyl piperazine-1-carboxylate (4.57 g, 24.5 mmol) and potassium carbonate (3.63 g, 26.3 mmol) in dimethyl sulfoxide (20 mL) was heated at 90° C. for 1.5 hours under a nitrogen atmosphere. The reaction mixture was cooled and diluted with water (100 mL). The resulting precipitate was filtered and dried to give a bright yellow solid. The solid was suspended in a 5:1 solution of petroleum ether/diethyl ether (50 mL), sonicated for 2 minutes, filtered and dried to give the title compound (I1) (3.95 g, 66%) as a bright yellow solid; $^1$H NMR (300 MHz, d$_6$-DMSO) δ 1.42 (s, 9 H), 3.46 (brs, 8 H), 3.90 (s, 3 H), 6.52 (s, 1 H), 6.57 (d, 1 H, J=9.5 Hz) and 7.89 (d, 1 H, J=9.3 Hz). LCMS Method B: rt 7.45 min; m/z 338.2 [M+H]$^+$.

(b) tert-Butyl 4-(4-amino-3-methoxyphenyl)piperazine-1-carboxylate (I2)

To a solution of tert-butyl 4-(3-methoxy-4-nitrophenyl)piperazine-1-carboxylate (I1) (1.90 g, 5.63 mmol) in methanol (20 mL) and ethyl acetate (80 mL) was added 10% Pd/C (0.500 g). The mixture was evacuated and backfilled three times with hydrogen gas then stirred under a hydrogen atmosphere for 18 hours. The crude reaction mixture was filtered through a plug of Celite, washing with ethyl acetate and the filtrate evaporated in vacuo then dried under high vacuum to give a dark red viscous oil. The oil was suspended in a 2:1 solution of diethyl ether and petroleum ether (15 mL) and sonicated for 3 minutes. The resulting mixture was evaporated in vacuo and dried under high vacuum to give the title compound (I2) (1.55 g, 89%) as a dark red solid; $^1$H NMR (300 MHz, d$_6$-DMSO) δ 1.47 (s, 9 H), 2.97 (t, 4H, J=4.7 Hz), 3.57 (t, 4 H, J=4.7 Hz), 3.83 (s, 3 H), 6.40 (dd, 1 H, J=8.3, 2.1 Hz), 6.50 (d, 1 H, J=2.0 Hz) and 6.64 (d, 1 H, J=8.3 Hz). LCMS Method B: rt 5.02 min; m/z 308.3 [M+H]$^+$.

(c) tert-Butyl 4-(4-((4-chloro-5-(trifluoromethyl)pyrimidin-2-yl)amino)-3-methoxyphenyl)piperazine-1-carboxylate (I3)

To a stirred chilled solution (0° C.) of 2,4-dichloro-5-(trifluoromethyl)pyrimidine (0.800 g, 3.68 mmol) under a stream of dry N$_2$ gas in 1:1 dichloroethane/tert-butanol (50 mL) was added a solution of zinc chloride (1 M in diethyl ether; 4.42 mL, 4.42 mmol). After 1 hour of stirring at 0° C., a solution of tert-butyl 4-(4-amino-3-methoxyphenyl)piperazine-1-carboxylate (I2) in 1:1 dichloroethane/tert-butanol (15 mL) (1.13 g, 3.68 mmol, 1 eq.) was added drop wise over 30 minutes followed by the drop wise addition of a solution of triethylamine (0.565 mL, 0.410 mmol, 1.1 eq.) in 1:1 dichloroethane/tert-butanol (5 mL) over 30 minutes. The resulting mixture was then stirred vigorously at room temperature for 18 hours. The volatiles were evaporated under reduced pressure and the residue then dried under high vacuum. Ethyl acetate and water were added and the aqueous layer was extracted with ethyl acetate (3×30 mL). The combined organic extracts were washed with water, brine, dried (magnesium sulfate), filtered and evaporated to give the crude product as a dark yellow foam. The crude product was purified by flash column chromatography on silica gel (0-20% ethyl acetate/petroleum ether) to yield the title compound (I3) (1.25 g, 69%) as a yellow solid; $^1$H NMR (300 MHz, CDCl$_3$) δ 1.48 (s, 9 H), 3.11 (t, 4 H, J=5.2 Hz), 3.59 (t, 4 H, J=5.0 Hz), 3.88 (s, 3 H), 6.54 (s, 1 H), 6.57 (d, 1 H, J=9.4 Hz), 7.83 (s, 1 H), 8.17 (d, 1 H, J=8.5 Hz) and 8.53 (s, 1 H). LCMS Method B: rt 9.24 min; m/z 488.3 [M+H]$^+$.

(d) tert-Butyl 4-(3-methoxy-4-((4-((2-(2-methoxy-2-oxoethyl)phenyl)ethynyl)-5-(trifluoromethyl)pyrimidin-2-yl)amino)phenyl)piperazine-1-carboxylate (I5)

To a solution of tert-butyl 4-(4-((4-chloro-5-(trifluoromethyl)pyrimidin-2-yl)amino)-3-methoxyphenyl)piperazine-1-carboxylate (I72) (0.350 g, 0.717 mmol) in dimethylformamide (2.5 mL) and triethylamine (0.450 mL) was added methyl 2-(2-ethynylphenyl)acetate (I4: prepared according to the procedure of Peng, C. et al.; *Adv. Synth. Catal.* 2008, 350, 2359-2364 or as described below) (0.137 g, 0.789 mmol), trans-dichlorobis(triphenylphosphine) palladium(II) (0.025 g, 0.036 mmol), CuI (0.014 g, 0.072 mmol) and triphenylphosphine (0.019 g, 0.072 mmol). The reaction mixture was heated under microwave irradiation at 120° C. whilst stirring for 15 minutes. The reaction mixture was diluted with ethyl acetate and water then the resulting mixture was extracted with ethyl acetate (3×15 mL). The combined organic extracts were washed with water, brine, dried (magnesium sulfate), filtered and evaporated to give a brown solid. The solid was purified by flash column chromatography on silica gel (10-50% ethyl acetate/petroleum ether) to give the title compound (I5) (0.360 g, 80%) as an orange crystalline solid; $^1$H NMR (300 MHz, CDCl$_3$) δ 1.49 (s, 9 H), 3.11 (s, 4 H), 3.60 (s, 4 H), 3.71 (d, 3 H, J=1.0 Hz), 3.89 (s, 3H), 3.96 (s, 2 H), 6.55 (s, 1 H), 6.59 (s, 1 H), 7.26-7.45 (m, 3 H), 7.68 (d, 1 H, J=7.6 Hz), 7.83 (s, 1 H), 8.27 (d, 1 H, J=7.3 Hz), and 8.60 (s, 1 H). LCMS Method B: rt 9.55 min; m/z 626.4 [M+H]$^+$.

(e) tert-Butyl 4-(3-methoxy-4-((4-(2-(2-methoxy-2-oxoethyl)phenethyl)-5-(trifluoromethyl)pyrimidin-2-yl)amino)phenyl)piperazine-1-carboxylate (I6)

To a solution of tert-butyl 4-(3-methoxy-4-((4-((2-(2-methoxy-2-oxoethyl)phenyl)ethynyl)-5-(trifluoromethyl) pyrimidin-2-yl)amino)phenyl)piperazine-1-carboxylate (I5) (0.358 g, 0.572 mmol) in ethyl acetate (25 mL) and dimethylformamide (5 mL) was added 10% Pd/C (0.200 g). The mixture was evacuated and backfilled three times with hydrogen gas then stirred under a hydrogen atmosphere for 18 hours. The reaction mixture was filtered through a plug of Celite, washing with ethyl acetate then the filtrate was evaporated in vacuo and dried under high vacuum to give the title compound (I6) (0.360 g, 100%) as a viscous yellow oil; $^1$H NMR (300 MHz, CDCl$_3$) δ 1.48 (s, 9 H), 3.00-3.20 (m, 8 H), 3.59 (t, 4 H, J=4.8 Hz), 3.67 (s, 3 H), 3.75 (s, 2 H), 3.90 (s, 3 H), 6.55-6.57 (m, 2 H), 7.19-7.26 (m, 4 H), 7.75 (s, 1 H), 8.26 (d, 1 H, J=9.4 Hz) and 8.50 (s, 1 H). LCMS Method B: rt 6.55 min; m/z 630.5 [M+H]$^+$.

(f) Lithium 2-(2-(2-(2-((4-(4-(4-(tert-butoxycarbonyl)piperazin-1-yl-2-methoxyphenyl)amino)-5-(trifluoromethyl)pyrimidin-4-yl)ethyl)phenyl)acetate (I7)

To a solution of tert-butyl 4-(3-methoxy-4-((4-(2-(2-methoxy-2-oxoethyl)phenethyl)-5-(trifluoromethyl)pyrimidin-2-yl)amino)phenyl)piperazine-1-carboxylate (I6) (0.360 g, 0.572 mmol) in tetrahydrofuran (17 mL), methanol (3 mL) and water (5 mL) was added lithium hydroxide (0.042 g, 1.77 mmol) and the resulting mixture was stirred at room temperature for 20 hours. The reaction volatiles were evaporated in vacuo and the resulting residue was diluted with ethyl acetate and saturated aqueous sodium hydrogen carbonate. The aqueous phase was extracted with ethyl acetate (3×20 mL) and the combined organic extracts were washed with saturated aqueous sodium hydrogen carbonate (20 mL), dried (magnesium sulfate), filtered, evaporated in vacuo and dried to give the title compound (I7) (0.356 g, 100%) as a yellow foam; $^1$H NMR (300 MHz, CDCl$_3$) δ 1.48 (s, 9 H), 2.96-3.06 (m, 8 H) 3.56-3.62 (m, 6 H), 3.77 (s, 3 H), 6.47-6.51 (m, 2 H), 7.00-7.11 (m, 2H), 8.00 (brs, 2 H) and 8.43 (s, 1 H). LCMS Method B: rt 9.00 min; m/z 616.4 [M+H]$^+$.

(g) tert-Butyl 4-(4-((4-(2-(2-amino-2-oxoethyl)phenethyl)-5-(trifluoromethyl)pyrimidin-2-yl-amino)-3-methoxyphenyl)piperazine-1-carboxylate (I8)

To a stirred solution of lithium 2-(2-(2-(2-((4-(4-(tert-butoxycarbonyl)piperazin-1-yl)-2-methoxyphenyl)amino)-5-(trifluoromethyl)pyrimidin-4-yl)ethyl)phenyl)acetate (I7) (0.352 g, 0.672 mmol), 1-hydroxybenzotriazole (0.093 g, 0.686 mmol) and 1-ethyl-3-(3-dimethylaminopropyl)carbodiimide) hydrochloride (0.121 g, 0.629 mmol) in dry tetrahydrofuran (16 mL) and dimethylformamide (7 mL) was added N,N-diisopropylethylamine (0.498 mL, 2.86 mmol) under a nitrogen atmosphere. The reaction mixture was stirred for 10 minutes at room temperature then ammonium carbonate (0.263 g, 2.859 mmol) was added and the resulting suspension was stirred at room temperature for 18 hours. The reaction volatiles were evaporated in vacuo and the resulting residue was diluted with ethyl acetate (15 mL) and water (10 mL). The layers were separated and the aqueous layer was extracted with ethyl acetate (2×15 mL). The combined organic extracts were washed with water, brine, dried (magnesium sulfate) and concentrated in vacuo to give a yellow foam which was purified by flash column chromatography on silica gel (55-85% ethyl acetate/petroleum ether) to give the title compound (I8) (0.276 g, 87%) as a yellow foam; $^1$H NMR (300 MHz, CDCl$_3$) δ 1.48 (d, 9 H, J=1.1 Hz), 3.09 (d, 8 H, J=3.9 Hz), 3.58 (brs, 4 H), 3.66 (s, 2 H), 3.88 (d, 3 H, J=1.0 Hz), 5.48 (brs, 1 H), 5.78 (brs, 1 H), 6.54 (d, 1 H, J=1.3 Hz), 6.57 (s, 1 H), 7.23-7.25 (brs, 4 H), 7.72 (s, 1 H), 8.13 (d, 1 H, J=8.6 Hz) and 8.48 (s, 1 H). LCMS Method B: rt 8.52 min; m/z 615.4 [M+H]$^+$.

(f) 2-(2-(2-(2-((2-methoxy-4-(piperazin-1-yl)phenyl)amino)-5-(trifluoromethyl)pyrimidin-4-yl)ethyl)phenyl)acetamide (1)

To a solution of tert-butyl 4-(4-((4-(2-(2-amino-2-oxoethyl)phenethyl)-5-(trifluoromethyl)pyrimidin-2-yl)amino)-3-methoxyphenyl)piperazine-1-carboxylate (I8) (0.276 g, 0.449 mmol) in dichloromethane (8 mL), was added trifluoroacetic acid (0.669 mL, 8.98 mmol) and the resulting mixture was stirred under a nitrogen atmosphere for 18 hours. The solvents were evaporated in vacuo to give a yellow residue which was dissolved in 3:1 chloroform/2-propanol and 1 M aqueous sodium hydroxide solution. The aqueous layer was extracted with 3:1 chloroform/2-propanol (3×15 mL) and the combined organic extracts were washed with water, brine, dried (magnesium sulfate), filtered and evaporated to give the title compound (1) (0.229 g, 99%) as a yellow foam; $^1$H NMR (300 MHz, d$_6$-DMSO) δ 2.87-3.10 (m, 12 H), 3.46 (s, 2 H), 3.78 (s, 3 H), 4.32 (d, 1 H, J=4.2 Hz), 6.48 (dd, 1 H, J=2.2, 8.7 Hz), 6.61 (d, 1 H, J=2.1 Hz), 6.88 (brs, 1 H), 7.15-7.30 (m, 4 H), 7.38 (brs, 1 H), 7.46 (brs, 1 H), 8.51 (s, 1 H) and 8.81 (s, 1 H). LCMS Method B: rt 5.65 min; m/z 515.4 [M+H]$^+$.

Synthesis of Intermediate I4: Methyl 2-(2-Ethynylphenyl)acetate (I4)

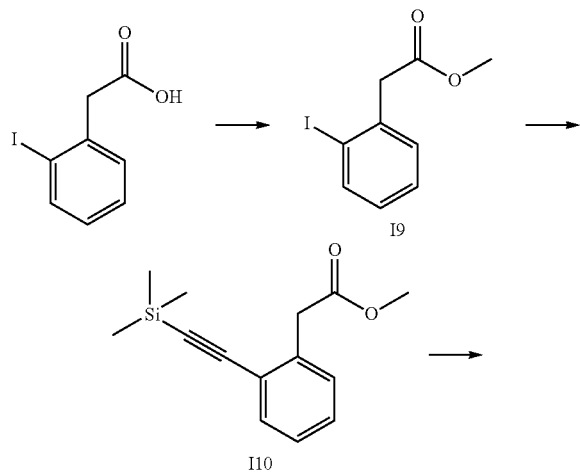

(a) Methyl 2-(2-iodophenyl)acetate (I9)

2-(2-Iodophenyl)acetic acid (5.00 g, 19.1 mmol) was placed into a reaction flask and dissolved in MeOH (150 mL). Sulfuric acid (250 µL) was added and reaction mixture was stirred and heated at 80° C. under nitrogen for 16 hours. The resulting mixture was cooled to room temperature and the volatiles removed by evaporation under reduced pressure. The residue was taken up in ethyl acetate (100 mL), washed with 10% NaHCO$_3$ (100 mL), dried (MgSO$_4$) and evaporated under reduced pressure to give the title compound (I9) (5.20 g, 99%) as a clear liquid; $^1$H NMR (400 MHz, CDCl$_3$) δ 7.85 (dd, J=7.9, 1.0 Hz, 1H), 7.35-7.27 (m, 2H), 6.97 (ddd, J=7.9, 7.0, 2.1 Hz, 1H), 3.81 (s, 2H), 3.72 (s, 3H).

(b) Methyl 2-(2-((trimethylsilyl)ethynyl)phenyl)acetate (I10)

Methyl 2-(2-iodophenyl)acetate (I9) (4.65 g, 16.8 mmol), PdCl$_2$(PPh$_3$)$_2$ (295 mg, 421 µmol) and Cu(I)I (80.0 mg, 421 µmol) were placed into an oven dried reaction flask under nitrogen. (Trimethylsilyl)acetylene (2.80 mL, 20:2 mmol), dry degassed THF (20 mL) and triethylamine (20 mL) were added and the reaction mixture was stirred at room temperature for 16 hours. The volatiles were removed under reduced pressure to give a black residue which was adsorbed onto silica then chromatographed on silica gel (0-5% ethyl acetate/petroleum benzine 40-60° C.) to give the title compound (I10) (4.63 g, 99%) as a light brown liquid; $^1$H NMR (400 MHz, CDCl$_3$) δ 7.48 (dd, J=7.5, 0.8 Hz, 1H), 7.32-7.14 (m, 3H), 3.84 (s, 2H), 3.71 (s, 3H), 0.26 (s, 9H). LCMS Method C: rt 6.64 min.

(c) Methyl 2-(2-ethynylphenyl)acetate (I4)

Methyl 2-(2-((trimethylsilyl)ethynyl)phenyl)acetate (I10) (4.63 g, 19.0 mmol) was dissolved in DCM (200 mL) and TBAF (1.0 M in THF) (28.5 mL, 28.5 mmol, 1.5 eq) was added at 0° C. The resulting solution was stirred at room temperature for 1 hour before washing with 10% NaHCO$_3$ (100 mL). The organic layer was dried (MgSO$_4$) then evaporated under reduced pressure to give a dark brown/black residue. The residue was adsorbed onto silica and then chromatographed on silica gel (0-10% ethyl acetate/petroleum benzine 40-60° C.) to give the title compound (I4) (2.76 g, 83%) as a red liquid; $^1$H NMR (400 MHz, CDCl$_3$) δ 7.52 (dd, J=7.6, 1.1 Hz, 1H), 7.43-7.16 (m, 3H), 3.88 (d, J=9.6 Hz, 2H), 3.77-3.52 (m, 3H), 3.28 (s, 1H).

Synthesis of Intermediate I15: Methyl 2-(2-(2-(2-(methylsulfonyl)-5-(trifluoromethyl)pyrimidin-4-yl)ethyl)phenyl)acetate (I15)

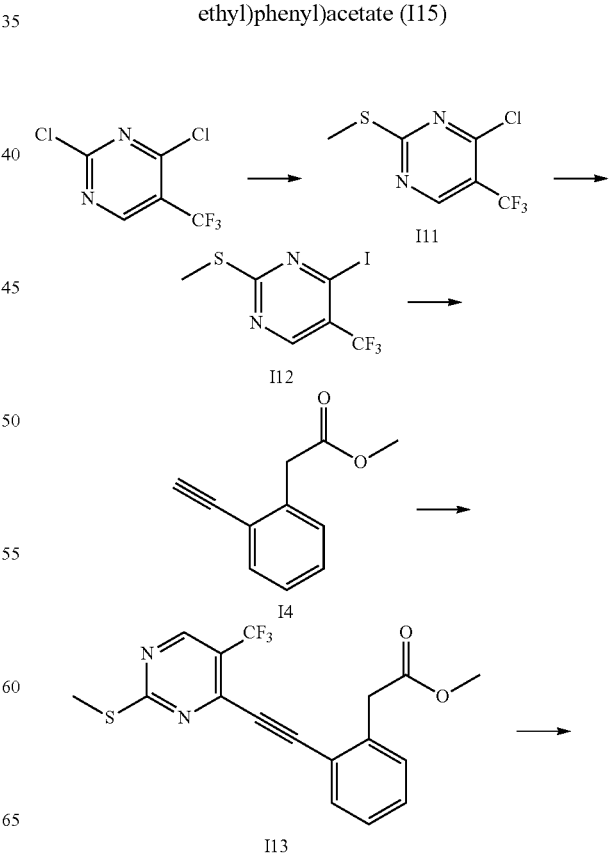

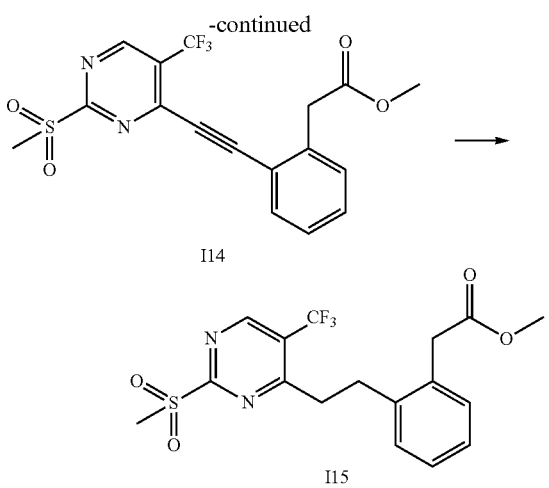

(a) 4-Chloro-2-(methylthio)-5-(trifluoromethyl)pyrimidine (I11)

To a solution of the 2,4-dichloro-5-(trifluoromethyl)pyrimidine (2.50 g, 11.5 mmol) in THF (50 mL) in an ice bath under nitrogen was added zinc(II) chloride (1.0 M in ether, 13.8 mL, 13.8 mmol) dropwise. The mixture was stirred in the ice bath for two hours, then sodium methanethiolate (0.888 g, 12.7 mmol) was added. The mixture was stirred overnight, allowing the reaction to slowly come to room temperature. After 18 hours the reaction was quenched with 2 M HCl (15 mL), and the organics removed by evaporation under reduced pressure. The aqueous residue was diluted with brine (15 mL), and extracted with DCM (3×30 mL). The combined organic phases were dried (phase separator) and carefully evaporated to give a pale yellow oil. Chromatography (2×40 g silica cartridge, 0-20% DCM/n-hexane) followed by carefully evaporation of solvent (40° C. @ 400 mmHg then room temperature @ 200 mmHg) gave the title compound (I11) (2.149 g, 82% yield) as a colourless oil; $^1$H NMR (600 MHz, CDCl$_3$) δ 8.66 (s, 1H), 2.61 (s, 3H). LCMS Method C: rt: 7.95 min; m/z 229.1[M+H]$^+$. Note: I11 is volatile.

(b) 4-Iodo-2-(methylthio)-5-(trifluoromethyl)pyrimidine (I12)

4-Chloro-2-(methylthio)-5-(trifluoromethyl)pyrimidine (I11) (5.00 g, 21.9 mmol) was placed into a reaction flask then sodium iodide (9.80 g, 65.6 mmol) and hydroiodic acid (58%) (70 mL) were added. The reaction mixture was stirred for 48 hours in darkness then diluted with water (200 mL) where upon a colourless solid precipitated. The precipitate was collected by filtration and was washed with 10% NaHCO$_3$ solution until neutral. The resulting solid was washed with water (100 mL) then suction dried for 2 hours to give the title compound (I12) (3.956 g, 57%) as a pale yellow solid; $^1$H NMR (400 MHz, CDCl$_3$) δ 8.42 (s, 1H), 2.58 (s, 3H). LCMS Method C: rt 6.30 min; m/z 321.0 [M+H]$^+$.

(c) Methyl 2-(2-((2-(methylthio)-5-(trifluoromethyl) pyrimidin-4-yl)ethynyl)phenyl)acetate (I13)

4-Iodo-2-(methylthio)-5-(trifluoromethyl)pyrimidine (I12) (2.00 g, 6.24 mmol), PdCl$_2$(PPh$_3$)$_2$ (438 mg, 625 µmol), CuI (119 mg, 625 µmol) and triphenylphosphine (164 mg, 625 µmol) were placed into an oven dried microwave reaction vial under nitrogen. Methyl 2-(2-ethynylphenyl)acetate (I4) (1.31 g, 7.49 mmol), THF (20 mL) and triethylamine (10 mL) were added and the resulting mixture was stirred at 100° C. under microwave irradiation for 10 min. The volatiles were evaporated under reduced pressure then the residue was adsorbed onto silica from DCM. The pre-adsorbed material was chromatographed on silica gel (6-25% ethyl acetate/petroleum benzine 40-60° C.) to give the title compound (I13) (1.571 g, 69%) as an orange solid; $^1$H NMR (400 MHz, CDCl$_3$) δ 8.71 (d, J=0.8 Hz, 1H), 7.68 (dd, J=7.7, 1.1 Hz, 1H), 7.50-7.29 (m, 3H), 3.93 (s, 2H), 3.71 (d, J=3.4 Hz, 3H), 2.62 (d, J=3.4 Hz, 3H).

(d) Methyl 2-(2-((2-(methylsulfonyl)-5-(trifluoromethyl)pyrimidin-4-yl)ethynyl)phenyl)acetate (I14)

Methyl 2-(2-((2-(methylthio)-5-(trifluoromethyl)pyrimidin-4-yl)ethynyl)phenyl)acetate (I13) (3.14 g, 8.57 mmol) was dissolved in DCM (150 mL) and the resulting solution cooled to 0° C. mCPBA (70%; 4.65 g, 18.9 mmol) was added then the reaction mixture was allowed to warm to room temperature, at which, stirring was continued overnight. The crude mixture was washed with 10% NaHCO$_3$ (200 mL) and the layers were separated. The organics were dried (MgSO$_4$) then evaporated under reduced pressure to give a light yellow solid. The solid was adsorbed onto silica then chromatographed on silica gel (0-50% ethyl acetate/petroleum benzine 40-60° C.) to give the title compound (I14) (2.876 g, 84%) as a yellow solid; $^1$H NMR (400 MHz, CDCl$_3$) δ 9.13 (d, J=0.7 Hz, 1H), 7.73 (dd, J=7.6, 0.9 Hz, 1H), 7.54-7.46 (m, 1H), 7.44-7.32 (m, 2H), 3.94 (s, 2H), 3.77-3.67 (m, 3H), 3.43 (s, 3H). LCMS Method C: rt 5.90 min; m/z 421.0 (M+Na), 399.1 (M+1), 367.0 (M—OMe), 339.1 (M—COOMe).

(e) Methyl 2-(2-(2-(2-(methylsulfonyl)-5-(trifluoromethyl)pyrimidin-4-yl)ethyl)phenyl)acetate (I15)

Methyl 2-(2-((2-(methylsulfonyl)-5-(trifluoromethyl)pyrimidin-4-yl)ethynyl)phenyl)acetate (I14) (1.50 g, 3.76 mmol) was taken up in DMF (30 mL) then 10% Pd/C (750 mg) was added. The resulting suspension was stirred under H$_2$ (1 atm) for 16 hours at room temperature. The crude reaction mixture was filtered through Celite, washing with MeOH. The filtrate was evaporated under reduced pressure to give a yellow liquid which was adsorbing onto silica. The silica adsorbed material was chromatographed on silica gel (0-100% ethyl acetate/petroleum benzine 40-60° C.) to give the title compound (I15) (1.38 g, 91%) as a yellow solid; $^1$H NMR (400 MHz, CDCl$_3$) δ 9.07 (d, J=0.7 Hz, 1H), 7.30-7.12 (m, 4H), 3.72 (s, 2H), 3.68 (s, 3H), 3.41-3.35 (m, 2H), 3.35 (s, 3H), 3.20 (dd, J=9.6, 6.3 Hz, 2H). LCMS Method C: rt 5.92 min; m/z 425.1 (M+Na), 403.1 (M+1), 401.1 (M−1), 371.1 (M—OMe), 343.1 (M—COOMe).

Example 2
2-(2-(2-(2-((2-Methoxy-4-(piperidin-4-yl)phenyl)amino)-5-(trifluoromethyl)pyrimidin-4-yl)ethyl)phenyl)acetamide (2)
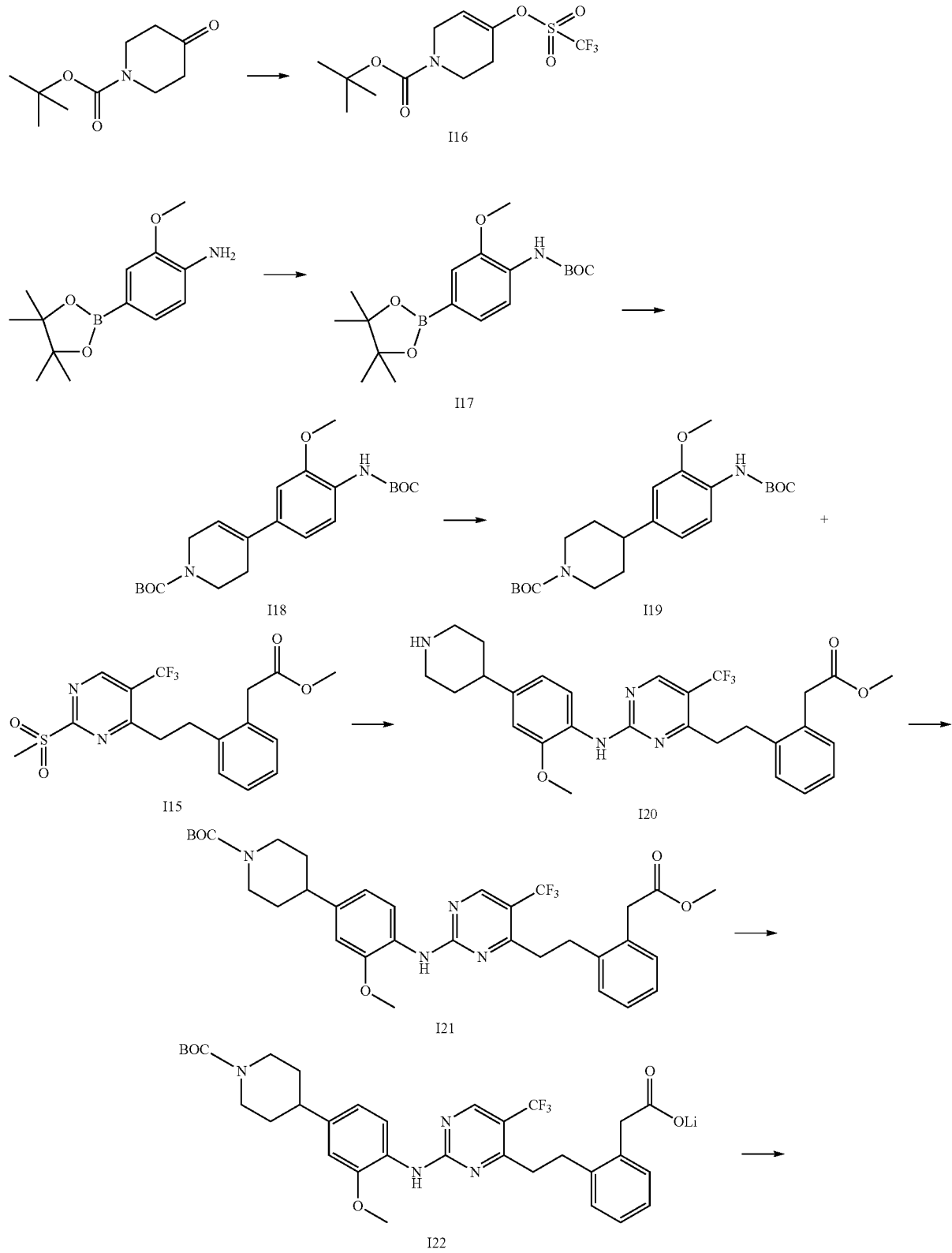

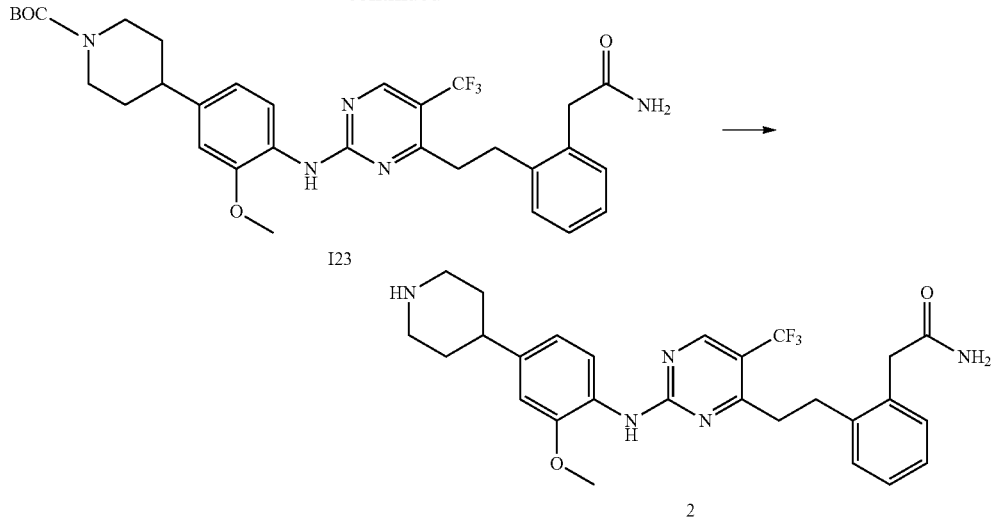

(a) tert-Butyl 4-(((trifluoromethyl)sulfonyl)oxy)-5,6-dihydropyridine-1(2H)-carboxylate (I16)

Lithium diisopropylamide (2 M in heptane/THF/ethylbenzene; 15.1 mL, 30.1 mmol) was added drop wise to a solution of tert-butyl 4-oxopiperidine-1-carboxylate (3.00 g, 15.1 mmol) in THF (50 mL) at −78° C. and the mixture left to stir for 30 minutes. A solution of N-phenyl-bis(trifluoromethanesulfonimide) (6.46 g, 18.1 mmol) in THF (60 mL) was then added dropwise over 30 minutes to the reaction and mixture left to stir for 30 minutes at −78° C. The resulting mixture was then allowed to warm to room temperature and was stirred for 24 hours. The solvent was partially removed (ca 80 mL) and the reaction mixture quenched with saturated NaHCO$_3$ solution (50 mL). DCM (50 mL) was added to the solution and the layers separated. The aqueous layer was then extracted with DCM (2×50 mL). The organic layers were combined and washed with 0.2 M citric acid solution (50 mL), 1 M NaOH (50 mL), brine (50 mL) and dried over Na$_2$SO$_4$. The solvent was removed under reduced pressure to give a brown oil which was purified by column chromatography on silica gel (0-10% diethyl ether in petroleum benzine 40-60° C.) to afford the title compound (I16) (2.48 g, 50%) as an orange oil which crystallized on cooling to −18° C.; $^1$H NMR (400 MHz, CDCl$_3$) δ 5.76 (s, 1H), 4.05-4.04 (m, 2H), 3.63 (t, J=5.6 Hz, 2H), 2.46-2.43 (m, 2H), 1.47 (s, 9H).

(b) tert-Butyl (2-methoxy-4-(4,4,5,5-tetramethyl-1,3,2-dioxaborolan-2-yl)phenyl)carbamate (I17)

2-Methoxy-4-(4,4,5,5-tetramethyl-1,3,2-dioxaborolan-2-yl)aniline (1.00 g, 4.01 mmol), Boc anhydride (1.75 g, 8.02 mmol) and toluene (10 mL) were stirred under nitrogen at 110° C. for 20 hours. The volatiles were evaporated under reduced pressure then the residue adsorbed onto silica gel. Chromatography (SiO$_2$, 0-20% ethyl acetate/petroleum benzine 40-60° C.) gave the title compound (I17) (1.40 g, 100%) as a colourless solid; $^1$H NMR (400 MHz, CDCl$_3$) δ 8.11 (d, J=7.9 Hz, 1H), 7.43 (dd, J=8.0, 0.8 Hz, 1H), 7.26 (dd, J=7.8, 6.9 Hz, 1H), 3.92 (s, 3H), 1.53 (s, 9H), 1.35 (s, 12H). LCMS Method C: rt 6.85 min.

(c) tert-Butyl 4-(4-((tert-butoxycarbonyl)amino)-3-methoxyphenyl)-5,6-dihydropyridine-1(2H)-carboxylate (I18)

To a solution of tert-butyl 4-(((trifluoromethyl)sulfonyl)oxy)-5,6-dihydropyridine-1(2H)-carboxylate (I16) (474 mg, 1.43 mmol), tert-butyl (2-methoxy-4-(4,4,5,5-tetramethyl-1,3,2-dioxaborolan-2-yl)phenyl)carbamate (I17) (500 mg, 1.43 mmol) and Pd(PPh$_3$)4 (165 mg, 0.143 mmol) in DME (15 mL) was added a solution of 3.5 M aqueous NaHCO$_3$ (2.00 mL, 5.0 eq) and the resulting suspension was heated at 80° C. for 16 hours. On cooling to room temperature ethyl acetate (70 mL) was added and the resulting solution was washed with water (50 mL). The organic layer was dried (MgSO$_4$) and evaporated to dryness. The residue was chromatographed (SiO$_2$, 0-20% ethyl acetate/petroleum benzine 40-60° C.) to give the title compound (I18) (520 mg, 90%) as a pale yellow liquid; $^1$H NMR (400 MHz, CDCl$_3$) δ 8.03 (d, J=8.1 Hz, 1H), 7.09 (s, 1H), 6.96 (dd, J=8.4, 1.3 Hz, 1H), 6.88 (d, J=1.7 Hz, 1H), 5.98 (s, 1H), 4.08 (d, J=1.9 Hz, 2H), 3.89 (s, 3H), 3.64 (t, J=5.6 Hz, 2H), 2.52 (s, 2H), 1.54 (s, 9H), 1.51 (s, 9H). LCMS Method C: rt 6.87 min; m/z 349.1 [M-t-Bu+2]$^+$.

(d) tert-Butyl 4-(4-((tert-butoxycarbonyl)amino)-3-methoxyphenyl)piperidine-1-carboxylate (I19)

A suspension of tert-butyl 4-(4-((tert-butoxycarbonyl)amino)-3-methoxyphenyl)-5,6-dihydropyridine-1(2H)-carboxylate (I18) (500 mg, 1.23 mmol) and 10% Pd/C (50 mg) in MeOH (30 mL) was stirred under an atmosphere of hydrogen for 16 hours. The resulting mixture was filtered through celite, washing with ethyl acetate (70 mL) then the filtrate evaporated to dryness. The residue was chromatographed (SiO$_2$, 0-20% ethyl acetate/petroleum benzine 40-60° C.) to give the title compound (I19) (411 mg, 82%) as a pale yellow liquid; $^1$H NMR (400 MHz, CDCl$_3$) δ 7.94 (d, J=7.4 Hz, 1H), 6.99 (s, 1H), 6.76 (d, J=8.3 Hz, 1H), 6.67 (s, 1H), 4.21 (s, 2H), 3.84 (s, 3H), 2.77 (t, J=12.2 Hz, 2H), 2.57 (ddd, J=12.1, 9.0, 3.3 Hz, 1H), 1.79 (d, J=12.6 Hz, 2H), 1.68-1.54 (m, 2H), 1.50 (s, 9H), 1.47 (s, 9H).

(e) Methyl 2-(2-(2-(2-((2-methoxy-4-(piperidin-4-yl)phenyl)amino)-5-(trifluoromethyl)pyrimidin-4-yl)ethyl)phenyl)acetate (I20)

Methyl 2-(2-(2-(2-(methylsulfonyl)-5-(trifluoromethyl)pyrimidin-4-yl)ethyl)phenyl)acetate (I15) (200 mg, 0.497 mmol) and tert-butyl 4-(4-((tert-butoxycarbonyl)amino)-3-methoxyphenyl)piperidine-1-carboxylate (I19) (303 mg, 0.745 mmol) were dissolved in trifluoroethanol (4 mL). Trifluoroacetic acid (200 µL) was added and the resulting mixture was heated at 100° C. under microwave irradiation for 1 hour. The crude reaction mixture was adsorbed onto silica gel and separated by silica gel chromatography (0-20% MeOH/DCM) to give the title compound (I20) (215 mg, 82%) as a light brown liquid; $^1$H NMR (400 MHz, $d_6$-Acetone) δ 8.64 (s, 1H), 8.37 (dd, J=8.3, 3.7 Hz, 1H), 7.29 (ddd, J=13.2, 6.9, 1.7 Hz, 3H), 7.22 (ddd, J=8.9, 6.1, 1.7 Hz, 1H), 7.10 (d, J=1.5 Hz, 1H), 6.97 (dd, J=8.3, 1.5 Hz, 1H), 3.98 (d, J=7.4 Hz, 3H), 3.82 (s, 2H), 3.74-3.60 (m, 5H), 3.27 (t, J=11.7 Hz, 2H), 3.22-3.06 (m, 4H), 3.00 (s, 1H), 2.34-2.17 (m, 2H), 2.12 (dd, J=4.0, 3.5 Hz, 2H), 2.08 (dt, J=6.6, 2.2 Hz, 3H). LCMS Method C: rt 5.23 min; m/z 529.1 [M+1]$^+$.

(f) tert-Butyl 4-(3-methoxy-4-((4-(2-(2-methoxy-2-oxoethyl)phenethyl)-5-(trifluoromethyl)pyrimidin-2-yl)amino)phenyl)piperidine-1-carboxylate (I21)

A solution of methyl 2-(2-(2-(2-((2-methoxy-4-(piperidin-4-yl)phenyl)amino)-5-(trifluoromethyl)pyrimidin-4-yl)ethyl)phenyl)acetate (I20) (300 mg, 0.567 mmol) and Boc anhydride (247 mg, 1.13 mmol) in DCM (10 mL) was stirred at room temperature under nitrogen for 20 hours. The volatiles were evaporated under reduced pressure to give a brown liquid which was adsorbed onto silica gel. Chromatography (SiO$_2$, 0-15% MeOH/DCM) gave the title compound (I21) (210 mg, 59% yield) as a brown liquid; $^1$H NMR (400 MHz, CDCl$_3$) δ 8.56 (s, 1H), 8.40 (d, J=8.3 Hz, 1H), 7.95 (s, 1H), 7.31-7.18 (m, 4H), 6.87 (dd, J=8.4, 1.7 Hz, 1H), 6.79 (d, J=1.7 Hz, 1H), 4.28 (d, J=6.5 Hz, 2H), 3.95 (d, J=4.0 Hz, 3H), 3.78 (s, 2H), 3.70 (s, 3H), 3.26-3.02 (m, 4H), 2.84 (t, J=12.2 Hz, 2H), 2.66 (t, J=3.4 Hz, 1H), 1.87 (d, J=12.7 Hz, 2H), 1.66 (dd, J=12.9, 3.4 Hz, 2H), 1.52 (s, 9H). LCMS Method C: rt 7.24 min; m/z 629.2 [M+1]$^+$, 627.0 [M−1]$^−$.

(g) Lithium 2-(2-(2-(2-((4-(1-(tert-butoxycarbonyl)piperidin-4-yl)-2-methoxyphenyl)amino)-5-(trifluoromethyl)pyrimidin-4-yl)ethyl)phenyl)acetate (I22)

A solution of tert-butyl 4-(3-methoxy-4-((4-(2-(2-methoxy-2-oxoethyl)phenethyl)-5-(trifluoromethyl)pyrimidin-2-yl)amino)phenyl)piperidine-1-carboxylate (I21) (210 mg, 0.334 mmol) and LiOH.H$_2$O (42 mg, 1.0 mmol) in THF (10 mL), water (2 mL) and MeOH (1 mL) was stirred at room temperature for 20 hours. The volatiles were evaporated under reduced pressure to give the title compound (I22) as a light yellow solid, 300 mg, excess mass due to inorganic salts present. LCMS Method C: rt 7.31 min; m/z 615.1 [M+1]$^+$, 613.2 [M−1]$^−$.

(h) tert-Butyl 4-(4-((4-(2-(2-amino-2-oxoethyl)phenethyl)-5-(trifluoromethyl)pyrimidin-2-yl)amino)-3-methoxyphenyl)piperidine-1-carboxylate (I23)

A solution of lithium 2-(2-(2-(2-((4-(1-(tert-butoxycarbonyl)piperidin-4-yl)-2-methoxyphenyl)amino)-5-(trifluoromethyl)pyrimidin-4-yl)ethyl)phenyl)acetate (I22) (210 mg, 0.338 mmol), HATU (257 mg, 0.676 mmol), ammonium chloride (362 mg, 6.76 mmol) and DIPEA (115 µL) in dry DMF (4 mL) was stirred at room temperature overnight. The volatiles were evaporated under reduced pressure and the residue diluted with ethyl acetate. The resulting solution was washed with 10% NaHCO$_3$ then the organic layer dried (MgSO$_4$). The volatiles were removed under reduced pressure and the residue chromatographed (SiO$_2$, 0-100% ethyl acetate/petroleum benzine 40-60° C.) to give the title compound (I23) (185 mg, 89%) as a colourless solid; $^1$H NMR (400 MHz, CDCl$_3$) δ 8.54 (s, 1H), 8.26 (d, J=8.3 Hz, 1H), 7.88 (s, 1H), 7.25 (dd, J=4.4, 2.4 Hz, 2H), 6.86 (dd, J=8.3, 1.7 Hz, 1H), 6.76 (d, J=1.7 Hz, 1H), 5.49 (d, J=39.2 Hz, 2H), 4.24 (s, 2H), 3.92 (s, 3H), 3.70 (s, 2H), 3.20-3.02 (m, 4H), 2.80 (m, 2H), 2.64 (s, 2H), 1.84 (d, J=12.8 Hz, 2H), 1.62 (dd, J=12.3, 3.5 Hz, 2H), 1.49 (s, 9H). LCMS Method C: rt 6.64 min; m/z 636.2 [M+Na]$^+$, 614.1 [M+1]$^+$, 612.2 [M−1]$^−$, 558.2 [M-t-Bu+2]$^+$.

(i) 2-(2-(2-(2-((2-Methoxy-4-(piperidin-4-yl)phenyl)amino)-5-(trifluoromethyl)pyrimidin-4-yl)ethyl)phenyl)acetamide (2)

Trifluoroacetic acid (1 mL) was added to a stirred solution of tert-butyl 4-(4-((4-(2-(2-amino-2-oxoethyl)phenethyl)-5-(trifluoromethyl)pyrimidin-2-yl)amino)-3-methoxyphenyl)piperidine-1-carboxylate (I23) (185 mg, 0.301 mmol) in DCM (10 mL) and the resulting solution was stirred at room temperature for 2 hours. DCM (20 mL) and 10% NaHCO$_3$ solution (10 mL) were added then the organic layer was dried (MgSO$_4$) and evaporated to dryness under reduced pressure to give the title compound (2) (125 mg, 81%) as a colourless solid; $^1$H NMR (400 MHz, CD$_2$Cl$_2$) δ 8.49 (s, 1H), 8.31 (d, J=8.3 Hz, 1H), 7.91 (s, 1H), 7.28-7.12 (m, 3H), 6.94 (bs, 2H), 6.85 (d, J=8.2 Hz, 1H), 6.78 (dd, J=11.8, 3.1 Hz, 1H), 6.35 (s, 1H), 5.94 (s, 1H), 3.88 (s, 3H), 3.65 (s, 2H), 3.42 (d, J=12.3 Hz, 2H), 3.24-3.02 (m, 4H), 2.91 (t, J=11.3 Hz, 2H), 2.75-2.61 (m, 1H), 2.10-1.83 (m, 4H). LCMS Method C: rt 4.92 min; m/z 514.1 [M+1]$^+$, 521.1 [M−1]$^+$.

Example 3

2-(2-(2-(2-((2-Methoxy-4-(1-methylpiperidin-4-yl)phenyl)amino)-5-(trifluoromethyl)pyrimidin-4-yl)ethyl)phenyl)acetamide (3)

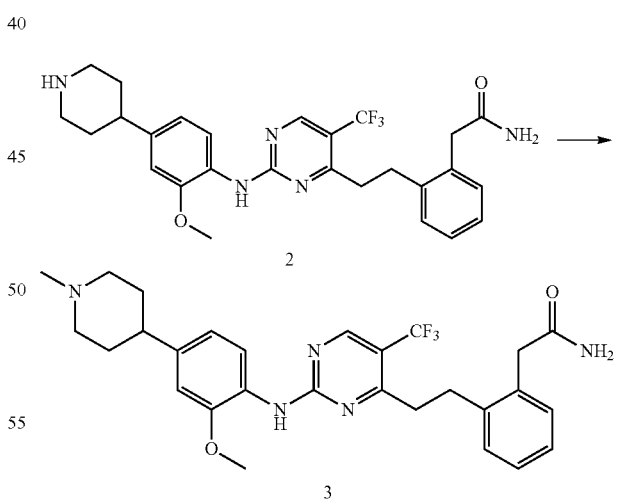

Formaldehyde solution (37% aq.; 32 µL, 0.39 mmol) was added to a stirred solution of 2-(2-(2-(2-((2-methoxy-4-(piperidin-4-yl)phenyl)amino)-5-(trifluoromethyl)pyrimidin-4-yl)ethyl)phenyl)acetamide (2) (40 mg, 78 µmol) in dry MeOH (2 mL). Sodium triacetoxyborohydride (83 mg, 0.39 mmol) was added under nitrogen and the resulting mixture was stirred at room temperature for 2 hours. The crude mixture was diluted with ethyl acetate and adsorbed onto silica gel. Chromatography (SiO$_2$, 0-20% MeOH/DCM) gave the title compound (3) (25 mg, 61%) as a solid; $^1$H NMR (400 MHz, CD$_2$Cl$_2$) δ 8.53 (s, 1H), 8.34 (d, J=8.3 Hz, 1H), 7.94 (s, 1H), 7.29-7.15 (m, 4H), 6.92 (dd, J=8.3, 1.4 Hz, 1H), 6.82 (d, J=1.7 Hz, 1H), 6.12 (bs, 1H), 5.84 (bs, 1H), 3.91 (s, 3H), 3.68 (s, 2H), 3.60 (d, J=10.6 Hz, 2H), 3.24-3.03 (m, 4H), 2.80 (s, 3H), 2.79 (m, 2H), 2.71 (m, 1H), 2.42-2.20 (m, 2H), 2.01 (m, 2H). LCMS Method C: rt 4.92 min; m/z 528.1 [M+1]$^+$, 526.1 [M−1]$^-$.

Example 3A

Alternative synthesis of 2-(2-(2-(2-((2-Methoxy-4-(piperidin-4-yl)phenyl)amino)-5-(trifluoromethyl)pyrimidin-4-yl)ethyl)phenyl)acetamide (2) and 2-(2-(2-(2-((2-Methoxy-4-(1-methylpiperidin-4-yl)phenyl)amino)-5-(trifluoromethyl)pyrimidin-4-yl)ethyl)phenyl)acetamide (3)

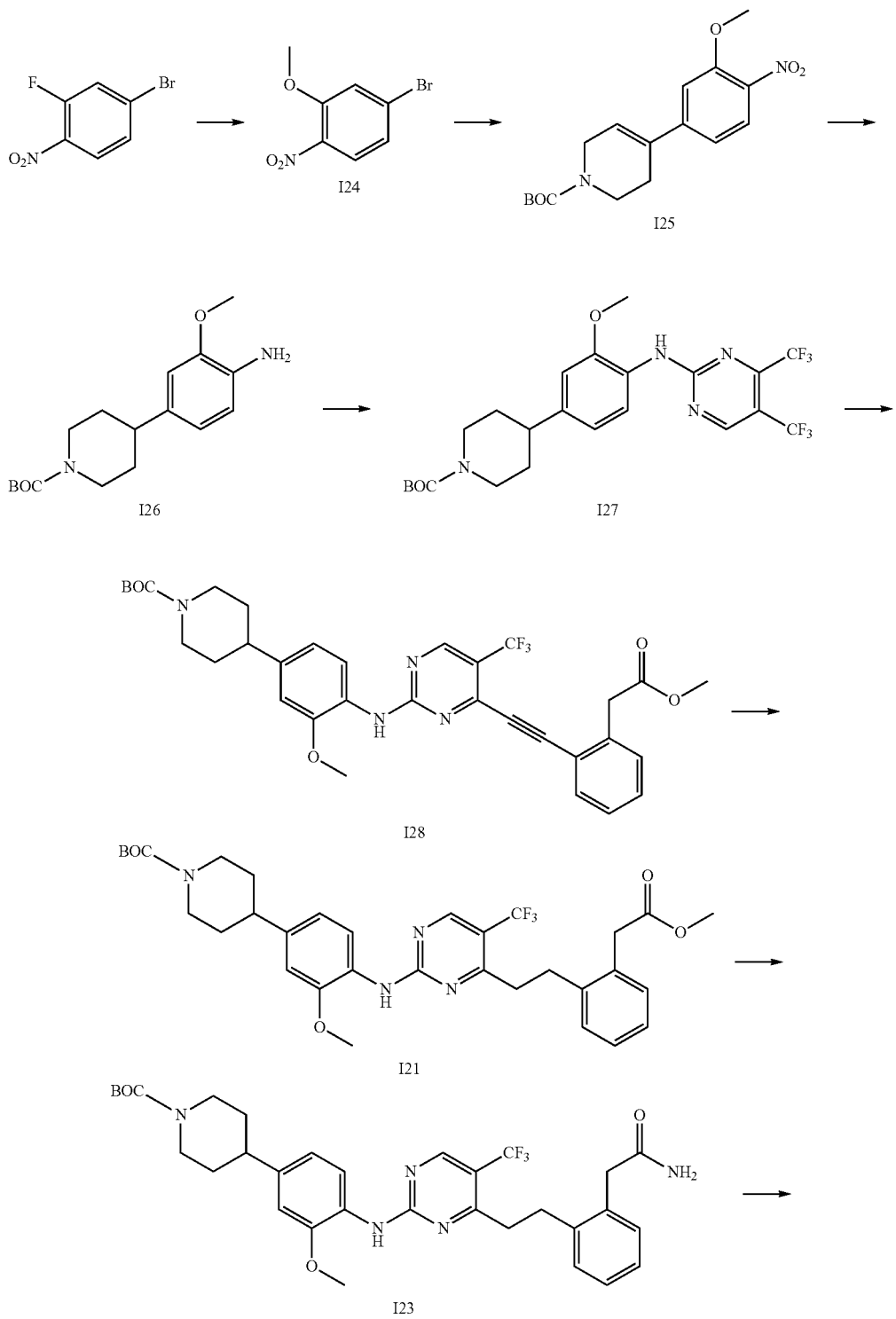

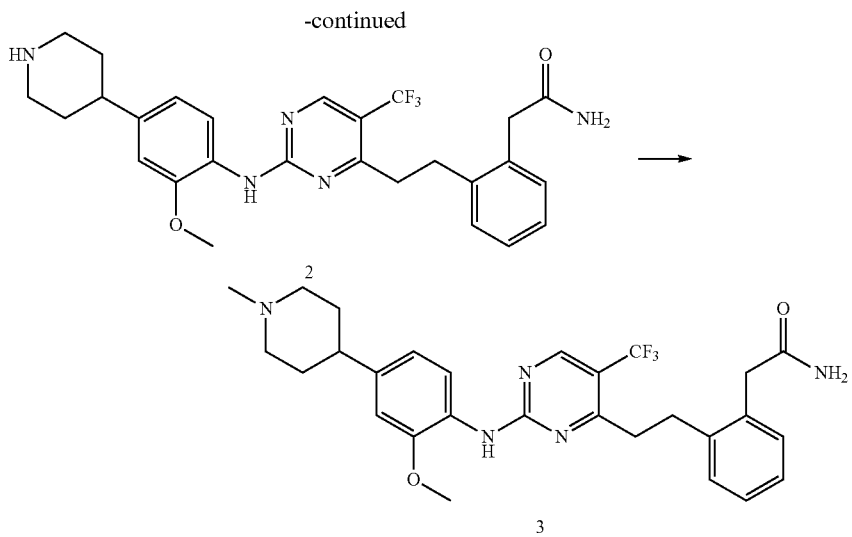

(a) 4-Bromo-2-methoxy-1-nitrobenzene (I24)

Sodium metal (3.14 g, 136 mmol) was added portion-wise to methanol (300 mL) under a nitrogen atmosphere. Once a homogeneous solution was obtained 4-bromo-2-fluoro-1-nitrobenzene (20.0 g, 91 mmol) was added and the resulting mixture stirred at 60° C. for 1 h. The volatiles were evaporated and the solid residue suspended in water (400 mL). The resulting suspension was filtered washing with water (2×50 mL). The filter cake was air dried to give the title compound (I24) (20.1 g, 95% yield) as a pale yellow solid; $^1$H NMR (400 MHz, CDCl$_3$) δ 7.75 (d, J=8.6 Hz, 1H), 7.24 (d, J=1.9 Hz, 1H), 7.18 (dd, J=8.6, 1.9 Hz, 1H), 3.97 (s, 3H). LCMS Method C: rt 5.85 min.

(b) tert-Butyl 4-(3-methoxy-4-nitrophenyl)-5,6-dihydropyridine-1(2H)-carboxylate (I25)

A mixture of 4-bromo-2-methoxy-1-nitrobenzene (I24) (2.364 g, 10.2 mmol), tert-butyl 4-(4,4,5,5-tetramethyl-1,3,2-dioxaborolan-2-yl)-5,6-dihydropyridine-1(2H)-carboxylate (3.00 g, 9.70 mmol), potassium carbonate (4.02 g, 29.1 mmol) and DMF (60 mL) was degassed with three vacuum/nitrogen cycles then PdCl$_2$(dppf)-DCM solvate (450 mg, 6 mol %) added under nitrogen in a Schlenk tube. A second tube was prepared in the same manner (ie. a total of 6.00 g starting boronate), and both tubes were heated to 85° C. under nitrogen. After 17 hours both tubes were cooled under nitrogen and added to 5% w/v aqueous lithium chloride (600 mL). The resulting mixture was extracted with ether (300 mL) and ethyl acetate (3×300 mL). The combined organic extracts were washed with water (600 mL) and brine (600 mL), dried (sodium sulphate) then evaporated to dryness. The residue was chromatographed (120 g silica cartridge, 0-60% ethyl acetate/petroleum benzine 40-60° C.) to give the title compound (I25) (5.863 g, 91% yield) as a yellow solid; $^1$H NMR (400 MHz, CDCl$_3$) δ 7.86 (d, J=8.5 Hz, 1H), 7.04-6.97 (m, 2H), 6.17 (s, 1H), 4.12 (d, J=2.5 Hz, 2H), 3.98 (s, 3H), 3.65 (t, J=5.6 Hz, 2H), 2.52 (s, 2H), 1.49 (s, 9H). LCMS Method C: rt 6.27 min; m/z 279.0 [M-tBu+2H]$^+$, 235.1 [M-Boc+2H]$^+$.

(c) tert-Butyl 4-(4-amino-3-methoxyphenyl)piperidine-1-carboxylate (I26) tert-Butyl 4-(3-methoxy-4-nitrophenyl)-5,6-dihydropyridine-1(2H)-carboxylate (I25)

(5.609 g, 16.78 mmol) was dissolved in 1:1 ethanol:ethyl acetate (500 mL) and Pd/C (2.50 g) was added. The mixture was stirred vigorously under hydrogen for five hours then filtered through celite. The celite was washed with ethyl acetate (500 mL) and the combined filtrates evaporated to give the title compound (I26) (4.93 g, 96% yield) as an off-white solid; $^1$H NMR (400 MHz, CDCl$_3$) δ 6.69-6.60 (m, 3H), 4.22 (s, 2H), 3.84 (s, 3H), 2.78 (t, J=12.4 Hz, 2H), 2.54 (ff, J=12.1, 3.5 Hz, 1H), 1.80 (d, J=13.1 Hz, 2H), 1.65-1.53 (m, 2H), 1.48 (s, 9H). LCMS Method C: rt 4.91 min; m/z 251.1 [M-tBu+2H]$^+$, 207.2 [M-Boc+2H]$^+$.

(d) tert-Butyl 4-(4-((4-chloro-5-(trifluoromethyl)pyrimidin-2-yl)amino)-3-methoxyphenyl)piperidine-1-carboxylate (I27)

A solution of 2,4-dichloro-5-(trifluoromethyl)pyrimidine (981 mg, 4.52 mmol) in 1:1 tert-butanol: dichloroethane (40 mL) was cooled to 0° C. under nitrogen then 1.0 M zinc(II) chloride in ether (4.52 mL, 4.52 mmol) was added dropwise. After one hour a solution of tert-butyl 4-(4-amino-3-methoxyphenyl)piperidine-1-carboxylate (I26) (1.26 g, 4.11 mmol) and triethylamine (0.860 mL, 6.17 mmol) in 1:1 tert-butanol: dichloroethane (50 mL) was added dropwise at −10° C. then the mixture was stirred for 16 hours allowing the temperature to rise to room temperature. The mixture was concentrated, evaporated onto silica and chromatographed (120 g silica cartridge, 0-10% ethyl acetate/petroleum benzine 40-60° C.) to give the title compound (I27) (1.277 g, 64% yield) as a white solid; $^1$H NMR (400 MHz, CDCl$_3$) δ 8.57 (s, 1H), 8.28 (d, J=8.3 Hz, 1H), 8.01 (s, 1H), 6.86 (dd, J=8.3, 1.8 Hz, 1H), 6.76 (d, J=1.8 Hz, 1H), 4.25 (br s, 2H), 3.91 (s, 3H), 2.87-2.73 (m, 2H), 2.64 (tt, J=12.1, 3.6 Hz, 1H), 1.83 (d, J=12.5 Hz, 2H), 1.69-1.54 (m, overlaps with water), 1.49 (s, 9H). LCMS Method C: rt 7.12 min; m/z 431.0 [M-tBu+2H]$^+$, 387.1 [M-Boc+2H]$^+$; m/z 485.1 [M−H]$^-$.

(e) tert-Butyl 4-(3-methoxy-4-((4-((2-(2-methoxy-2-oxoethyl)phenyl)ethynyl)-5-(trifluoromethyl)pyrimidin-2-yl)amino)phenyl)piperidine-1-carboxylate (I28)

A mixture of methyl 2-(2-ethynylphenyl)acetate (I4) (0.472 g, 2.71 mmol), tert-butyl 4-(4-((4-chloro-5-(trifluoromethyl)pyrimidin-2-yl)amino)-3-methoxyphenyl)piperidine-1-carboxylate (I27) (1.10 g, 2.26 mmol), triphenylphosphine (59 mg, 10 mol %), copper(I) iodide (43 mg, 10 mol %), bis(triphenylphosphine)palladium(II) chloride (79 mg, 5 mol %), DMF (12 mL) and triethylamine (1.26 mL, 9.04 mmol) was degassed with nitrogen in a microwave tube then heated under microwave irradiation at 120° C. for 15 minutes. Three additional tubes were prepared and heated as described above (i.e. a total of 4.40 g of I27). The cooled mixtures were combined, and poured into water (600 mL). The resulting mixture was extracted with dichloromethane (3×250 mL) then the combined organic phases were washed with water (2×300 mL), brine (300 mL), dried over sodium sulfate and evaporated to dryness. The residue was chromatographed (120 g silica cartridge, 0-50% ethyl acetate/petroleum benzine 40-60° C.) to give the title compound (I28) (5.52 g, 98% yield) as a yellow solid; $^1$H NMR (400 MHz, CDCl$_3$) δ 8.63 (s, 1H), 8.38 (d, J=8.3 Hz, 1H), 8.00 (s, 1H), 7.69 (dd, J=7.7, 0.9 Hz, 1H), 7.43 (td, J=7.6, 1.4 Hz, 1H), 7.36 (d, J=7.9 Hz, 1H), 7.32 (dd, J=7.5, 1.4 Hz, 1H), 6.87 (dd, J=8.4, 1.8 Hz, 1H), 6.76 (d, J=1.8 Hz, 1H), 4.26 (s, 2H), 3.97 (s, 2H), 3.91 (s, 3H), 3.71 (s, 3H), 2.81 (t, J=12.6 Hz, 2H), 2.64 (tt, J=12.2, 3.6 Hz, 1H), 1.84 (d, J=12.6 Hz, 2H), 1.69-1.55 (m, overlaps with water), 1.49 (s, 9H). LCMS Method C: rt 7.05 min; m/z (625.1 [M+H]$^+$, 569.1 [M-tBu+2H]$^+$; m/z 623.2 [M−H]$^−$.

(f) tert-Butyl 4-(3-methoxy-4-((4-(2-(2-methoxy-2-oxoethyl)phenethyl)-5-(trifluoromethyl)pyrimidin-2-yl)amino)phenyl)piperidine-1-carboxylate (I21)

tert-Butyl 4-(3-methoxy-4-((4-((2-(2-methoxy-2-oxoethyl)phenyl)ethynyl)-5-(trifluoromethyl)pyrimidin-2-yl)amino)phenyl)piperidine-1-carboxylate (I28) (5.52 g, 8.84 mmol) was dissolved in DMF (250 mL) then triethylamine (1 mL) and Pd/C (2.50 g) were added and the mixture stirred at 30° C. under hydrogen. After 16 hours the mixture was filtered through celite and the celite washed with DMF (250 mL). Triethylamine (1 mL) and Pd/C (2.50 g) were added to the combined filtrates and the mixture stirred at 30° C. under hydrogen. After 18 hours the resulting mixture was filtered through celite washing with ethyl acetate (300 mL). The filtrate was divided into two lots; each was poured into water (800 mL) and the resulting mixture extracted with ethyl acetate (3×300 mL). The ethyl acetate extracts from each lot were combined, washed with water (2×500 mL) and brine, dried (sodium sulfate) and evaporated. The two workups were combined and chromatographed (120 g silica cartridge, 0-20% ethyl acetate/petroleum benzine 40-60° C.) to give the title compound (I21) (3.620 g, 65% yield) as a white solid; $^1$H NMR (400 MHz, CDCl$_3$) δ 8.55 (s, 1H), 8.37 (d, J=8.3 Hz, 1H), 7.91 (s, 1H), 7.29-7.18 (m, overlaps with CHCl$_3$), 6.85 (dd, J=8.3, 1.8 Hz, 1H), 6.77 (d, J=1.8 Hz, 1H), 4.26 (s, 2H), 3.93 (s, 3H), 3.68 (s, 3H), 3.19-3.01 (m, 4H), 2.81 (t, J=12.7 Hz, 2H), 2.64 (tt, J=12.0, 3.5 Hz, 1H), 1.85 (d, J=13.3 Hz, 2H), 1.70-1.57 (m, overlaps with water), 1.49 (s, 9H). LCMS Method C: rt 7.14 min; m/z 629.2 [M+H]$^+$, 573.1 [M-tBu+2H]$^+$; m/z 627.2 [M−H].

(g) tart-Butyl 4-(4-((4-(2-(2-amino-2-oxoethyl)phenethyl)-5-(trifluoromethyl)pyrimidin-2-yl)amino)-3-methoxyphenyl)piperidine-1-carboxylate (I23)

tert-Butyl 4-(3-methoxy-4-((4-(2-(2-methoxy-2-oxoethyl)phenethyl)-5-(trifluoromethyl)pyrimidin-2-yl)amino)phenyl)piperidine-1-carboxylate (I21) (3.62 g, 5.76 mmol) was dissolved in THF (200 mL) then a solution of lithium hydroxide monohydrate (1.21 g, 28.8 mmol) in water (100 mL) was added. The resulting mixture was stirred for 18 hours at room temperature then concentrated. The residue was poured into saturated sodium bicarbonate (200 mL) and water (300 mL). The resulting mixture was extracted with ethyl acetate (3×300 mL) and the combined organic phases were washed with brine, dried over sodium sulfate and evaporated. The residue was evaporated from toluene then dissolved in THF (70 mL) and DMF (12 mL) at 30° C. under nitrogen. The mixture was stirred vigorously while HOBT (1.012 g, 7.49 mmol), EDCl.HCl (1.330 g, 7.49 mmol) and DIPEA (5.02 mL, 28.8 mmol) were added. After five minutes ammonium carbonate (2.77 g, 28.8 mmol) was added and stirring continued for 16 hours. The resulting mixture was poured into saturated sodium bicarbonate (300 mL) and extracted with ethyl acetate (3×300 mL). The combined organic phases were washed with 1:1 saturated brine: water (2×300 mL), brine (300 mL), dried over sodium sulfate and evaporated. The residue was chromatographed (120 g silica cartridge, 0-80% ethyl acetate/petroleum benzine 40-60° C.) to give the title compound (I23) (2.698 g, 76% over two steps) as a white solid; $^1$H NMR (400 MHz, CDCl$_3$) δ 8.54 (s, 1H), 8.28 (d, J=8.3 Hz, 1H), 7.86 (s, 1H), 7.29-7.22 (m, overlaps with residual CHCl$_3$), 6.86 (dd, J=8.3, 1.9 Hz, 1H), 6.76 (d, J=1.9 Hz, 1H), 5.37 (d, J=15.9 Hz, 2H), 4.25 (s, 2H), 3.93 (s, 3H), 3.71 (s, 2H), 3.18-3.04 (m, 4H), 2.81 (t, J=12.5 Hz, 2H), 2.64 (tt, J=12.0, 3.4 Hz, 1H), 1.84 (d, J=12.9 Hz, 2H), 1.69-1.55 (m, overlaps with water), 1.49 (s, 9H). LCMS Method C: rt 6.59 min; m/z 614.2 [M+H]$^+$, 558.1 [M-tBu+2H]$^+$; m/z 612.2 [M−H]$^−$.

(h) 2-(2-(2-(2-((2-Methoxy-4-(piperidin-4-yl)phenyl)amino)-5-(trifluoromethyl)pyrimidin-4-yl)ethyl)phenyl)acetamide (2)

A solution of tert-butyl 4-(4-((4-(2-(2-amino-2-oxoethyl)phenethyl)-5-(trifluoromethyl)pyrimidin-2-yl)amino)-3-methoxyphenyl)piperidine-1-carboxylate (I23) (2.694 g, 4.39 mmol) was dissolved in dichloromethane (150 mL), and TFA (15 mL) was added. The resulting mixture was stirred for 16 hours then concentrated. The residue was suspended in 10% sodium hydroxide (200 mL) then extracted with ethyl acetate (5×200 mL). The combined organic phases were washed with brine (300 mL), dried over sodium sulfate and evaporated to give the title compound (2) (2.252 g, 100% yield) as a white solid; $^1$H NMR (400 MHz, CDCl$_3$) δ 8.53 (s, 1H), 8.26 (d, J=8.3 Hz, 1H), 7.85 (s, 1H), 7.29-7.21 (m, overlaps with CHCl$_3$), 6.87 (d, J=8.3 Hz, 1H), 6.80 (s, 1H), 5.43 (d, J=10.1 Hz, 2H), 3.92 (d, J=1.3 Hz, 3H), 3.70 (s, 2H), 3.20 (d, J=12.7 Hz, 2H), 3.15-3.05 (m, 4H), 2.75 (t, J=12.2 Hz, 2H), 2.61 (tt, J=12.0, 3.5 Hz, 1H), 1.89-1.76 (m, overlaps with water), 1.67 (qd, J=12.7, 3.9 Hz, 2H). LCMS Method C: rt 4.92 min; m/z 514.1 [M+H]$^+$, 536.1 [M+Na]$^+$; m/z 512.2 [M−H]$^−$.

(i) 2-(2-(2-(2-((2-Methoxy-4-(1-methylpiperidin-4-yl)phenyl)amino)-5-(trifluoromethyl)pyrimidin-4-yl)ethyl)phenyl)acetamide (3)

2-(2-(2-(2-((2-Methoxy-4-(piperidin-4-yl)phenyl)amino)-5-(trifluoromethyl)pyrimidin-4-yl)ethyl)phenyl)acetamide (2) (2.249 g, 4.38 mmol) was dissolved in methanol (220 mL) and 37% formaldehyde solution (0.483 mL, 17.5 mmol) was added. After five minutes sodium tris(acetoxy) borohydride (4.641 g, 21.9 mmol) was added and stirring continued at room temperature for two hours. The volatiles were evaporated and the residue suspended in 5% aqueous sodium hydroxide (200 mL). The resulting mixture was extracted with ethyl acetate (5×200 mL) then the combined organic phases were washed with brine (500 mL), dried over sodium sulfate and evaporated. The residue was evaporated from ether and the solvent traces removed under high vacuum to give the title compound (3) (2.196 g, 95% yield) as a white solid; $^1$H NMR (400 MHz, CDCl$_3$) δ 8.53 (s, 1H), 8.24 (d, J=8.2 Hz, 1H), 7.85 (s, 1H), 7.28-7.22 (m, overlaps with CHCl$_3$), 6.88 (dd, J=8.3, 1.9 Hz, 1H), 6.81 (d, J=1.8 Hz, 1H), 5.41 (s, 2H), 3.90 (s, 3H), 3.70 (s, 2H), 3.16-3.06 (m, 4H), 2.99 (d, J=12.1 Hz, 2H), 2.48 (tt, J=10.5, 5.9 Hz, 1H), 2.34 (s, 3H), 2.07 (td, J=11.1, 4.1 Hz, 2H), 1.89-1.77 (m, overlaps with water). LCMS Method C: rt 4.94 min; m/z 528.1 [M+H]$^+$, 550.1 [M+Na]$^+$; m/z 526.2 [M−H]$^−$.

Example 4

2-(2-(2-(2-((4-(1-Ethylpiperidin-4-yl)-2-methoxyphenyl)amino)-5-(trifluoromethyl)pyrimidin-4-yl)ethyl)phenyl) acetamide (4)

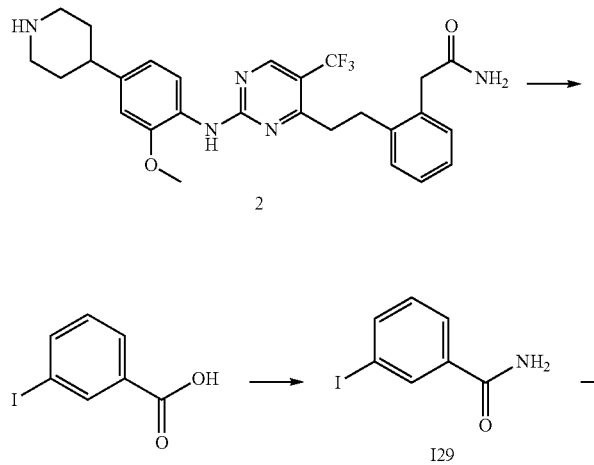

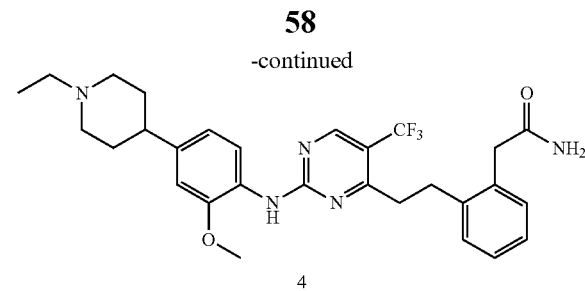

Acetaldehyde (18 mg, 0.39 mmol) was added to a stirred solution of 2-(2-(2-(2-((2-methoxy-4-(piperidin-4-yl)phenyl)amino)-5-(trifluoromethyl)pyrimidin-4-yl)ethyl)phenyl) acetamide (2) (40 mg, 78 μmol) in dry MeOH (2 mL). Sodium triacetoxyborohydride (83 mg, 0.39 mmol) was added under nitrogen and the resulting mixture was stirred at room temperature for 2 hours. The crude mixture was diluted with ethyl acetate and adsorbed onto silica gel. Chromatography (SiO$_2$, 0-20% MeOH/DCM) gave the title compound (4) (10 mg, 24%) as a light coloured solid; $^1$H NMR (400 MHz, CD2Cl$_2$) δ 8.52 (s, 1H), 8.34 (d, J=8.3 Hz, 1H), 7.92 (s, 1H), 7.28-7.14 (m, 4H), 6.92 (d, J=8.3 Hz, 1H), 6.82 (d, J=1.7 Hz, 1H), 5.91 (bs, 1H), 5.87 (bs, 1H), 3.91 (s, 3H), 3.66 (s, 2H), 3.63 (m, 2H), 3.20-3.01 (m, 6H), 2.73 (d, J=11.7 Hz, 2H), 2.42-2.21 (m, 3H), 2.02 (d, J=18.0 Hz, 4H), 1.37 (t, J=7.3 Hz, 3H). LCMS Method C: rt 4.96 min; m/z 542.2 [M+1]$^+$, 540.1 [M−1]$^−$.

Example 5

3-(2-(2-((2-Methoxy-4-(piperidin-4-yl)phenyl)amino)-5-(trifluoromethyl)pyrimidin-4-yl)ethyl)benzamide (5)

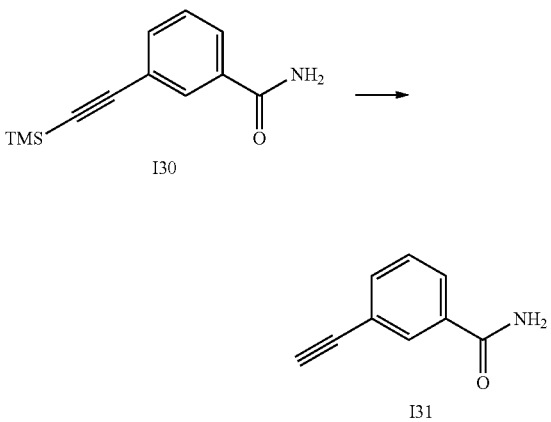

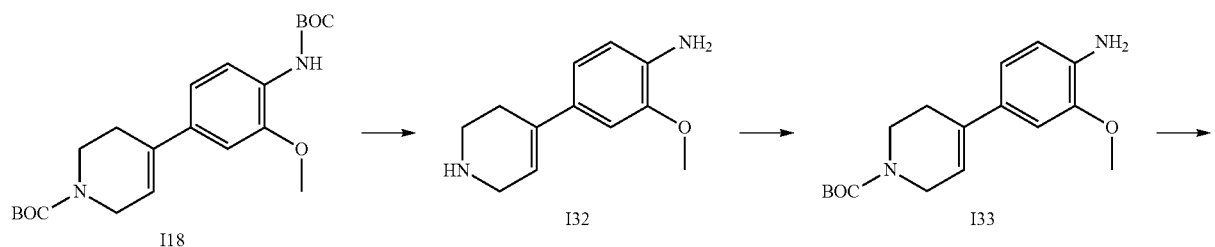

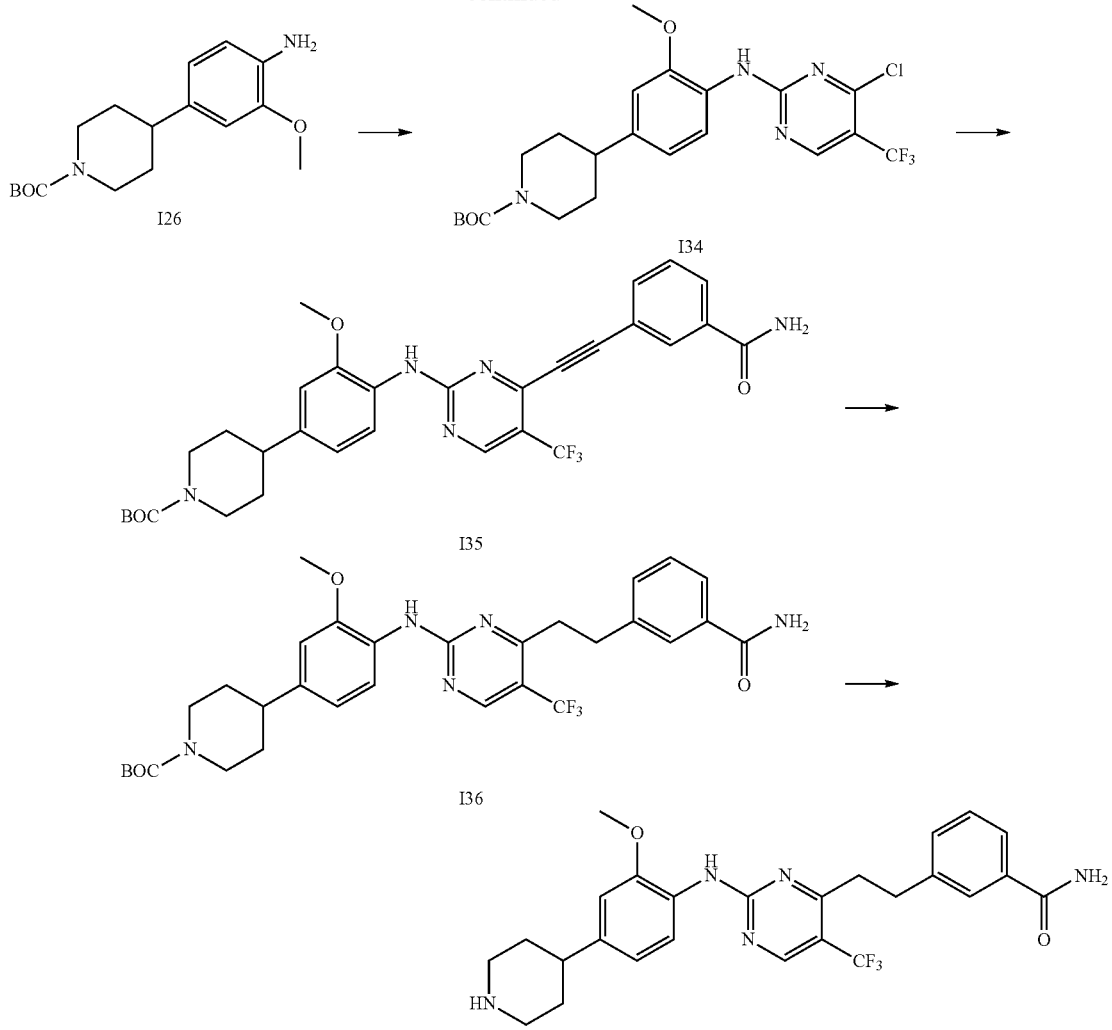

(a) 3-Iodobenzamide (I29)

To a stirred solution of 3-iodobenozic acid (2.00 g, 8.06 mmol) and DIPEA (5.62 mL, 32.3 mmol) in MeCN (100 mL) at room temperature was added HOST (1.63 g, 12.1 mmol) and EDCl.HCl (2.32 g, 12.1 mmol). After stirring for 10 minutes, ammonium carbonate (4.65 g, 48.4 mmol) was added and the resulting solution was stirred overnight. The volatiles were removed in vacuo to yield a crude solid which was suspended in water (100 mL). The resulting suspension was sonicated for 10 minutes then the solid collected by filtration. The filter cake was washed with water (20 mL) and dried to yield the title compound (I29) (1.65 g 83%) as a brown solid; 1H NMR (400 MHz, CDCl$_3$) δ 8.13 (t, J=1.6 Hz, 1H), 7.83 (ddd, J=7.9, 1.7, 1.1 Hz, 1H), 7.73 (ddd, J=7.8, 1.7, 1.1 Hz, 1H), 7.16 (t, J=7.8 Hz, 1H), 6.18-5.49 (m, J=137.3 Hz, 2H). LCMS Method C: rt=5.04 min; m/z=248 [M+1]$^+$.

(b) 3-((Trimethylsilyl)ethynyl)benzamide (I30)

A solution of 3-iodobenzamide (I29) (1.65 g, 6:66 mmol), Cu(I)I (127 mg, 0.666 mmol) and triphenylphosphine (524 mg, 2.00 mmol) in THF (100 mL) and triethylamine (4.64 mL, 33.3 mmol) was sonicated for 10 minutes under a nitrogen atmosphere. PdCl$_2$(PPh$_3$)$_2$ (642 mg, 0.67 mmol) and TMS acetylene (1.88 mL, 13.3 mmol) were then added and the reaction stirred at room temperature for 3 days. The volatiles were evaporated in vacuo and the residue chromatographed on silica gel (0-50% ethyl acetate/petroleum benzine 40-60° C.) to give the title compound (130) (1.53 g); $^1$H NMR (400 MHz, CDCl$_3$) δ 7.78 (t, J=1.5 Hz, 1H), 7.67 (ddd, J=7.8, 1.8, 1.2 Hz, 1H), 7.53-7.48 (m, 1H), 7.29 (td, J=7.8, 0.5 Hz, 1H), 0.15 (s, 9H).

(c) 3-Ethynylbenzamide (I31)

Potassium carbonate (1.84 g, 13.3 mmol) was added to a stirred solution of 3-((trimethylsilyl)ethynyl)benzamide (130) (1.45 g, 6.66 mmol) in MeOH (15 mL) at room temperature. The resulting suspension was stirred for 30 minutes then water (100 mL) and EtOAc (100 mL) were added. The resulting precipitate was collected via filtration and after air drying this was suspended in a 1:1 mix of acetone and methanol (15 mL). After sonication the resulting suspension was filtered to give the title compound (I31) (335 mg, 35%) which was used without additional purification.

(d) 2-Methoxy-4-(1,2,3,6-tetrahydropyridin-4-yl) aniline (I32)

To a solution of tert-butyl 4-(4-((tert-butoxycarbonyl)amino)-3-methoxyphenyl)-5,6-dihydropyridine-1(2H)-carboxylate (I18) (6.7 g, 0.016 mol) in DCM (60 mL) was added TFA (6.0 mL, 0.081 mol) and the resulting solution was stirred at room temperature for 14 hours. An additional 5 mL of TFA was added and the reaction was stirred for a further 6 hours. The volatiles were removed in vacuo and the residue taken up in $CH_3CN/H_2O$ and lyophilised to give the title compound (I32) as the TFA salt (6.38 g, 91%) as a brown oil; $^1$H NMR (400 MHz, $d_4$-MeOH) δ 7.31 (dd, J=7.3, 2.8 Hz, 1H), 7.21 (t, J=2.0 Hz, 1H), 7.13-7.09 (m, 1H), 6.20 (tt, J=3.4, 1.6 Hz, 1H), 3.83 (dd, J=5.7, 2.4 Hz, 2H), 3.43 (t, J=6.1 Hz, 2H), 2.77 (ddd, J=8.0, 3.9, 1.9 Hz, 2H). LCMS Method C: rt 1.38 min; m/z 201.1 $[M+H]^+$.

(e) tert-Butyl 4-(4-amino-3-methoxyphenyl)-5,6-dihydropyridine-1(2H)-carboxylate (I33)

To a stirred solution of 2-methoxy-4-(1,2,3,6-tetrahydropyridin-4-yl)aniline (I32) (6.38 g, 14.8 mmol) in MeOH (50 mL) at room temperature was added a solution of $(Boc)_2O$ (3.27 g, 15.0 mmol) in MeOH (20 mL) drop-wise over 5 minutes and the resultant solution was stirred for 1 hour. The mixture was concentrated in vacuo and the residue was taken up in 2 M NaOH (50 mL) solution. The aqueous layer was extracted with $CH_2Cl_2$ (4×50 mL) and the combined organic extracts were washed with brine (50 mL) then dried ($MgSO_4$). The solvent was removed in vacuo to give the title compound (I33) (1.97 g, 43%) as a brown oil; $^1$H NMR (400 MHz, $CDCl_3$) δ 6.85-6.80 (m, 1H), 6.67 (d, J=8.1 Hz, 1H), 5.90 (s, 1H), 4.05 (d, J=2.7 Hz, 1H), 3.87 (s, 3H), 3.62 (t, J=5.7 Hz, 1H), 2.49 (s, 2H), 1.49 (s, 9H).

(f) tert-Butyl 4-(4-amino-3-methoxyphenyl)piperidine-1-carboxylate (I26)

To a suspension of 10% Pd/C (0.068 g) in DMF (2 mL) under nitrogen was added a solution of tert-butyl 4-(4-amino-3-methoxyphenyl)-5,6-dihydropyridine-1(2H)-carboxylate (I33) (2.0 g, 6.5 mmol) in EtOH (50 mL) and the resulting suspension was stirred under an atmosphere of hydrogen at room temperature for 24 hours. The reaction mixture was filtered through celite, washing with ethyl acetate (100 mL). The filtrate was evaporated to dryness to give the title compound (I26) (1.42 g, 72%) as a light brown solid; $^1$H NMR (400 MHz, $CDCl_3$) δ 6.66-6.58 (m, 3H), 4.21 (s, 2H), 3.76-3.66 (m, 4H), 2.53 (tt, J=12.1, 3.5 Hz, 1H), 1.84-1.75 (m, 2H), 1.55 (tdd, J=11.5, 6.4, 3.1 Hz, 1H), 1.47 (s, 9H).

(g) tert-Butyl 4-(4-((4-chloro-5-(trifluoromethyl)pyrimidin-2-yl)amino)-3-methoxyphenyl)piperidine-1-carboxylate (I34)

Zinc chloride (1.0 M in $Et_2O$) (8.56 mL, 8.56 mmol) was added to a solution of 2,4-dichloro-5-(trifluoromethyl)pyrimidine (1.06 mL, 7.85 mmol) in 1:1 DCE/t-BuOH (10 mL) at 0° C. under nitrogen. The mixture was stirred for 1 hour at 0° C. and then tert-butyl 4-(4-amino-3-methoxyphenyl)piperidine-1-carboxylate (I26) (1.97 g, 7.13 mmol) in 1:1 DCE/tBuOH (30 mL) was added. A solution of triethylamine (600 µL, 0.432 mmol, 1.1 eq) in 1:1 DCE/t-BuOH (10 mL) was next added drop-wise at 0° C. The reaction mixture was vigorously stirred for a further 30 minutes at 0° C. after the final addition and then at room temperature for 24 hours. The solvent was removed in vacuo to afford a brown oily residue which was purified by column chromatography on silica gel (0-45% EtOAc in petroleum benzine 40-60° C.) to give a pale yellow oil which solidified upon standing. This was triturated sequentially with water, 1:1 water/MeOH and MeOH and the precipitate was filtered to afford a white solid. The solid was recrystallised from water to give the title compound (I34) (0.92 g, 30%) as a white solid; $^1$H NMR (400 MHz, $CDCl_3$) δ 8.57 (s, 1H), 8.28 (d, J=8.3 Hz, 1H), 8.01 (s, 1H), 6.86 (dd, J=8.4, 1.7 Hz, 1H), 6.76 (d, J=1.8 Hz, 1H), 4.25 (s, 2H), 3.91 (s, 3H), 2.81 (t, J=11.8 Hz, 2H), 2.64 (tt, J=12.1, 3.6 Hz, 1H), 1.83 (d, J=13.5 Hz, 2H), 1.69-1.57 (m, 2H), 1.49 (s, 9H). LCMS Method C: rt 7.00 min; m/z=487.0 $[M+H]^+$, 431.0 $[M-^tButyl+H]^+$, 485.0 $[M-H]^-$.

(h) tert-Butyl 4-(4-((4-(3-carbamoylphenyl)ethynyl)-5-(trifluoromethyl)pyrimidin-2-yl)amino)-3-methoxyphenyl)piperidine-1-carboxylate (I35)

To a mixture of tert-butyl 4-(4-((4-chloro-5-(trifluoromethyl)pyrimidin-2-yl)amino)-3-methoxyphenyl)piperidine-1-carboxylate (I34) 0.098 g, 0.20 mmol), 3-ethynylbenzamide (I31) (0.038 g, 0.26 mmol), $PdCl_2(PPh_3)_2$ (9 mg, 0.01 mmol), triphenylphosphine (0.010 g, 0.04 mmol) and copper (I) iodide (0.009 g, 0.05 mmol) in DMF (2 mL), that had been degassed with nitrogen for 10 minutes, was added triethylamine (0.090 mL, 0.65 mmol). The mixture was degassed with nitrogen then heated to 120° C. for 25 minutes under microwave irradiation. On cooling to room temperature the resulting mixture was left overnight, then an additional portion of 3-ethynylbenzamide (I26) (0.047 g, 0.32 mmol) was added. After degassing with nitrogen the reaction was heated at 120° C. for 25 minutes under microwave irradiation. The volatiles were evaporated under reduced pressure and the residue purified using silica gel column chromatography (20-70% EtOAc/petroleum benzine 40-60° C.) to give the title compound (I35) (0.073 g, 61%) as a yellow solid; $^1$H NMR (400 MHz, $CDCl_3$) δ 8.66 (s, 1H), 8.35 (d, J=8.3 Hz, 1H), 8.04 (dd, J=1.4, 1.4 Hz, 1H), 8.02 (s, 1H), 7.93 (ddd, J=7.9, 1.8, 1.2 Hz, 1H), 7.80 (m, 1H), 7.53 (m, 1H), 6.88 (dd, J=8.3, 1.6 Hz, 1H), 6.76 (d, J=1.8 Hz, 1H), 4.27 (m, 2H), 3.91 (s, 3H), 2.81 (m, J=12.2 Hz, 2H), 2.64 (tt, J=12.2, 3.4 Hz, 1H), 1.84 (m, 2H), 1.65 (m, 2H), 1.49 (s, 9H). LCMS Method C: rt 6.59 min; m/z 496.1 $[(M-Boc)+H]^+$, 540.0 $[(M-t-Bu)+H]^+$.

(i) tert-Butyl 4-(4-((4-(3-carbamoylphenethyl)-5-(trifluoromethyl)pyrimidin-2-yl-amino)-3-methoxyphenyl)piperidine-1-carboxylate (I36)

A mixture of tert-butyl 4-(4-((4-((3-carbamoylphenyl)ethynyl)-5-(trifluoromethyl)pyrimidin-2-yl)amino)-3-methoxyphenyl)piperidine-1-carboxylate (I35) (0.073 g, 0.12 mmol) and 10% palladium on activated carbon (0.042 g) in DMF (3 mL) was stirred under a hydrogen atmosphere for 20 hours. The resulting mixture was filtered and filtrate evaporated to dryness under reduced pressure. The residue was chromatographed on silica gel (20-100% acetone/petroleum benzine 40-60° C.) to give the title compound (I36) (0.070 g, 95%).

3-(2-(2-((2-Methoxy-4-(piperidin-4-yl)phenyl)amino)-5-(trifluoromethyl)pyrimidin-4-yl)ethyl)benzamide (5)

A mixture of tert-butyl 4-(4-((4-(3-carbamoylphenethyl)-5-(trifluoromethyl)pyrimidin-2-yl)amino)-3-methoxyphenyl)piperidine-1-carboxylate (I36) (0.070 g, 0.12 mmol) and TFA (0.200 mL, 2.61 mmol) in THF (3 mL) was stirred 16 hours at room temperature. The mixture was concentrated under reduced pressure and azeotroped with toluene. The residue was then purified using a SCX cartridge (MeOH, 0.5% NH$_3$/MeOH). The methanolic ammonia eluent was concentrated then dissolved in hot acetonitrile which was allowed to cool to room temperature. The cooled acetonitrile solution was filtered and the filtrate was concentrated, taken up in hot acetonitrile (2 mL) and water (1 mL) then freeze dried to give the title compound (5) (49.4 mg, 85%) as a white solid. A portion of this material was further purified by mass directed auto preparative HPLC to give the title compound (5) (4.5 mg) as a while solid; $^1$H NMR (400 MHz, d$_6$-DMSO) δ 8.90 (m, 1H), 8.57 (s, 1H), 8.41 (s, 1H), 7.93 (s, 1H), 7.77 (s, 1H), 7.71 (m, 1H), 7.62 (dd, J=7.5, 7.5 Hz, 1H), 7.34 (m, 2H), 6.94 (dd, J=7.3, 1.6 Hz, 1H), 6.82 (ddd, J=7.9, 3.4, 1.5 Hz, 1H), 3.82 (s, 3H), 3.12 (m, 2H), 3.05 (m, 4H), 2.89 (m, 1H), 2.68 (m, 2H), 2.20 (m, 1H), 1.78 (m, 2H), 1.64 (m, 2H). LCMS Method C: rt 4.89 min; m/z 500.1[M+H]$^+$.

washed with sat. aqueous NaHCO$_3$ (10 mL). The Aqueous was further extracted with EtOAc (10 mL) and the combined organic layers were washed with brine (10 mL) and water (10 mL) then dried using a phase separation cartridge. The organics were concentrated under reduced pressure and purified using silica gel column chromatography (0-30% MeOH/EtOAc+1% 2 M ethanolic NH$_3$). The product was then taken up in minimal hot acetonitrile and water and freeze dried to give the title compound (6) (0.016 g, 74%) as a white solid; $^1$H NMR (400 MHz, d$_6$-Acetone) δ 8.62 (s, 1H), 8.27 (dd, J=8.3, 4.1 Hz, 1H), 8:15 (s, 1H), 7.90 (s, 1H), 7.78 (d, J=7.5 Hz, 1H), 7.41 (m, 3H), 6.99 (d, J=1.7 Hz, 1H), 6.89 (dd, J=8.2, 1.6 Hz, 1H), 6.55 (s, 1H), 3.98 (s, 3H), 3.20 (m, 4H), 2.90 (m, 2H), 2.57 (m, 1H), 2.22 (s, 3H), 1.98 (td, J=11.2, 3.8 Hz, 2H), 1.78 (m, 4H). LCMS Method C: rt 4.97 min; m/z 514.2 [M+H]$^+$.

Example 6

3-(2-(2-((2-Methoxy-4-(1-methylpiperidin-4-yl)phenyl)amino)-5-(trifluoromethyl)pyrimidin-4-yl)ethyl)benzamide (6)

Example 7

3-(2-(2-((4-(1-Ethylpiperidin-4-yl)-2-methoxyphenyl)amino)-5-(trifluoromethyl)pyrimidin-4-Methyl)benzamide (7)

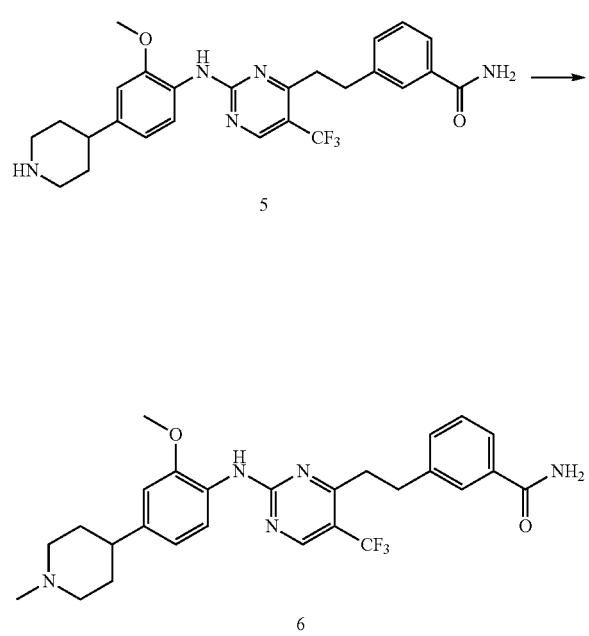

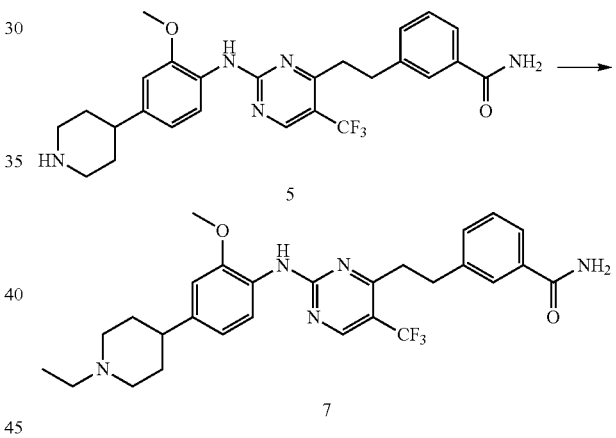

To a solution of 3-(2-(2-((2-methoxy-4-(piperidin-4-yl)phenyl)amino)-5-(trifluoromethyl)pyrimidin-4-yl)ethyl)benzamide (5) (0.021 g, 0.042 mmol) in anhydrous methanol (2.00 mL) was added 37% aqueous formaldehyde (0.012 mL, 0.16 mmol) and sodium triacetoxyborohydride (0.044 g, 0.21 mmol) under a N$_2$ atmosphere. The mixture was then stirred for 1.5 hours. The resulting mixture was concentrated under reduced pressure and diluted with EtOAc (10 mL) and To a solution of 3-(2-(2-((2-methoxy-4-(piperidin-4-yl)phenyl)amino)-5-(trifluoromethyl)pyrimidin-4-yl)ethyl)benzamide (5) (0.021 g, 0.04 mmol) in methanol (2.00 mL) was added acetaldehyde (0.010 mL, 0.18 mmol) followed by sodium triacetoxyborohydride (0.044 g, 0.21 mmol) under a N2 atmosphere. The mixture was then stirred at room temperature for 5 hours. The resulting mixture was concentrated under reduced pressure and purified using silica gel column chromatography (0-30% MeOH/EtOAc+1% 2 M ethanolic NH$_3$). The product was further purified using mass directed auto-preparative HPLC to give the title compound (7) (3.5 mg, 16%); $^1$H NMR (400 MHz, d$_6$-Acetone) δ 8.62 (s, 1H), 8.24 (m, 2H), 7.91 (s, 1H), 7.78 (ddd, J=7.5, 1.4, 1.4 Hz, 1H), 7.41 (m, 3H), 7.01 (d, J=1.7 Hz, 1H), 6.89 (dd, J=8.3, 1.7 Hz, 1H), 6.60 (m, 1H), 3.97 (s, 3H), 3.21 (m, 4H), 3.12 (m, 2H), 2.55 (m, 3H), 2.16 (m, 2H), 1.85 (m, 4H), 1.11 (t, J=7.2 Hz, 3H). LCMS Method C: rt 4.98 min; m/z 528.2 [M+H]$^+$.

Example 8
2-(2-(2-(2-((2-Ethyl-4-(piperidin-4-yl)phenyl)amino)-5-(trifluoromethyl)pyrimidin-4-yl)ethyl)phenyl)acetamide (8)
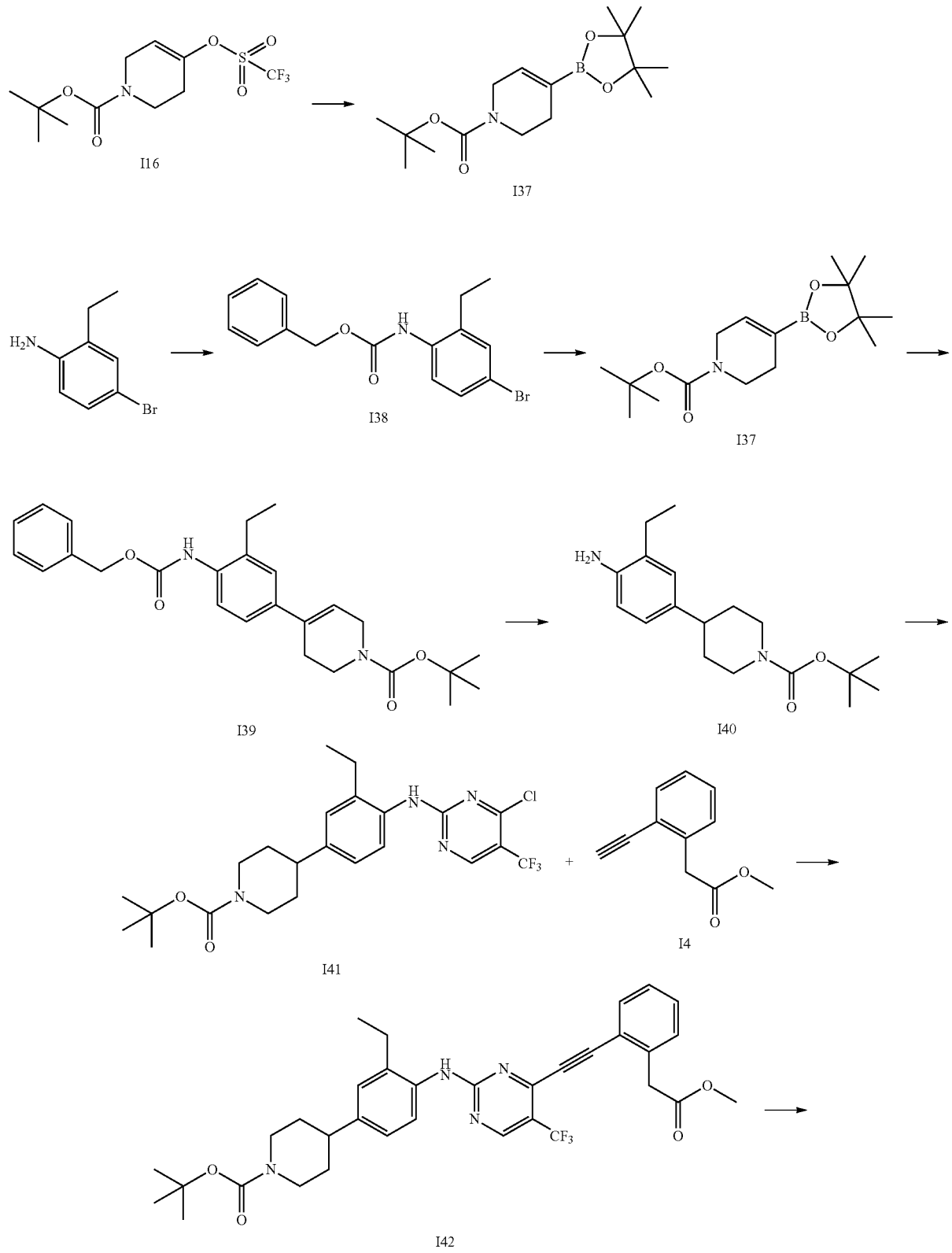

-continued

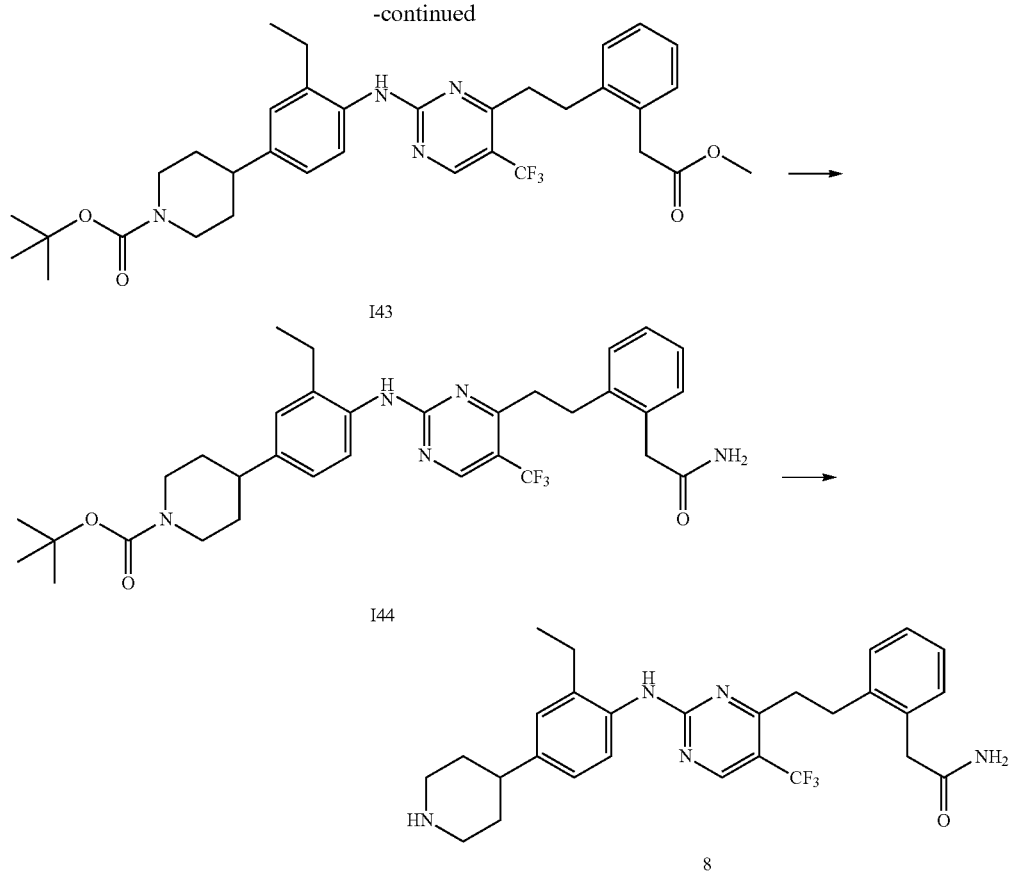

(a) tert-Butyl 4-(4,4,5,5-tetramethyl-1,3,2-dioxaborolan-2-yl)-5,6-dihydropyridine-1(2H)-carboxylate (I37)

Bis(pinacolato)diboron (0.511 g, 2.01 mmol), potassium acetate (0.592 g, 6.04 mmol), dppf (56 mg, 5 mol %), and PdCl$_2$(dppf) dichloromethane solvate (83 mg, 5 mol %) were loaded into a Schlenk tube, and purged with nitrogen. A solution tart-butyl 4-(((trifluoromethyl)sulfonyl)oxy)-5,6-dihydropyridine-1(2H)-carboxylate (I16) (1.00 g, 3.02 mmol) in dioxane (5 mL) was added, the mixture degassed with 3× vacuum/nitrogen cycles then brought to 80° C. under nitrogen. After 16 hours the mixture was cooled, and added to water (100 mL). The resulting mixture was extracted with dichloromethane (3×50 mL), and the combined DCM extracts washed with brine (50 mL), dried over sodium sulfate and evaporated. Chromatography (40 g silica cartridge, 0-100% ethyl acetate/petroleum benzine 40-60° C.) gave the title compound (I37) (383 mg, 62% yield) as a crystalline white solid; $^1$H NMR (400 MHz, CDCl$_3$) δ 6.45 (s, 1H), 3.94 (d, J=2.7 Hz, 2H), 3.43 (t, J=5.5 Hz, 2H), 2.22 (s, 2H), 1.45 (s, 9H), 1.26 (s). LCMS Method C: rt 6.48 min; m/z 254.2 [M-tBu+2H]$^+$, 210.2 [M-Boc+2H]$^+$.

(b) Benzyl(4-bromo-2-ethylphenyl)carbamate (I38)

4-Bromo-2-ethylaniline (500 mg, 2.50 mmol) was dissolved in toluene (25 mL), sodium carbonate (397 mg, 3.75 mmol) and benzyl chloroformate (0.428 mL, 3.00 mmol) were added and the mixture stirred under nitrogen at room temperature. After 20 hours water (25 mL) was added, the aqueous phase separated and washed with ethyl acetate (2×25 mL). The combined organic extracts were washed with brine, dried over sodium sulfate and evaporated. Chromatography (40 g silica cartridge, 0-100% ethyl acetate/petroleum benzine 40-60° C.) gave the title compound (I38) (708 mg, 85%) as a pink solid; $^1$H NMR (400 MHz, CDCl$_3$) δ 7.72 (s, 1H), 7.44-7.28 (m, 7H), 6.43 (s, 1H), 5.20 (s, 2H), 2.54 (q, J=7.6 Hz, 2H), 1.21 (t, J=7.6 Hz, 3H). LCMS Method C: rt 6.46 min; m/z 258.0 [M-PhCH$_2$O+CH$_3$OH]$^+$.

(c) tert-Butyl 4-(4-(((benzyloxy)carbonyl)amino)-3-ethylphenyl)-5,6-dihydropyridine-1(2H)-carboxylate (I39)

Potassium carbonate (215 mg, 1.55 mmol) the tert-butyl 4-(4,4,5,5-tetramethyl-1,3,2-dioxaborolan-2-yl)-5,6-dihydropyridine-1(2H)-carboxylate (I37) (160 mg, 0.517 mmol), benzyl (4-bromo-2-ethylphenyl)carbamate (I34) (182 mg, 0.543 mmol), PdCl$_2$(dppf)-DCM solvate (22 mg, 5 mol %) and DMF (5 mL) were loaded into a Schlenk tube, and degassed with 3× vacuum/nitrogen cycles. The mixture was brought to 80° C. under nitrogen then after 18 hours cooled and poured into water (100 mL). DCM (75 mL) and brine (50 mL) were added, the aqueous phase was washed with further DCM (2×75 mL), and the combined DCM extracts washed with brine, dried and evaporated. Chromatography (40 g silica cartridge, 0-80% ethyl acetate/petroleum benzine 40-60° C.) gave the title compound (I39) (129 mg, 57% yield) as a colourless oil; $^1$H NMR (400 MHz, CDCl$_3$) δ 7.77 (s, 1H), 7.45-7.31 (m, 5H), 7.22 (dd, J=8.5, 2.1 Hz, 1H), 7.18 (d, J=2.1 Hz, 1H), 6.48 (s, 1H), 5.99 (s, 1H), 5.21 (s, 2H), 4.06 (d, J=2.5 Hz, 2H), 3.63 (t, J=5.7 Hz, 2H), 2.58 (q, J=7.6 Hz, 2H), 2.50 (s, 2H), 1.49 (s, 9H), 1.22 (t, J=7.6 Hz, 3H). LCMS Method C: rt 6.67 min; m/z 337.1 [M-Boc+2H]$^+$, 381.1 [M-tBu+2H]$^+$.

(d) tert-Butyl 4-(4-amino-3-ethylphenyl)piperidine-1-carboxylate (I40)

tert-Butyl 4-(4-(((benzyloxy)carbonyl)amino)-3-ethylphenyl)-5,6-dihydropyridine-1(2H)-carboxylate (I39) (0.500 g, 1.14 mmol) was dissolved in ethanol (20 mL), and a slurry of 10% Pd/C (0.25 g) in ethanol (2 mL) was added. The mixture was stirred under hydrogen for 18 hours, then filtered through celite, washing the celite with ethanol (30 mL). The combined filtrates were evaporated, and chromatography (12 g silica cartridge, 0-80% ethyl acetate/petroleum benzine 40-60° C.) gave the title compound (I40) (0.212 g, 61% yield) as a pink syrup; $^1$H NMR (400 MHz, CDCl$_3$) δ 6.90 (d, J=2.0 Hz, 1H), 6.87 (dd, J=8.0, 2.1 Hz, 1H), 6.63 (d, J=8.0 Hz, 1H), 4.21 (s, 2H), 3.55 (s, 2H), 2.78 (t, J=12.2 Hz, 2H), 2.59-2.46 (m, 3H), 1.78 (d, J=13.2 Hz, 2H), 1.66-1.53 (m, overlaps with water), 1.48 (s, 9H), 1.25 (t, J=7.5 Hz, 3H). LCMS Method C: rt 5.33 min; m/z 249.2 [M-tBu+2H]$^+$, 205.2 [M-Boc+2H]$^+$.

(e) tert-Butyl 4-(4-((4-chloro-5-(trifluoromethyl)pyrimidin-2-yl)amino)-3-ethylphenyl)piperidine-1-carboxylate (I41)

A solution of 2,4-dichloro-5-(trifluoromethyl)pyrimidine (166 mg, 0.766 mmol) in 1:1 DCE: t-BuOH (5 mL) was stirred at 0° C. under nitrogen. 1.0 M Zinc(II) chloride in ether (0.77 mL, 0.77 mmol) was added and the mixture stirred for one hour. tert-Butyl 4-(4-amino-3-ethylphenyl)piperidine-1-carboxylate (I40) (212 mg, 0.70 mmol) in 1:1 DCE: t-BuOH (5 mL) was added dropwise, and after 30 minutes triethylamine (146 μL, 1.05 mmol) in 1:1 DCE: t-BuOH (5 mL) was added and the mixture allowed to slowly come to room temperature. After 18 hours the mixture was concentrated, and chromatography (12 g silica cartridge, 0-50% ethyl acetate/cyclohexane) gave the title compound (I41) (283 mg, 84% yield) as a pale pink solid; $^1$H NMR (400 MHz, CDCl$_3$) δ 8.51 (d, J=0.6 Hz, 1H), 7.60 (d, J=8.3 Hz, 1H), 7.15-7.07 (m, 3H), 4.25 (s, 2H), 2.80 (t, J=12.1 Hz, 2H), 2.69-2.59 (m, 3H), 1.83 (d, J=12.9 Hz, 2H), 1.69-1.59 (m, 2H), 1.49 (s, 9H), 1.23 (t, J=7.6 Hz, 3H). LCMS Method C: rt 6.94 min; m/z 429.1 [M-tBu+2H]$^+$, 385.1 [M-Boc+2H]$^+$; m/z 483.1 [M−H]$^-$.

(f) tert-Butyl 4-(3-ethyl-4-((4-((2-(2-methoxy-2-oxoethyl)phenyl)ethynyl)-5-(trifluoromethyl)pyrimidin-2-yl-amino)phenyl)piperidine-1-carboxylate (I42)

A mixture of tert-butyl 4-(4-((4-chloro-5-(trifluoromethyl)pyrimidin-2-yl)amino)-3-ethylphenyl)piperidine-1-carboxylate (I41) (283 mg, 0.584 mmol), methyl 2-(2-ethynylphenyl)acetate (I4) (122 mg, 0.700 mmol), copper(I) iodide (17 mg, 15 mol %), triphenylphosphine (23 mg, 15 mol %), bis(triphenylphosphine)palladium(II) chloride (41 mg, 10 mol %), triethylamine (0.33 mL, 2.3 mmol) and DMF (3 mL) was degassed with a nitrogen then heated under microwave irradiation (120° C./15 min). The cooled mixture was poured into water (30 mL) and extracted with ethyl acetate (3×25 mL). The combined organic extracts were washed with brine (2×50 mL), dried over sodium sulfate and evaporated. Chromatography (12 g silica cartridge, 0-80% ethyl acetate/petroleum benzine 40-60° C.) gave the title compound (I42) (311 mg, 86% yield) as a brown oil; $^1$H NMR (400 MHz, CDCl$_3$) δ 8.57 (s, 1H), 7.73-7.65 (m, 2H), 7.46-7.28 (m), 7.15-7.08 (m), 4.25 (s, 2H), 3.95 (s, J=9.6 Hz, 2H), 3.70 (s, 3H), 2.80 (t, J=12.1 Hz, 2H), 2.70-2.59 (m, 3H), 1.84 (d, J=12.9 Hz, 2H), 1.65 (td, J=12.8, 4.1 Hz, 2H), 1.49 (s, 9H), 1.25 (t, J=7.6 Hz, 3H). LCMS: rt 7.01 min; m/z 623.1 [M+H]$^+$; 567.1 [M-tBu+2H]$^+$, 523.1 [M-Boc+2H]$^+$; m/z 621.2 [M−H]$^-$.

(g) tert-Butyl 4-(3-ethyl-4-((4-(2-(2-methoxy-2-oxoethyl)phenethyl)-5-(trifluoromethyl)pyrimidin-2-yl)-amino)phenyl)piperidine-1-carboxylate (I43)

tert-Butyl 4-(3-ethyl-4-((4-((2-(2-methoxy-2-oxoethyl)phenyl)ethynyl)-5-(trifluoromethyl)pyrimidin-2-yl)amino)phenyl)piperidine-1-carboxylate (I42) (311 mg, 0.499 mmol) was dissolved in ethanol (20 mL), and a slurry of Pd/C (150 mg) in ethanol (2 mL) was added. The mixture was stirred under hydrogen for 18 hours, filtered through celite, washing the celite with ethanol (20 mL) and the filtrate concentrated. The mixture was taken up in ethanol (20 mL), and a slurry of Pd/C (150 mg) in ethanol (2 mL) was added followed by triethylamine (20 μL). The mixture was stirred under hydrogen for 18 hours, filtered through celite, the celite washed with ethanol (10 mL) and the combined filtrates evaporated. The residue was taken up in DMF (10 mL), a slurry of Pd/C (150 mg) in DMF (2 mL) was added and the mixture stirred under hydrogen. After 16 hours the mixture was filtered through celite, and the celite washed with ethyl acetate (100 mL). The combined filtrate was evaporated to give a pale green oil. Chromatography (12 g silica cartridge, 0-60% ethyl acetate/petroleum benzine 40-60° C.) gave the title compound (I43) (177.1 mg, 57% yield) as a pale yellow oil. $^1$H NMR (400 MHz, CDCl$_3$) δ 8.49 (d, J=0.5 Hz, 1H), 7.73 (d, J=8.1 Hz, 1H), 7.25-7.16 (m, 4H), 7.12-7.07 (m, 2H), 7.06 (s, 1H), 4.25 (br s, 2H), 3.72 (s, 2H), 3.67 (s, 3H), 3.14-3.01 (m, 4H), 2.81 (t, J=12.2 Hz, 2H), 2.72-2.59 (m, 3H), 1.84 (d, J=13.0 Hz, 2H), 1.69-1.56 (m, overlaps with water in solvent), 1.49 (s, 9H), 1.26 (t, J=7.1 Hz, 3H). LCMS: rt 7.16 min; m/z 627.2 [M+H]$^+$; 571.1 [M-tBu+2H]$^+$; m/z 625.2 [M−H]$^-$.

(h) tert-Butyl 4-(4-((4-(2-(2-amino-2-oxoethyl)phenethyl)-5-(trifluoromethyl)pyrimidin-2-yl)amino)-3-ethylphenyl)piperidine-1-carboxylate (I44)

tert-Butyl 4-(3-ethyl-4-((4-(2-(2-methoxy-2-oxoethyl)phenethyl)-5-(trifluoromethyl)pyrimidin-2-yl)amino)phenyl)piperidine-1-carboxylate (I43) (177 mg, 0.282 mmol) was dissolved in THF (10 mL), and a solution of lithium hydroxide monohydrate (59.0 mg, 1.41 mmol) in water (2 mL) was added. The mixture was stirred for 18 hours then concentrated. The residue was suspended in saturated sodium bicarbonate (20 mL), and extracted with ethyl acetate (3×20 mL). The combined ethyl acetate phases were washed with brine, dried (sodium sulphate) and evaporated. The residue was dissolved in THF (10 mL) and DMF (1 mL) at 30° C. and HOBt (50 mg, 0.37 mmol), EDCl (65 mg, 0.37 mmol) and DIPEA (0.246 mL, 1.41 mmol) were added. After ten minutes ammonium carbonate (135 mg, 1.41 mmol) was added and the mixture was stirred for 18 hours at 30° C. The mixture was concentrated, the residue diluted with saturated sodium bicarbonate (25 mL) and extracted with ethyl acetate (3×25 mL). The combined ethyl acetate phases were washed with brine (25 mL), dried (sodium sulfate) and evaporated. Chromatography (12 g silica cartridge, 0-100% ethyl acetate/petroleum benzine 40-60° C.) gave the title compound (I44) (122 mg, 71% over two steps) as a white solid; $^1$H NMR (400 MHz, CDCl$_3$) δ 8.49 (s, 1H), 7.56 (d, J=8.1 Hz, 1H), 7.28-7.22 (m, overlaps with CHCl$_3$), 7.22-7.15 (m, 1H), 7.13-7.05 (m, 3H), 5.38 (s, 1H), 5.15 (s, 1H), 4.25 (s, 2H), 3.64 (s, 2H), 3.11-2.99 (m, 4H), 2.80 (t, J=12.1 Hz, 2H), 2.69-2.60 (m, 3H), 1.84 (d, J=12.3 Hz, 2H), 1.69-1.60 (m, 2H), 1.49 (s, 9H), 1.23 (t, J=7.6 Hz, 3H). LCMS: rt 6.65 min; m/z 612.2 [M+H]$^+$, 556.1 [M-tBu+2H]$^+$; m/z 610.2 [M−H]$^−$.

(i) 2-(2-(2-(2-((2-Ethyl-4-(piperidin-4-yl-phenyl-amino)-5-(trifluoromethyl)pyrimidin-4-yl)ethyl)phenyl)acetamide (8)

tert-Butyl 4-(4-((4-(2-(2-amino-2-oxoethyl)phenethyl)-5-(trifluoromethyl)pyrimidin-2-yl)amino)-3-ethylphenyl)piperidine-1-carboxylate (I44) (120 mg, 0.20 mmol) was dissolved in DCM (20 mL), TFA (2 mL) was added and the mixture stirred for 16 hours at room temperature. The mixture was concentrated and the residue suspended in 10% sodium hydroxide (10 mL) and brine (10 mL). The mixture was extracted with ethyl acetate (4×20 mL), the combined extracts washed with brine, dried (sodium sulphate) evaporated and the residue evaporated for ether to give the title compound (8) (93 mg, 93% yield) as a white solid; $^1$H NMR (400 MHz, d$_6$-DMSO) δ 9.47 (s, 1H), 8.49 (s, 1H), 7.37 (s, 1H), 7.26-7.18 (m, 2H), 7.17-7.09 (m, 4H), 7.05 (dd, J=8.2, 1.9 Hz, 1H), 6.89 (s, 1H), 3.44 (s, 2H), 3.09-2.88 (m, 6H), 2.62-2.54 (m, overlaps with DMSO), 1.70 (d, J=11.4 Hz, 2H), 1.52 (qd, J=12.3, 3.7 Hz, 2H), 1.10 (t, J=7.5 Hz, 3H). LCMS Method C, 4.96 min; m/z 512.2 [M+H]$^+$, 534.2 [M+Na]$^+$; m/z 510.2 [M−H]$^−$.

Example 9

2-(2-(2-(2-((2-Ethyl-4-(1-methylpiperidin-4-yl)phenyl)amino)-5-(trifluoromethyl)pyrimidin-4-yl)ethyl)phenyl)acetamide (9)

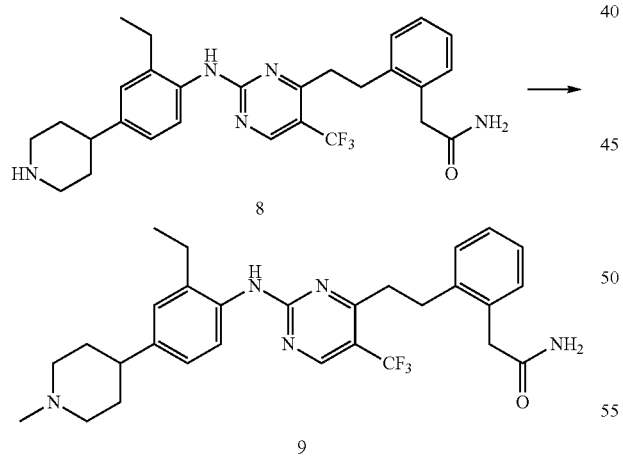

2-(2-(2-(2-((2-Ethyl-4-(piperidin-4-yl)phenyl)amino)-5-(trifluoromethyl)pyrimidin-4-yl)ethyl)phenyl)acetamide (8) (84 mg, 0.16 mmol) was dissolved in methanol (8 mL), 37% formaldehyde solution (53 μl, 0.66 mmol) was added and the mixture stirred for ten minutes at room temperature. Sodium tris(acetoxy)borohydride (174 mg, 0.821 mmol) was added, and after two hours the mixture was concentrated. The residue was diluted with 10% sodium hydroxide (15 mL) and brine (15 mL), and the mixture extracted with ethyl acetate (4×25 mL). The combined ethyl acetate phases were washed with brine, dried over sodium sulfate, evaporated and the residue evaporated from DCM to give the title compound (9) (72 mg, 84% yield) as a white solid; $^1$H NMR (400 MHz, d$_6$-DMSO) δ 9.46 (s, 1H), 8.49 (s, 1H), 7.36 (s, 1H), 7.21 (t, J=4.6 Hz, 2H), 7.18-7.10 (m, 4H), 7.06 (dd, J=8.2, 1.6 Hz, 1H), 6.88 (s, 1H), 3.44 (s, 2H), 3.07-2.90 (m, 4H), 2.86 (d, J=11.3 Hz, 2H), 2.57 (q, J=7.5 Hz, 2H), 2.48-2.37 (m, 1H), 2.19 (s, 3H), 2.02-1.89 (m, 2H), 1.79-1.59 (m, 4H), 1.09 (t, J=7.5 Hz, 3H). LCMS Method C: rt 5.04 min; m/z 526.2 [M+H]$^+$; m/z 524.2 [M−H]$^−$.

Example 10

2-(2-(2-(2-((4-(Piperidin-4-yl)-2-(trifluoromethoxy)phenyl)amino)-5-(trifluoromethyl)pyrimidin-4-yl)ethyl)phenyl)acetamide (10)

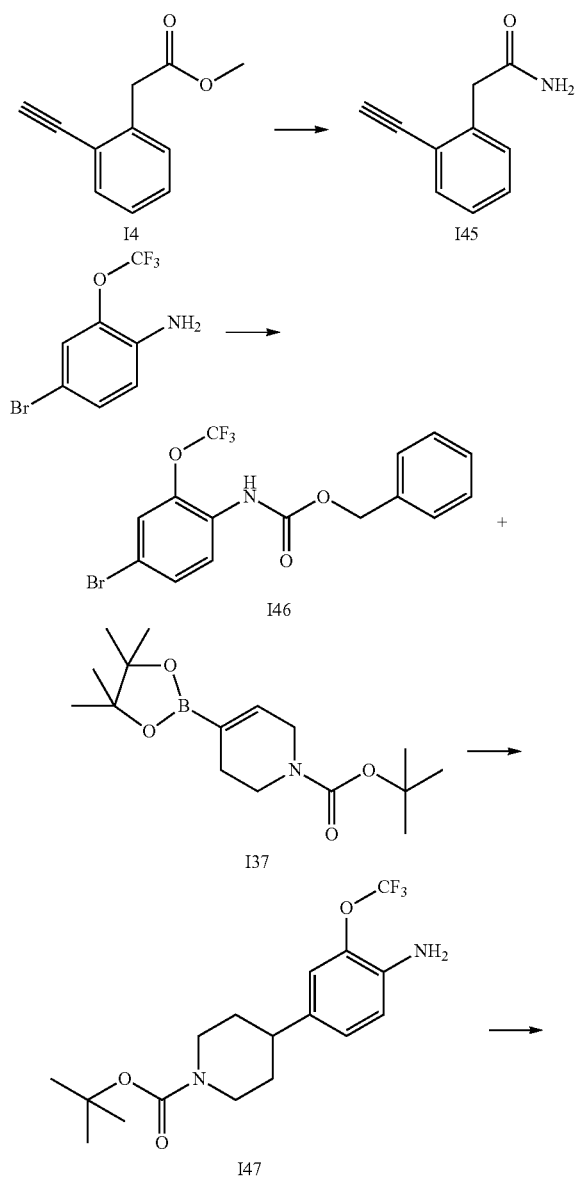

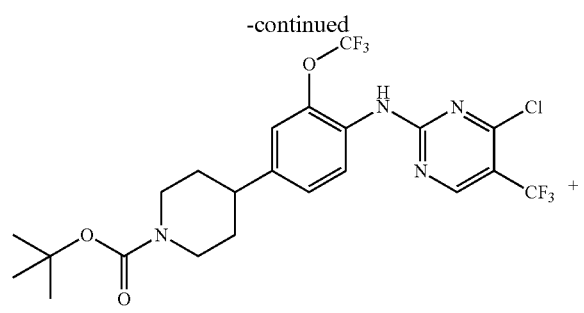

148

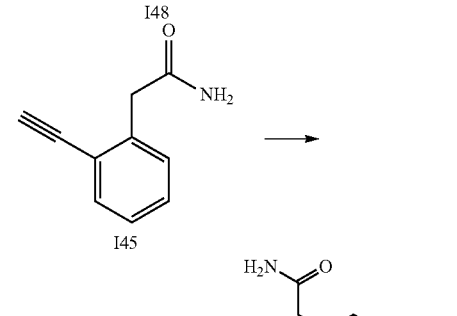

I45

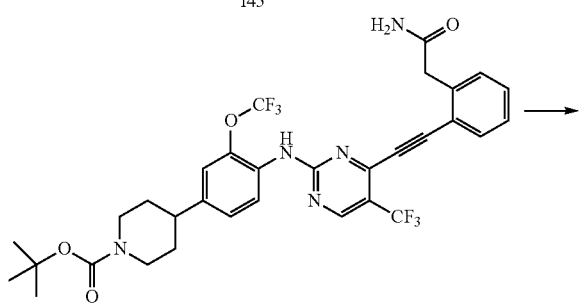

I49

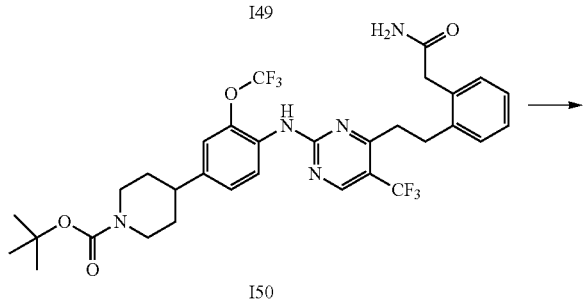

I50

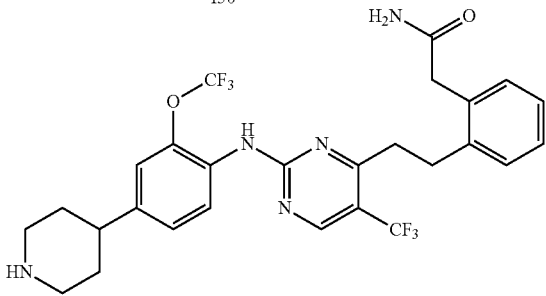

10

(a) 2-(2-Ethynylphenyl)acetamide (I45)

To a stirred solution of methyl 2-(2-ethynylphenyl)acetate (14) (0.200 g, 1.15 mmol) in methanol (2 mL) at 0° C. in a thick-walled Schlenk tube was added magnesium nitride (0.290 g, 2.87 mmol) in a single portion. The tube was sealed immediately and allowed to warm to room temperature in a water bath over 1 hour and then heated at 80° C. for 22 hours. After cooling to room temperature the resulting mixture was diluted with EtOAc (100 mL) and saturated aqueous NaHCO$_3$ (80 mL). The layers were separated and the aqueous layer was extracted with EtOAc (80 mL), neutralised with 2 M aq. HCl and extracted with EtOAc (2×80 mL). The organic layers were combined, washed with brine (100 mL), dried (MgSO$_4$), filtered and concentrated in vacuo to give a yellow solid. Silica gel chromatography (40 g Si Cartridge, 0-50% EtOAc in dichloromethane) gave the title compound (145) (0.093 g, 51% yield) as a white solid; $^1$H NMR (400 MHz, d$_6$-DMSO) δ 7.44 (dd, J=7.6, 1.0 Hz, 1H), 7.40-7.28 (m, 3H), 7.24 (td, J=7.4, 1.7 Hz, 1H), 6.93 (s, 1H), 4.32 (s, 1H), 3.59 (s, 2H). LCMS Method C: rt 4.68 min; m/z 160.2 [M+H]$^+$.

(b) Benzyl(4-bromo-2-(trifluoromethoxy)phenyl)carbamate (I46)

4-Bromo-2-(trifluoromethoxy)aniline (1.0 g, 3.9 mmol) was dissolved in dry toluene (25 mL), sodium carbonate (0.621 g, 5.86 mmol) and benzyl chloroformate (0.669 mL, 4.69 mmol) was added and the mixture stirred under nitrogen at room temperature for 22 hours. The reaction was then heated to 80° C. and stirred at this. temperature for 17 hours and then heated further to reflux and stirred for 22 hours. Water (100 mL) was added to the coiled mixture, the aqueous phase separated and washed with ethyl acetate (2×100 mL). The combined organic extracts were washed with 0.5 M aq. citric acid (70 mL), water (70 mL), brine (70 mL), dried (MgSO$_4$), filtered and concentrated in vacuo to give a pink solid. The crude material was purified by silica gel chromatography (40 g Si cartridge, 0-20% EtOAc in 40-60° C. petroleum benzine) to give the title compound (146) (1.153 g, 76% yield) as a white solid; $^1$H NMR (400 MHz, CDCl$_3$) δ 8.15 (d, J=8.7 Hz, 1H), 7.44-7.36 (m, 7H), 6.95 (s, 1H), 5.22 (s, 2H). LCMS Method C: rt 6.67 min; m/z 389.9 [M−H]$^-$.

(c) tert-Butyl 4-(4-amino-3-(trifluoromethoxy)phenyl)piperidine-1-carboxylate (I47)

A solution of 2 M aq. Na$_2$CO$_3$ (1.85 mL, 3.70 mmol) was added to a mixture of tort-butyl 4-(4,4,5,5-tetramethyl-1,3,2-dioxaborolan-2-yl)-5,6-dihydropyridine-1(2H)-carboxylate (137) (~50% pure, 0.915 g, 1.480 mmol), benzyl (4-bromo-2-(trifluoromethoxy)phenyl)carbamate (I46) (0.635 g, 1.63 mmol), LiCl (0.125 g, 2.96 mmol), Pd(PPh$_3$)$_2$Cl$_2$ (0.052 g, 0.074 mmol) and TBAB (0.048 g, 0.15 mmol) in dry 1,4-dioxane (15 mL). The reaction mixture was stirred at 80° C. for 17 hours, then filtered through celite, which was washed with EtOAc and MeOH and the filtrate was concentrated in vacuo to give a pale yellow gum. The crude material was purified by silica gel chromatography (40 g Si Cartridge, 0-15% EtOAc in petroleum benzine 40-60° C.) to give a pale yellow gum (0.515 g). To a solution of the intermediate in EtOAc (20 mL) was added 10% Pd/C (80 mg) in EtOAc (5 mL). The reaction was then stirred at room temperature for 18 hours under an atmosphere of hydrogen and then filtered through a pad of celite, which was washed with EtOAc (100 mL). The solvent was removed in vacuo to give crude product which was purified by silica gel chromatography (40 g Si Cartridge, 0-30% EtOAc in petroleum benzine 40-60° C.) to give the title compound (147) (80% purity, 0.220 g, 33% yield over 2 steps) as a pale yellow gum; $^1$H NMR (400 MHz, CDCl$_3$) δ 6.98-6.95 (m, 1H), 6.92 (dd, J=8.2, 1.8 Hz, 1H), 6.74 (d, J=8.2 Hz, 1H), 4.30-4.13 (m, 2H), 3.77 (s, 2H), 2.77 (t, J=12.5 Hz, 2H), 2.54 (tt, J=12.1, 3.5 Hz, 1H), 1.78 (d, J=13.1 Hz, 2H), 1.57-1.50 (m, 2H, obscured by water signal), 1.48 (s, 9H).

(d) tert-Butyl 4-(4-((4-chloro-5-(trifluoromethyl) pyrimidin-2-yl)-amino)-3-(trifluoromethoxy)phenyl) piperidine-1-carboxylate (I48)

2,4-Dichloro-5-(trifluoromethyl)pyrimidine (0.110 g, 0.506 mmol) was stirred in a 1:1 t-BuOH:1,2-dichloroethane mixture (10 mL) at 0° C. A 1.0 M ZnCl₂ solution in diethyl ether (0.578 mL, 0.578 mmol) was added cautiously, after addition the reaction was left stirring at 0° C. for 30 minutes. A solution of tert-butyl 4-(4-amino-3-(trifluoromethoxy) phenyl)piperidine-1-carboxylate (I47) (impure, ~80% pure, 0.217 g, 0.482 mmol) in 1:1 t-BuOH:1,2-dichloroethane (5 mL) was added drop-wise at 0° C. followed by a solution of NEt₃ (0.081 mL, 0.58 mmol) in 1:1 t-BuOH:1,2-dichloroethane (5 mL) and the reaction was allowed to warm to room temperature and was stirred for 18 hours, then at 60° C. for 24 hours. The organic solvents were evaporated in vacuo and the crude gum was purified by silica gel chromatography (40 g Si cartridge, 0-40% EtOAc In petroleum benzine 40-60° C.) to give the title compound (I48) (0.085 g, 33% yield) as a pale yellow oily solid; ¹H NMR (400 MHz, d₆-DMSO) δ 10.38 (s, 1H), 8.72 (s, 1H), 7.52 (d, J=8.1 Hz, 1H), 7.33-7.29 (m, 2H), 4.13-4.04 (m, 2H), 2.88-2.72 (m, 3H), 1.79 (d, J=12.1 Hz, 2H), 1.56-1.44 (m, 2H), 1.42 (s, 9H). LCMS Method C: it 7.02 min; m/z 539.0, 541.0 [M−H]⁻.

(e) tert-Butyl 4-(4-((4-((2-(2-amino-2-oxoethyl)phenyl)ethynyl)-5-(trifluoromethyl)pyrimidin-2-yl) amino)-3-(trifluoromethoxy)phenyl)piperidine-1-carboxylate (I49)

To a nitrogen de-gassed solution of 2-(2-ethynylphenyl) acetamide (I41) (0.029 g, 0.18 mmol) and tert-butyl 4-(4-((4-chloro-5-(trifluoromethyl)pyrimidin-2-yl)amino)-3-(trifluoromethoxy)phenyl)piperidine-1-carboxylate (I48) (0.082 g, 0.15 mmol) in dry DMF (4 mL) were added triethylamine (0.085 mL, 0.61 mmol), triphenylphosphine (6.0 mg, 0.023 mmol), trans-dichlorobis (triphenylphosphine)palladium (II) (0.011 g, 0.015 mmol) and Cu(I)I (4.0 mg, 0.023 mmol). The reaction mixture was heated under microwave irradiation at 120° C. for 20 minutes, concentrated to dryness in vacuo and purified by silica gel chromatography (12 g Si cartridge, 0-100% EtOAc in petroleum benzine 40-60° C.) to give the title compound (I49) (0.073 g, 73% yield) as a pale yellow solid; ¹H NMR (400 MHz, d₆-DMSO) δ 10.11 (s, 1H), 8.74 (s, 1H), 7.58 (dd, J=7.7, 6.2 Hz, 2H), 7.53-7.47 (m, 1H), 7.42-7.27 (m, 5H), 6.99 (s, 1H), 4.14-4.03 (m, 2H), 3.67 (s, 2H), 2.87-2.72 (m, 3H), 1.79 (d, J=12.8 Hz, 2H), 1.50 (qd, J=12.5, 4.1 Hz, 2H), 1.42 (s, 9H). LCMS Method C: rt 6.63 min; m/z 564.0 [M−Boc+2H]⁺.

(f) tert-Butyl 4-(4-((4-(2-(2-amino-2-oxoethyl)phenethyl)-5-(trifluoromethyl)pyrimidin-2-yl)amino)-3-(trifluoromethoxy)phenyl)piperidine-1-carboxylate (I50)

tert-Butyl 4-(4-((4-((2-(2-amino-2-oxoethyl)phenyl)ethynyl)-5-(trifluoromethyl)pyrimidin-2-yl)amino)-3-(trifluoromethoxy)phenyl)piperidine-1-carboxylate (I49) (72.0 mg, 0.108 mmol) was dissolved in dry DMF (7 mL) under an atmosphere of nitrogen, and a slurry of 10% Pd(OH)₂/C (0.050 g) in EtOAc (2 mL) was added. The mixture then was stirred vigorously under hydrogen for 24 hours. Upon completion, the reaction was filtered through a pad of celite, which was washed with EtOAc (40 mL). The combined filtrates were concentrated in vacuo to give a pale yellow oil. The crude product was purified by silica gel chromatography (12 g Si Cartridge, 0-100% EtOAc in petroleum benzine 40-60° C.) to give the title compound (I50) (0.064 g, 88% yield) as an off-white solid; ¹H NMR (400 MHz, d₆-DMSO) δ 9.80 (s, 1H), 8.60 (s, 1H), 7.61 (d, J=8.1 Hz, 1H), 7.39 (s, 1H), 7.32-7.26 (m, 2H), 7.21 (dt, J=6.7, 3.4 Hz, 1H), 7.18-7.08 (m, 3H), 6.90 (s, 1H), 4.09 (d, J=12.1 Hz, 2H), 3.45 (s, 2H), 3.09-2.94 (m, 4H), 2.88-2.72 (m, 3H) 1.79 (d, J=12.3 Hz, 2H), 1.59-1.38 (m, 11H). LCMS Method C: rt 6.75 min, m/z 668.1 [M+H]⁺.

(g) 2-(2-(2-(2-((4-(Piperidin-4-yl)-2-(trifluoromethoxy)phenyl)amino)-5-(trifluoromethyl)pyrimidin-4-yl)ethyl)phenyl)acetamide (10)

tert-Butyl 4-(4-((4-(2-(2-amino-2-oxoethyl)phenethyl)-5-(trifluoromethyl)pyrimidin-2-yl)amino)-3-(trifluoromethoxy)phenyl)piperidine-1-carboxylate (I50) (0.062 g, 0.093 mmol) was dissolved in dry DCM (6 mL) under an atmosphere of nitrogen. Trifluoroacetic acid (0.142 mL, 1.86 mmol) was added to the solution and the reaction was stirred at room temperature for 20 hours. Volatiles were removed in vacuo, EtOAc (50 mL) and 2 M aq. NaOH (50 mL) were added to the residue and the layers were separated. The aqueous layer was extracted with EtOAc (2×70 mL), the combined organics were washed with water (50 mL), brine (50 mL), dried (MgSO₄), filtered and concentrated in vacuo to give an off-white solid. The crude material was purified by silica gel chromatography (12 g Si Cartridge, 0-100% EtOAc in petroleum benzine 40-60° C., then 0-100% methanol in EtOAc, then 1% ammonia in methanol), to give the title compound (10) (0.042 g, 80% yield) as a white solid; ¹H NMR (400 MHz, d₆-DMSO) δ 9.78 (s, 1H), 8.59 (s, 1H), 7.59 (d, J=8.3 Hz, 1H), 7.39 (s, 1H), 7.29-7.17 (m, 3H), 7.18-7.06 (m, 3H), 6.90 (s, 1H), 3.45 (s, 2H), 3.09-2.92 (m, 6H), 2.71-2.53 (m, 3H), 1.71 (d, J=11.7 Hz, 2H), 1.49 (qd, J=12.1, 3.7 Hz, 2H). LCMS Method C: rt 5.07 min; m/z 568.1[M+H]⁺.

Example 11

2-(2-(2-(2-((4-(1-Methylpiperidin-4-yl)-2-(trifluoromethoxy)phenyl)amino)-5-(trifluoromethyl)pyrimidin-4-yl)ethyl)phenyl)acetamide (11)

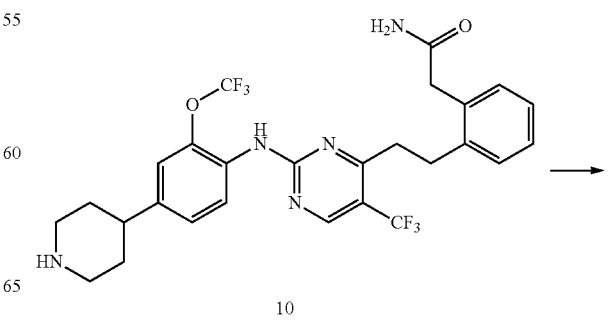

10

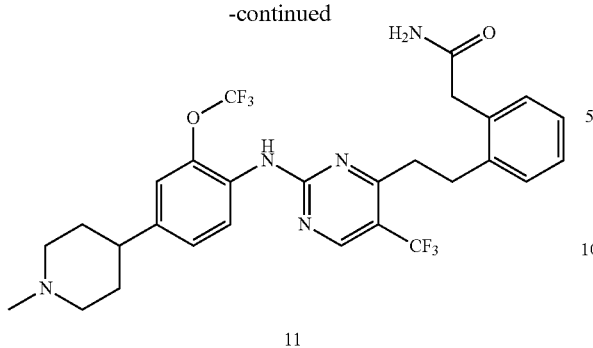

11

To a suspension of 2-(2-(2-(2-((4-(piperidin-4-yl)-2-(trifluoromethoxy)phenyl)amino)-5-(trifluoromethyl)pyrimidin-4-yl)ethyl)phenyl)acetamide (10) (0.039 g, 0.069 mmol) in anhydrous methanol (4 mL) was added a 37% aq. solution of formaldehyde (0.020 mL, 0.28 mmol) under an atmosphere of nitrogen followed by sodium triacetoxyborohydride (0.073 g, 0.34 mmol). The reaction was stirred at room temperature for 3 hours. The volatiles were then removed in vacuo and the residue was diluted with EtOAc (50 mL) and sat. aq. NaHCO$_3$ (30 mL). The layers were separated and the aqueous layer was extracted with EtOAc (2×30 mL), the combined organic layers were washed with brine (40 mL), dried (MgSO$_4$), filtered and concentrated in vacuo to give a gum which was taken up in DCM (~10 mL) and methanol (~1 mL) and concentrated in vacuo. The process was repeated with only DCM twice. The resulting gum was then suspended in diethyl ether (5 mL) and the solvent was removed in vacuo. The procedure was repeated to give the title compound (I1) (0.037 g, 93% yield) as a white fluffy solid: $^1$H NMR (400 MHz, d$_r$ DMSO) δ 9.79 (s, 1H), 8.59 (s, 1H), 7.60 (d, J=8.3 Hz, 1H), 7.39 (s, 1H), 7.28 (dd, J=8.4, 1.9 Hz, 1H), 7.26-7.23 (m, 1H), 7.23-7.19 (m, 1H), 7.18-7.08 (m, 3H), 6.89 (s, 1H), 3.45 (s, 2H), 3.08-2.93 (m, 4H); 2.90-2.83 (m, 2H), 2.57-2.52 (m, 1H, obscured by residual solvent signal), 2.19 (s, 3H), 1.96 (td, J=11.5, 2.0 Hz, 2H), 1.80-1.72 (m, 2H), 1.65 (ddd, J=24.6, 12.4, 3.7 Hz, 2H). LCMS Method C: rt 5.11 min; m/z 582.1 [M+H]$^+$.

Example 12

2-(2-(2-(2-((2-methyl-4-(1-methylpiperidin-4-yl)phenyl)amino)-5-(trifluoromethyl)pyrimidin-4-yl)ethyl)phenyl)acetamide (12)

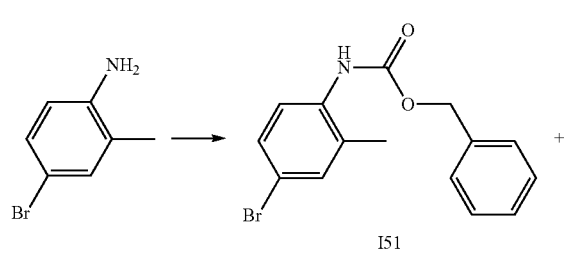

I51

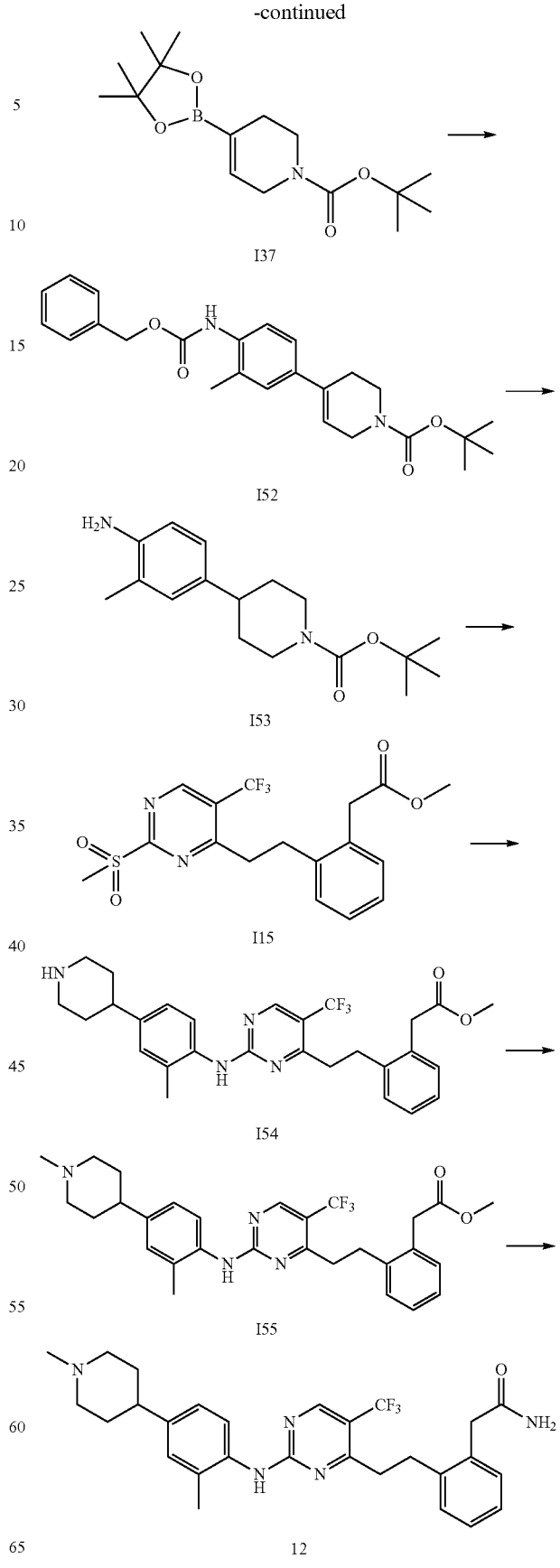

(a) Benzyl(4-bromo-2-methylphenyl)carbamate (I51)

2-Bromo-4-methylaniline (5.00 g, 26.9 mmol), benzyl chloroformate (5.75 mL, 40.3 mmol), $Na_2CO_3$ (4.27 g, 40.3 mmol) and toluene (100 mL) were stirred under nitrogen at room temperature for 20 hours. The resulting mixture was diluted with ethyl acetate and washed with water (100 mL). The organic layer was dried ($MgSO_4$) and the volatiles removed by evaporation under reduced pressure. Petroleum benzene 40-60° C. was added and the resulting precipitate collected by filtration to give the title compound (I51) as colourless needles (8.50 g, 99%); $^1H$ NMR (400 MHz, $CDCl_3$) δ 7.80-7.67 (m, 1H), 7.44-7.28 (m, 6H), 6.40 (s, 1H), 5.20 (s, 2H), 2.21 (s, 3H). LCMS Method C: rt 6.36 min; m/z 320 $[M+1]^+$.

(b) tert-Butyl 4-(4-(((benzyloxy)carbonyl)amino)-3-methylphenyl)-5,6-dihydropyridine-1(2H)-carboxylate (I52)

A suspension of benzyl (4-bromo-2-methylphenyl)carbamate (I51) (1.00 g, 3.12 mmol), tert-butyl 4-(4,4,5,5-tetramethyl-1,3,2-dioxaborolan-2-yl)-5,6-dihydropyridine-1(2H)-carboxylate (37) (1.16 g, 3.74 mmol), $PdCl_2$(dppf)-DCM complex (310 mg, 0.374 mmol) and potassium carbonate (1.29 g, 9.36 mmol) in DMF (30 mL) was stirred under nitrogen at 80° C. for 16 hours. The volatiles were evaporated under reduced pressure and the residue adsorbed onto silica gel. Chromatography on silica gel (0-30% ethyl acetate/petroleum benzine 40-60° C.) gave the title compound (I52) (949 mg, 72%) as a yellow liquid; $^1H$ NMR (400 MHz, $CDCl_3$) δ 7.83-7.70 (m, 1H), 7.41-7.34 (m, 5H), 7.21 (dd, J=8.5, 1.9 Hz, 1H), 7.16 (d, J=1.8 Hz, 1H), 6.56 (s, 1H), 5.97 (s, 1H), 5.20 (s, 2H), 4.05 (d, J=2.9 Hz, 2H), 3.61 (t, J=5.7 Hz, 2H), 2.48 (d, J=1.5 Hz, 2H), 2.23 (s, 3H), 1.50 (d, J=2.6 Hz, 9H).

(c) tert-Butyl 4-(4-amino-3-methylphenyl)piperidine-1-carboxylate (I53)

A suspension of tert-butyl 4-(4-(((benzyloxy)carbonyl)amino)-3-methylphenyl)-5,6-dihydropyridine-1(2H)-carboxylate (I52) (798 mg, 2.49 mmol) and 10% Pd/C (250 mg) in MeOH (50 mL) was stirred under hydrogen (1 atm) for 16 hours at room temperature. The resulting mixture was filtered through celite, washing with MeOH, then the volatiles were removed by evaporation under reduced pressure to give the title compound (I53) (550 mg, 76%) as a purple/brown liquid; $^1H$ NMR (400 MHz, $CDCl_3$) δ 6.95 (d, J=6.7 Hz, 3H), 4.22 (s, 2H), 2.77 (s, 2H), 2.54 (s, 1H), 2.29 (s, 3H), 1.77 (d, J=12.7 Hz, 2H), 1.56 (dd, J=12.6, 3.7 Hz, 9H), 1.47 (s, 9H). LCMS Method C rt: 5.09 min; m/z 235.1 $[M-tBu+2]^+$, 191.2 $[M-Boc+2]^+$.

(d) Methyl 2-(2-(2-(2-((2-methyl-4-(piperidin-4-yl)phenyl)amino)-5-(trifluoromethyl)pyrimidin-4-yl)ethyl)phenyl)acetate (I54)

A solution of methyl 2-(2-(2-(2-(methylsulfonyl)-5-(trifluoromethyl)pyrimidin-4-yl)ethyl)phenyl)acetate (I15) (450 mg, 1.11 mmol), tert-butyl 4-(4-amino-3-methylphenyl)piperidine-1-carboxylate (I53) (390 mg, 1.34 mmol) and TFA (0.25 mL) in 2,2,2-TFE (3 mL) was heated at 120° C. under microwave irradiation for 30 minutes. The resulting mixture was adsorbed onto silica gel and chromatographed (0-50% MeOH/DCM) to give the title compound (I54) (478 mg, 83%) as a viscous liquid; $^1H$ NMR (400 MHz, $CDCl_3$) δ 9.14 (bs, 1H), 8.76 (bs, 1H), 8.51 (s, 1H), 7.58 (d, J=8.2 Hz, 1H), 7.21 (ddt, J=10.7, 7.4, 4.3 Hz, 4H), 7.15-7.06 (m, 1H), 3.65 (s, 2H), 3.60 (d, J=12.6 Hz, 2H), 3.49 (s, 3H), 3.15-3.02 (m, 6H), 2.87-2.71 (m, 1H), 2.32 (s, 3H), 2.07 (d, J=7.8 Hz, 4H). LCMS Method C: rt 5.24 min; m/z 513.2 $[M+1]^+$.

(e) Methyl 2-(2-(2-(2-((2-methyl-4-(1-methylpiperidin-4-yl)phenyl)amino)-5-(trifluoromethyl)pyrimidin-4-yl)ethyl)phenyl)acetate (I55)

Methyl 2-(2-(2-(2-((2-methyl-4-(piperidin-4-yl)phenyl)amino)-5-(trifluoromethyl)pyrimidin-4-yl)ethyl)phenyl)acetate (54) (1.10 g, 2.15 mmol) was dissolved in dry MeOH (20 mL) and formaldehyde solution (37% aq; 348 µL, 4.29 mmol) was added. Sodium triacetoxyborohydride (2.27 g, 10.7 mmol) was added under nitrogen and the resultant mixture was stirred at room temperature for 16 hours. Ethyl acetate (50 mL) was added and the mixture was washed with 10% $NaHCO_3$ solution (20 mL). The organic layer was separated, dried ($MgSO_4$) then the volatiles removed by evaporation under reduced pressure. Chromatography ($SiO_2$, 0-50% MeOH/DCM) gave the title compound (I55) (480 mg, 42%) as a cream solid; $^1H$ NMR (400 MHz, $CDCl_3$) δ 8.54 (s, 1H), 7.83-7.73 (m, 1H), 7.35 (s, 1H), 7.32-7.19 (m, 3H), 7.19-7.09 (m, 2H), 7.07-6.97 (m, 1H), 3.76 (s, 2H), 3.70 (s, 3H), 3.23 (d, J=11.5 Hz, 2H), 3.17-3.04 (m, 4H), 2.61-2.51 (m, 1H), 2.50 (s, 3H), 2.35 (s, 3H), 2.33-2.24 (m, 2H), 2.02-1.84 (m, 4H). LCMS Method C: rt 5.25 min; m/z 527.2 $[M+1]^+$.

(f) 2-(2-(2-(2-((2-Methyl-4-(1-methylpiperidin-4-yl)phenyl)amino)-5-(trifluoromethyl)pyrimidin-4-yl)ethyl)phenyl)acetamide (12)

Methyl 2-(2-(2-(2-((2-methyl-4-(1-methylpiperidin-4-yl)phenyl)amino)-5-(trifluoromethyl)pyrimidin-4-yl)ethyl)phenyl)acetate (I55) (476 mg, 0.906 mmol) and $LiOH.H_2O$ (113 mg, 2.71 mmol) in a mixture of THF (20 mL), water (4 mL) and MeOH (2 mL) were stirred at room temperature for 24 hours. The volatiles were evaporated under reduced pressure to give a light yellow solid which was dissolved in dry DMF (10 mL) and dry THF (10 mL). HOBT (171 mg, 1.26 mmol), EDCI (196 mg, 1.26 mmol), ammonium carbonate (458 mg, 4.87 mmol) and DIPEA (829 µL, 4.87 mmol) were added and the resulting mixture was stirred at room temperature for 16 hours. The volatiles were evaporated under reduced pressure and the residue taken up in ethyl acetate. The resulting solution was washed with 10% $NaHCO_3$, the layers separated and the organic layer was dried ($MgSO_4$). The volatiles were evaporated under reduced pressure and the residue chromatographed ($SiO_2$, 0-100% MeOH/DCM) to give the title compound (12) (358 mg, 52%) as a cream solid; $^1H$ NMR (400 MHz, $CDCl_3$) δ 8.51 (s, 1H), 7.58 (d, J=8.9 Hz, 1H), 7.34 (s, 1H), 7.28-7.19 (m, 4H), 7.14-7.09 (m, 2H), 5.66 (s, 1H), 5.49 (s, 1H), 3.65 (s, 2H), 3.13-3.04 (m, 4H), 3.04-2.97 (m, 2H), 2.54-2.41 (m, 1H), 2.35 (s, 3H), 2.30 (s, 3H), 2.08 (td, J=11.3, 3.8 Hz, 2H), 1.88-1.80 (m, 4H). LCMS Method C: rt 4.91 min; m/z 512.2 $[M+1]^+$, 510.2 $[M-1]^-$.

Example 13

2-(2-(2-(2-((2-Fluoro-4-(1-methylpiperidin-4-yl)phenyl)amino)-5-(trifluoromethyl)pyrimidin-4-yl)ethyl)phenyl)acetamide (13)

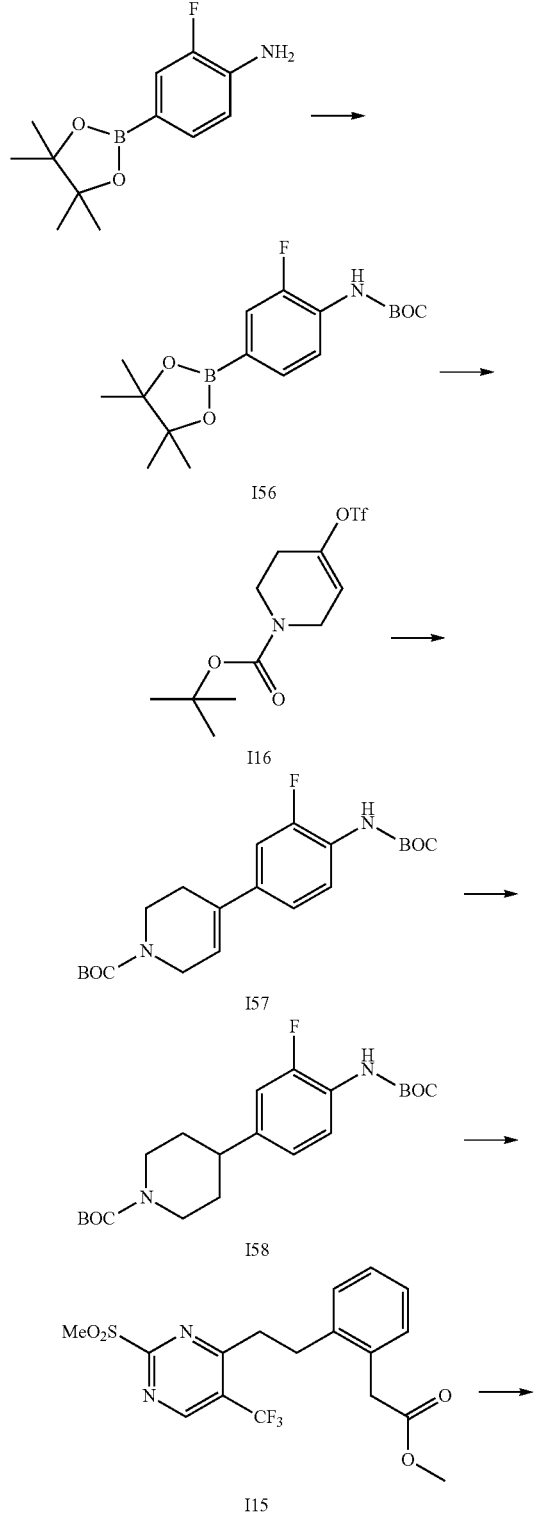

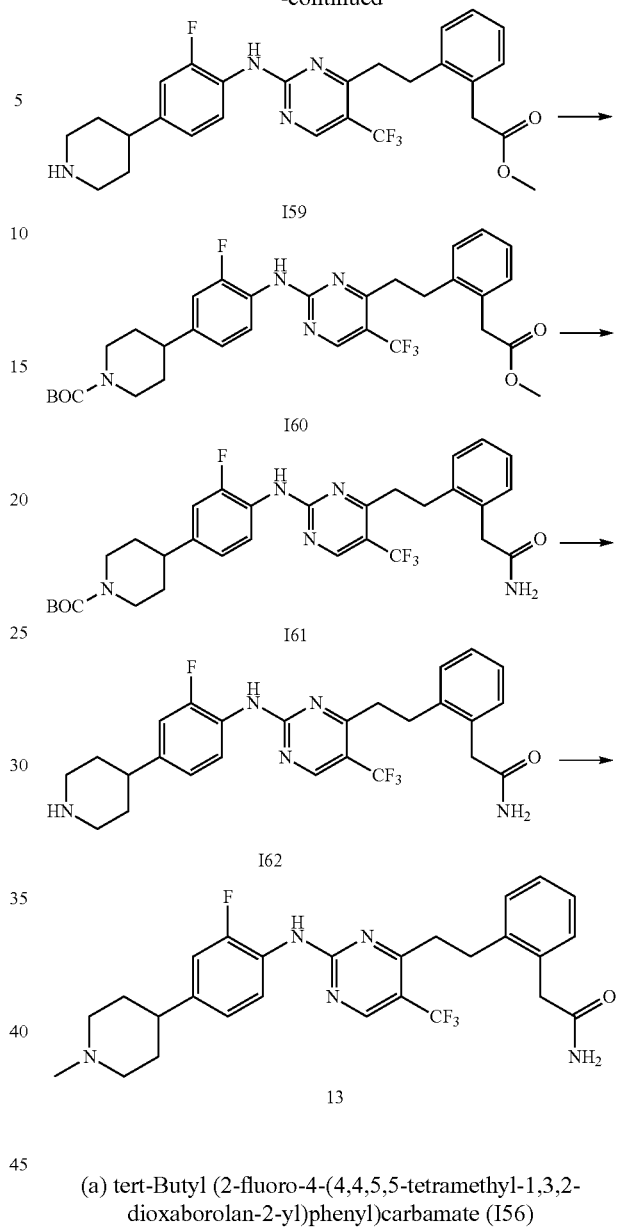

(a) tert-Butyl (2-fluoro-4-(4,4,5,5-tetramethyl-1,3,2-dioxaborolan-2-yl)phenyl)carbamate (I56)

A mixture of 2-fluoro-4-(4,4,5,5-tetramethyl-1,3,2-dioxaborolan-2-yl)aniline (1.00 g, 4.22 mmol) and Boc$_2$O (1.14 g, 5.21 mmol) in toluene (15 mL) was heated at reflux for 16 hours. A further portion of Boc$_2$O (1.04 g, 4.8 mmol) was added and the mixture heated for a further 20 hours then another portion of Boc$_2$O (1.4 g, 6.4 mmol) was added. After heating at reflux for a further 24 hours a catalytic amount of DMAP was added and the mixture heated at reflux for 30 minutes before concentrating under reduced pressure to give the title compound (56) (1.42 g, 99%); $^1$H NMR (400 MHz, CDCl$_3$) δ 7.52 (m, 2H), 7.14 (dd, J=7.5, 7.5 Hz, 1H), 1.40 (s, 12H), 1.35 (s, 9H).

(b) tert-Butyl 4-(4-((tert-butoxycarbonyl)amino)-3-fluorophenyl)-5,6-dihydropyridine-1(2H)-carboxylate (I57)

To a mixture of tert-butyl 4-(((trifluoromethyl)sulfonyl)oxy)-5,6-dihydropyridine-1(2H)-carboxylate (I16) (0.504 g, 1.52 mmol), tert-butyl (2-fluoro-4-(4,4,5,5-tetramethyl-1,3,2-dioxaborolan-2-yl)phenyl)carbamate (I62) (0.496 g, 1.47 mmol), and $PdCl_2(PPh_3)_2$ (0.055 g, 0.078 mmol) under a $N_2$ atmosphere was added dioxane (15 mL) and the mixture was bubbled with $N_2$ for 5 minutes before addition of 3.0 M aqueous sodium carbonate (1.5 mL, 4.5 mmol). The reaction was heated at reflux for 6 hours then concentrated under reduced pressure. The residue was chromatographed on silica gel (0-25% EtOAc/petroleum benzine 40-60° C.) to give the title compound (I57) (0.409 g, 71%); $^1$H NMR (400 MHz, $CDCl_3$) δ 7.12 (m, 3H), 6.09 (s, 1H), 4.08 (m, J=2.8 Hz, 2H), 3.63 (dd, J=5.6, 5.6 Hz, 2H), 2.49 (m, 2H), 1.42 (s, 18H).

(c) tert-Butyl 4-(4-((tert-butoxycarbonyl)amino)-3-fluorophenyl)piperidine-1-carboxylate (I54)

A mixture of tert-butyl 4-(4-((tert-butoxycarbonyl) amino)-3-fluorophenyl)-5,6-dihydropyridine-1(2H)-carboxylate (I53) (0.409 g, 1.04 mmol) and 10% Pd/C (0.043 g) in EtOAc (20 mL) was stirred for 16 hours at room temperature under a $H_2$ atmosphere. The mixture was filtered through celite and the filtrate concentrated under reduced pressure to give the title compound (I54) (0.376 g, 92%) as a white foam; $^1$H NMR (400 MHz, $CDCl_3$) δ 7.09 (dd, J=8.1, 8.1 Hz, 1H), 6.95 (m, 2H), 4.25 (m, 2H), 2.79 (dd, J=12.0, 12.0 Hz, 2H), 2.65 (m, 1H), 1.82 (m, 2H), 1.43 (s, 18H).

(d) Methyl 2-(2-(2-(2-((2-fluoro-4-(piperidin-4-yl) phenyl)amino)-5-(trifluoromethyl)pyrimidin-4-yl) ethyl)phenyl)acetate (I58)

To a mixture of tert-butyl 4-(4-((tert-butoxycarbonyl) amino)-3-fluorophenyl)piperidine-1-carboxylate (I57) (0.376 g, 0.954 mmol) and methyl 2-(2-(2-(2-(methylsulfonyl)-5-(trifluoromethyl)pyrimidin-4-yl)ethyl)phenyl)acetate (I15) (0.268 g, 0.667 mmol) in 2,2,2-trifluoroethanol (15 mL) was added TFA (0.8 mL). The resulting mixture was heated under microwave irradiation at 100° C. for 20 minutes then 15 minutes then concentrated under reduced pressure to give a crude sample of the title compound (I58) (0.344 g) which was used without purification.

(e) tert-Butyl 4-(3-fluoro-4-((4-(2-(2-methoxy-2-oxoethyl)phenethyl)-5-(trifluoromethyl)pyrimidin-2-yl)amino)phenyl)piperidine-1-carboxylate (I60)

A mixture of crude methyl 2-(2-(2-(2-((2-fluoro-4-(piperidin-4-yl)phenyl)amino)-5-(trifluoromethyl)pyrimidin-4-yl) ethyl)phenyl)acetate (I59) (0.344 g), $Boc_2O$ (0.214 g, 0.98 mmol) and a catalytic amount of DMAP in DCM (15 mL) was stirred for 20 hours. Triethylamine (0.10 mL, 0.72 mmol) was then added and the mixture stirred for 20 hours at 40° C. Further portions of triethylamine (1.50 mL, 10.8 mmol) and $Boc_2O$ (0.260 g, 1.19 mmol) were added and stirring continued at 40° C. for 4 hours. The mixture was concentrated under reduced pressure and chromatographed on silica gel (0-75% EtOAc/petroleum benzine 40-60° C.) to give the title compound (I60) (0.206 g, 50%) in 79% purity by LCMS, this material was used subsequently without further purification; $^1$H NMR (400 MHz, $CDCl_3$) δ 8.57 (s, 1H), 8.28 (dd, J=8.6, 8.6 Hz, 1H), 7.48 (d, J=2.4 Hz, 1H), 7.22 (m, 4H), 7.00 (m, 2H), 4.25 (m, 2H), 3.75 (s, 2H), 3.68 (s, 3H), 3.11 (m, 4H), 2.81 (m, 2H), 2.64 (m, 1H), 1.84 (m, 2H), 1.62 (dd, J=12.6, 4.5 Hz, 2H), 1.49 (s, 9H); LCMS Method C: rt 7.05 min; m/z 617.2 [M+H]$^+$, 561.1 [(M-t-Bu)+H]$^+$.

(f) tert-Butyl 4-(4-((4-(2-(2-amino-2-oxoethyl)phenethyl)-5-(trifluoromethyl)pyrimidin-2-yl)amino)-3-fluorophenyl)piperidine-1-carboxylate (I61)

To a solution of tert-butyl 4-(3-fluoro-4-((4-(2-(2-methoxy-2-oxoethyl)phenethyl)-5-(trifluoromethyl)pyrimidin-2-yl)amino)phenyl)piperidine-1-carboxylate (I60) (0.206 g) in THF (5 mL) was added aqueous 2 M LiOH (0.500 mL, 1.00 mmol) and water (0.5 mL) and the resulting solution was stirred for 16 hours at room temperature. Aqueous LiOH (1.5 M; 0.5 mL) was added and the reaction stirred for a further 20 hours at room temperature. The mixture was then heated to 50° C. and methanol (1 mL) added before stirring for 20 hours. The volatiles were evaporated under reduced pressure and the residue azeotroped with toluene twice before addition of THF (4 mL), solid lithium hydroxide (0.021 g, 0.87 mmol), water (1 mL) and methanol (1 mL). The resulting mixture was stirred at room temperature for 5 hours and then heated to 50° C. for 16 hours. The volatiles were evaporated under reduced pressure and the residue diluted with water. The aqueous solution was extracted with EtOAc (2×20 mL) before acidifying to a pH of 3 with aqueous HCl. The resulting precipitate was collected as a pellet by centrifugation then dissolved in methanol and concentrated under reduced pressure. The residue was azeotroped with toluene then taken up in DMF (6 mL) to which EDCl (0.080 g, 0.42 mmol), HOBT (0.061 g, 0.45 mmol) and DIPEA (0.29 mL, 1.67 mmol) were added. The mixture was stirred at room temperature for 30 minutes under nitrogen before addition of ammonium carbonate (0.129 g, 1.66 mmol). The resulting mixture was stirred at 30° C. for 20 hours before the volatiles were evaporated under reduced pressure. Water (20 mL) was added and the resulting suspension was extracted with EtOAc (3×20 mL). The combined organic extracts were concentrated under reduced pressure and the residue chromatographed on silica gel (0-100% EtOAc/petroleum benzine 40-60° C. then 70-100% EtOAc/ petroleum benzine 40-60° C.) to give the title compound (I61) (0.049 g, 24%); $^1$H NMR (400 MHz, $d_6$-Acetone) δ 8.71 (s, 1H), 8.60 (s, 1H), 7.98 (dd, J=8.4, 8.4 Hz, 1H), 7.29 (m, 1H), 7.17 (m, 5H), 6.66 (s, 1H), 6.22 (s, 1H), 4.21 (m, 1H), 3.63 (s, 2H), 3.16 (m, 4H), 2.09 (m, 2H), 1.87 (m, 3H), 1.59 (qd, J=12.7, 4.4 Hz, 2H), 1.46 (s, 9H); LCMS Method C: rt 6.46 min; m/z 602.1 [M+H]$^+$, 624.1 [M+Na]$^+$, 546.1 [(M-t-Bu)+H]$^+$, 502.1 [(M-Boc)+H]$^+$.

(g) 2-(2-(2-(2-((2-Fluoro-4-(piperidin-4-yl)phenyl) amino)-5-(trifluoromethyl)pyrimidin-4-yl)ethyl)phenyl)acetamide (I62)

To a solution of tert-butyl 4-(4-((4-(2-(2-amino-2-oxoethyl)phenethyl)-5-(trifluoromethyl)pyrimidin-2-yl)amino)-3-fluorophenyl)piperidine-1-carboxylate (I61) (0.049 g, 0.081 mmol) in THF (3 mL) was added TFA (0.20 mL, 2.6 mmol). The resulting mixture was then stirred at room temperature for 20 hours then 40° C. for 24 hours. The volatiles were removed by evaporation under reduced and DCM (2 mL) and TFA (1.00 mL, 13.1 mmol) were added. After stirring at 30° C. for 18 hours the mixture was concentrated under reduced pressure and the residue azeotroped twice with toluene (10 mL) to give the title compound (I62) (0.037 g, 91%). LCMS Method C: rt 4.84 min; m/z 502.1[M+H]$^+$.

(h) 2-(2-(2-(2-((2-Fluoro-4-(1-methylpiperidin-4-yl) phenyl)amino)-5-(trifluoromethyl)pyrimidin-4-yl) ethyl)phenyl)acetamide (13)

To a solution of 2-(2-(2-(2-((2-fluoro-4-(piperidin-4-yl) phenyl)amino)-5-(trifluoromethyl)pyrimidin-4-yl)ethyl)

phenyl)acetamide (I62) (0.037 g, 0.074 mmol) in anhydrous methanol (3 mL) was added 37% aqueous formaldehyde (0.022 mL, 0.30 mmol) and sodium triacetoxyborohydride (0.081 g, 0.38 mmol) under a nitrogen atmosphere. The resulting mixture was stirred at room temperature for 1 hour. The volatiles were evaporated under reduced pressure and the residue'taken up saturated aqueous NaHCO$_3$ solution (25 mL). The resulting mixture was extracted with EtOAc (2×25 mL) then the combined organic layers were washed with brine (25 mL), dried (phase separation cartridge) and evaporated to dryness under reduced pressure. The residue was purified using silica gel column chromatography (0-50% MeOH/EtOAc with 1% 2 M ethanolic ammonia) to give the title compound (13) (0.020 g, 52%); $^1$H NMR (400 MHz, d$_6$-Acetone+d$_4$-MeOH) δ 8.54 (s, 1H), 7.88 (dd, J=8.5 Hz, 1H), 7.16 (m, 6H), 3.80 (s, 2H), 3.63 (s, 2H), 3.10 (m, 4H), 2.95 (m, 2H), 2.54 (m, 1H), 2.27 (s, 3H), 1.79 (m, 4H). LCMS Method C: rt 4.93 min; m/z 516.1 [M+H]$^+$.

Biological Assays

The activity of compounds of the Invention can be profiled using biochemical and cellular assays.

Primary potency at FAK can be assessed using an Alpha Screen™ technology biochemical assay.

The kinetics of this binding may be further studied using a surface plasmon resonance (SPR) technology assay using a Biacore™ S51 sensor to establish $K_a$, $k_d$ and consequently $K_D$. When off rates from the protein greatly exceed on rates, as may occur for highly potent compounds, $K_D$ gives an accurate measure of protein-ligand binding affinity.

The ability of compounds of the invention to inhibit FAK within cells can be assessed with an ELISA-type assay performed using a Meso Scale Discovery SECTOR Imager 6000 instrument. In this assay the ability of compounds of the invention to inhibit phosphorylation of Y397-FAK is determined.

The effect of compounds of the invention on inhibition of cellular proliferation resulting from non-FAK activity may be assessed using a 2D proliferation assay using a suitable cell line. This gives an indication of off-target activities and potential toxicity arising from them. Therefore, comparing inhibition of phosphorylation of Y397-FAK and 2D proliferation gives a measure of FAK specific mediated effects and also of potential toxicity resulting from off-target activity.

Primary potency at VEGFR3 can be assessed using an Alpha Screen™ technology biochemical assay.

FAK biochemical Alpha Screen™ Assay

A biotin labeled peptide is used as substrate (amino acid sequence: Biotin-Glu-Gly-Pro-Trp-Leu-Glu-Glu-Glu-Glu-Glu-Ala-Tyr-Gly-Trp-Met-Asp-Phe-NH$_2$) SEQ ID NO: 1). FAK enzyme was expressed in insect cells as catalytic domain (amino acids 411-686) N-terminally tagged with six histidine amino acids and a Tobacco Etch Virus (TeV) cleavage sequence. After lysing the cells by sonication, the kinase was purified by Ni-Immobilised Metal Affinity Chromatography, TeV cleavage leaving a N-terminal glycine, and gel filtration. The 15µl assay reactions are run in Greiner brand white 384-well low volume plates. All reactions contained 10 mM HEPES pH 7.4, 25 mM NaCl, 10 mM MgCl$_2$, 0.01% (v/v) Tween-20, 50 µM Na$_3$VO$_4$, 0.01% (w/v) albumin from chicken egg white, 111 nM peptide substrate, 80 µpM ATP, and 4 ng/reaction FAK enzyme, with the enzyme being omitted from negative control reactions. Compounds were added in a volume of 100 nl from dilution series made up in DMSO, positive and negative control reactions receiving the same volume DMSO without compounds. The plates were sealed with adhesive seals and incubated for 90 minutes at 30° C. The reactions were stopped with the detection reagents added at the same time. Product formation was quantified as amplified luminescence between PerkinElmer AlphaScreen™ beads, using Streptavidin-coated donor and anti-phosphotyrosine (P-Tyr-100) acceptor beads. To each reaction, 5 µl containing 10 mM HEPES pH 7.4, 25 mM NaCl, 100 mM EDTA, 0.01% (v/v) Tween-20, and 6.25µg/ml of each bead type were added. Plates were incubated for 6 hours before being read on a PerkinElmer EnVision™ plate reader in HTS Alphascreen™ mode. IC$_{50}$ values were obtained by calculating percent inhibition (%I) for each reaction relative to controls on the same plate (%I=(I-CN)/(CP-CN) where CHN/CP are the averages of the negative/positive reactions, respectively), then fitting the %I data vs. compound concentration [I] to %I=(A+((B−A)/(1+((C/[I])^D)))) where A is the lower asymptote, B is the upper asymptote, C is the IC$_{50}$ value, and D is the slope factor.

Results

| Compound | IC$_{50}$ (nM) |
|---|---|
| 1 | 1.9 |
| 2 | 7.1 |
| 3 | 2.2 |
| 4 | 3.6 |
| 5 | 7.2 |
| 6 | 2.1 |
| 7 | 9.4 |
| 8 | 5.2 |
| 9 | 3.6 |
| 10 | 2.7 |
| 11 | 2.2 |
| 12 | 3.6 |
| 13 | 5.6 |

FAK Biacore™ SPR Assay

Binding parameters of compounds were determined using a Biacore™ S51 sensor. An anti-GST antibody was immobilized onto a CM5 chip by primary amine-coupling in accordance with the manufacturer's recommendations.

In running buffer (0.01 M HEPES pH 7.4, 0.15 M NaCl, 0.005% Surfactant P20, mM MgCl$_2$, and 1% DMSO)N-terminally GST-fused purified FAK enzyme was captured on both spot 1 and 2. Spot 1 was subsequently blocked by loading with 30 nM PF-562,271 at the beginning of each cycle. Concentration series' of the test compounds were injected over the spots at 25° C. The specific binding was calculated as difference between spot 2 and 1 signals followed by solvent correction. Fitting to a one site binding model yielded the kinetic rate constants $k_d$ and $k_a$ and the equilibrium binding constant $K_D=k_d/k_a$.

For compounds with an expected $K_D$<5 nM N-terminally GST-fused purified FAK enzyme was captured on spot 2 of the anti-GST antibody coated chip only. After the injection cycle of a compound the chip surface was regenerated with 10 mM glycine-HCl, pH2.2 before capturing the enzyme again. The binding sensorgrams were analysed as described before.

Results

| Compound | $K_D$ (nM) |
|---|---|
| 1 | 0.29 |
| 2 | 0.74 |
| 3 | 0.21* |
| 4 | 1.5 |
| 6 | 2.9 |
| 8 | 0.81 |
| 9 | 1.5 |

-continued

| Compound | $K_D$ (nM) |
|---|---|
| 10 | 0.79 |
| 11 | 1.7 |

*This result was measured using an extended washing step of 30 minutes.

P397Y-FAK Inhibition MSD Platform Cellular Biomarker Assay

Compounds of the invention may be tested for in vitro activity in the following assay:

96-well plates (cat# MA6000, Meso Scale Discovery) are coated with 30 μL/well of mouse monoclonal FAK antibody [63D5] (cat# ab72140, Abcam) pre-diluted in PBS to a concentration of 1 mg/mL. The plates are sealed with adhesive film and incubated for 16 hours at 4° C. The antibody is then flicked out of the plates and 150 μL of 3% [w/v] Blocker A (cat# R93AA-1, Meso Scale Discovery) is added. The plates are resealed with adhesive film and incubated at room temperature on a shaker set at medium speed for 2 hours. The plates are then washed three times with a solution containing 50 mM Tris-HCl pH 7.5, 0.15M NaCl and 0.02% Tween-20, before cell lysate addition described below.

Cells are split 1:2 into T150 cell culture flasks 2 days prior to compound treatment. On the day prior to compound treatment, 200 μL media containing 20,000 cells is seeded into all wells of white, clear-bottom, TC treated, μclear, 96-well microtitre plates (cat#655098, Greiner Bio-One), and the plates are incubated at 37° C. and 5% $CO_2$ for 36 hours. 1 μL/well of compound is then added from dilution series prepared in DMSO. Negative control wells receive the same volume of DMSO without compounds, and positive control wells receive 2 μM of a control compound in the same volume of DMSO. Cells are treated for 1 hour at 37° C. and 5% $CO_2$. The media/compounds are then flicked off and 55 μL/well of ice-cold complete lysis buffer is added. Complete lysis buffer is prepared by adding 1 tablet PhosSTOP complete phosphatase inhibitor (cat#04906837001, Roche) and 1 tablet Complete, Mini, EDTA-free, protease inhibitor (cat#04693159001, Roche) per 10 mL of incomplete lysis buffer (150 mM NaCl, 20 mM Tris-HCl pH 7.5, 1 mM EDTA, 1 mM EGTA, 1% Triton-X 100). Plates are incubated on ice for 30 minutes, with 30 seconds high speed plate shaking every 5 minutes. 40 μL/well of cell lysate is transferred to the coated, blocked and washed 96-well microtitre plates described above. The 96-well plates are sealed with adhesive film and incubated for 16 hours at 4° C. The plates are then washed three times with a solution containing 50 mM Tris-HCl pH 7.5, 0.15M NaCl and 0.02% Tween-20 and tapped dry. 25 μL/well of detection solution (1% [w/v] Blocker A (cat# R93AA-1, Meso Scale Discovery) in 50 mM Tris-HCl pH 7.5, 0.15M NaCl and 0.02% Tween-20, with 1:600 rabbit polyclonal FAK phospho Y397 antibody (cat# ab39967, Abcam), 1:1000 anti-rabbit sulfo-tag antibody (cat# R32AB-1 Meso Scale Discovery) and 1:40 reconstituted Blocker D-M (cat# D609-0100, Rockland Immunochemicals for Research)) is added, and the plates resealed with adhesive film and incubated for 1 hour at room temperature on a plate shaker set to medium speed. Plates are then washed three times with a solution containing 50 mM Tris-HCl pH 7.5, 0.15M NaCl and 0.02% Tween-20 and tapped dry. 150 μL/well of Read Buffer T+Surfactant (cat# R92TC-1, Meso Scale Discovery) is then added, and pFAK-397 levels quantified using a Meso Scale Discovery SECTOR Imager 6000 instrument.

$IC_{50}$ values are determined by first calculating percent inhibition (% I) for each lysate relative to controls on the same plate (% I=(S−CP)/(CN−CP)) where S is the sample result, CN is the average result of DMSO only treated negative controls, and CP is the average result of 2 μM treated positive controls. % I is plotted against compound concentration [I] and the data fitted using the following equation, % I=(A+((B−A)/(1+((C/[I])^D)))), where A is the lower asymptote, B is the upper asymptote, C is the IC50 value, and D is the slope factor.

Results for MDA-231-LNA Cells

| Compound | $IC_{50}$ (nM) | % response of control at 2 μM |
|---|---|---|
| 1 | 9 | 122 |
| 2 | 12 | 91 |
| 3 | 7 | 102 |
| 4 | 13 | 108 |
| 6 | 264 | 80 |
| 9 | 59 | 112 |
| 10 | 114 | 116 |
| 11 | 16 | 117 |
| 12 | 390 | 77 |
| 13 | 14 | 90 |

2D Cellular Proliferation Assay

Cells are split 1:4 into T75 cell culture flasks two days prior to cell seeding. A variety of cancer cell lines can be utilized in this assay.

On the day of cell seeding 100 μL/well of media containing 1000-5000 cells are added to 96-well microtitre plates (Cat. #655 180, greiner bio-one) except wells G12 and H12 to which 100 μl of media is added. In a second plate, a single row of cells is seeded at the same concentration. This second plate is known as the t=0 plate and is used to calculate the relative cell number prior to addition of test agent. The plates containing cells are incubated for 24 hours at 37° C./5% $CO_2$. 0.5 μL/well of compound is then added from dilution series prepared in DMSO. A compound with known potency is included for each set of plates in order to assess assay performance. Negative control wells receive the same volume of DMSO without compounds. Background signal is determined from wells containing media alone. The t=0 plate is read using addition of a resazurin-based reagent (see below) on the day that other plates have compound added to them. Plates containing cells to which compound has been added are then incubated for 3 days at 37° C. and 5% $CO_2$.

After 3 days of incubation, cell proliferation is quantified by addition of 20 μl/well of a resazurin-based reagent with a typical composition as follows: Resazurin, Sigma# R7017-1G, 0.015% w/v; methylene blue, Sigma# MB-1(25 g), 0.0025% w/v; potassium hexacyanoferrate (III), Sigma# P8131-100G, 0.033 w/v; potassium hexacyanoferrate (II) trihydrate, Sigma# P9387-100G, 0.042% w/v; in PBS buffer. Plates are incubated with resazurin-based reagent for 1-4 hours (37° C., 5% $CO_2$) prior to the determination of fluorescence at, or near ($579_{Ex}/584_{Em}$).

Percentage inhibition of proliferation (% I) for each treated well relative to controls on the same plate is calculated using the equation % I=(S−B)−($T_0$−B)/(CN−B)−($T_0$−B) where S is the sample result B is the background fluorescence, $T_0$ is the t=0 value and CN is the average result of DMSO only treated negative controls. For IC50 determination, % I is plotted against compound concentration [I] and the data fitted using the following equation, % I=(A+((B−A)/(1+((C/[I])^D)))), where A is the lower asymptote, B is the upper asymptote, C is the $IC_{50}$ value, and D is the slope factor.

Results for MDA-231-LNA Cells

| Compound | IC$_{50}$ (μM) |
|---|---|
| 1 | 1.43 |
| 2 | 2.77 |
| 3 | 6.62 |
| 4 | 1.91 |
| 5 | 3.06 |
| 6 | 2.24 |
| 7 | 4.93 |
| 8 | 2.48 |
| 9 | 2.90 |
| 10 | 1.69 |
| 11 | 2.58 |
| 12 | 4.83 |
| 13 | 2.76 |

VEGFR3 Biochemical asay

Compounds of the invention may be tested for in vitro activity in the following assay: A biotin labeled peptide is used as substrate (amino acid sequence: Biotin-Glu-Gly-Pro-Trp-Leu-Glu -Glu-Glu-Glu-Glu-Ala-Tyr-Gly-Trp-Met-Asp-Phe-NH$_2$) (SEQ ID NO: 1). VEGFR3 cytoplasmic domain (amino acids 798-1298) was purchased as N-terminal GST-fusion protein ("the enzyme"). The 15μl assay reactions are run in Greiner brand white 384-well low volume plates. All reactions contained 10 mM HEPES pH 7.4, 10mM MgCl$_2$, 0.01% (v/v) Tween-20, 50μM Na$_3$VO$_4$, 0.01% (w/v) albumin from chicken egg white, 1mM Dithiothreitol, 111 nM peptide substrate, 500μM ATP, and 3.8ng/reaction enzyme, with the enzyme being omitted from negative control reactions. Compounds were added in a volume of 100nl from dilution series prepared in DMSO, positive and negative control reactions receiving the same volume DMSO without compound. The plates were sealed with adhesive seals and incubated for 90 minutes at 30 degree Celsius. The reactions were stopped with the detection reagents added at the same time as follows: Product formation was quantified as amplified luminescence between PerkinElmer AlphaScreen™ beads, using Streptavidin-coated donor and anti-phosphotyrosine (P-Tyr-100) acceptor beads. To each reaction, 5μl containing 10mM HEPES pH 7.4, 25mM NaCI, 100mM EDTA, 0.01% (v/v) Tween-20, and 6.25μg/ml of each bead type were added. Plates were incubated for 6 hours before being read on a PerkinElmer EnVision™ plate reader in HTS Alphascreen™ mode, IC$_{50}$ values were obtained by calculating percent inhibition (%I) for each reaction relative to controls on the same plate (%I=(I-CN)/(CP-CN) where CN/CP are the averages of the negative/positive reactions, respectively), then fitting the %I data vs. compound concentration [I] to %I =(A+((B–A)/(1+((C/[I])^D)))) where A is the lower asymptote, B is the upper asymptote, C is the IC$_{50}$ value, and D is the slope factor.

The above assay was also run in a slightly modified form in some cases (indicated below with *). In these cases, VEGFR3 cytoplasmic domain (amino acids 818-1177, lacking 949-1002 of UniProt accession number P35916) was expressed and purified as N-terminal Hexa-His-fusion protein ("the enzyme"), rather than using the N-terminal GST-fusion protein.

Results

| Compound | IC$_{50}$ (nM) |
|---|---|
| 1 | 275* |
| 2 | 3685* |
| 3 | 538 |
| 5 | 5750* |
| 6 | 10440 |
| 7 | 13260* |
| 8 | 1176 |
| 9 | 1010 |
| 10 | >66000 |
| 11 | 59763 |
| 12 | 240* |
| 13 | 205 |

Combination study

Tolerability

Female Balb/c SCID non-tumour bearing mice were treated with Compound 3 (40 mg/kg p.o. BID) together with twice daily oral and the Src inhibitor dasatinib at 10 mg/kg, 20 mg/kg, or 30 mg/kg (p.o. BID).

Dasatinib was obtained from EuroAsian Chemicals Pvt Ltd, Lower Parel, Mumbai and delivered orally in 0.2 ml of a citrate buffer. Compound 3 was administered consecutively in 0.2 ml I-IPMC-SV (hydroxypropylmethylcellulose suspension vehicle).

Figure 1:
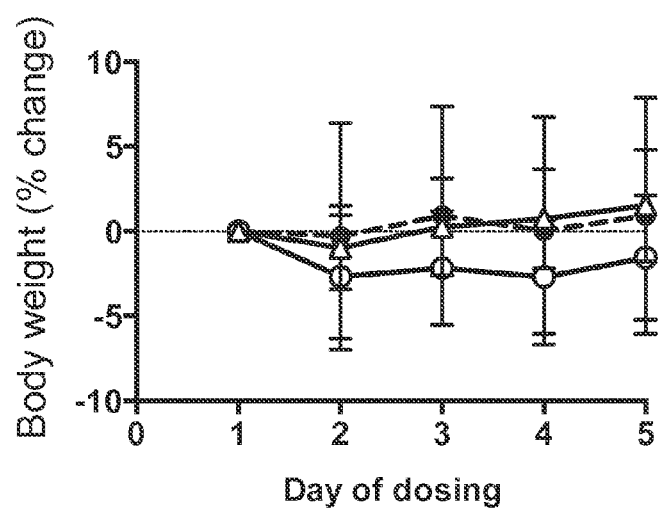
FIG. 1 shows the body weight of mice treated with Compound 3 (40mg/kg p.o. BID) and varying amounts of dasatinib (p.o. BID); 10mg/kg, closed circles; 20mg/kg, open circles; or 30mg/kg, open triangles. All symbols represent the mean ±S.E.M of 4 mice per group.

Body weight was assessed at regular intervals during the experiment as a marker of tolerability, and the results are shown in FIG. 1 (dasatanib at 10 mg/kg, closed circles; 20 mg/kg, open circles; or 30 mg/kg, open triangles. All symbols represent the mean±S.E.M of 4 mice per group.)

This showed that Compound 3 is well tolerated in combination with dasatinib.

Efficacy and Tolerability

Female Balb/c SCID mice bearing IMFP MDA-231-LNA tumours were treated with Compound 3 (40 mg/kg p.o. BID) or dasatinib (30 mg/kg p.o. BID) alone or in combination. Treatment commenced when tumours were palpable (day 9 post cell injection) and continued for the duration of the experiment. The formulations used were the same as those above, with the vehicle (I-IPMC-SV, 0.2 ml), being administered as a control.

Figure 2:
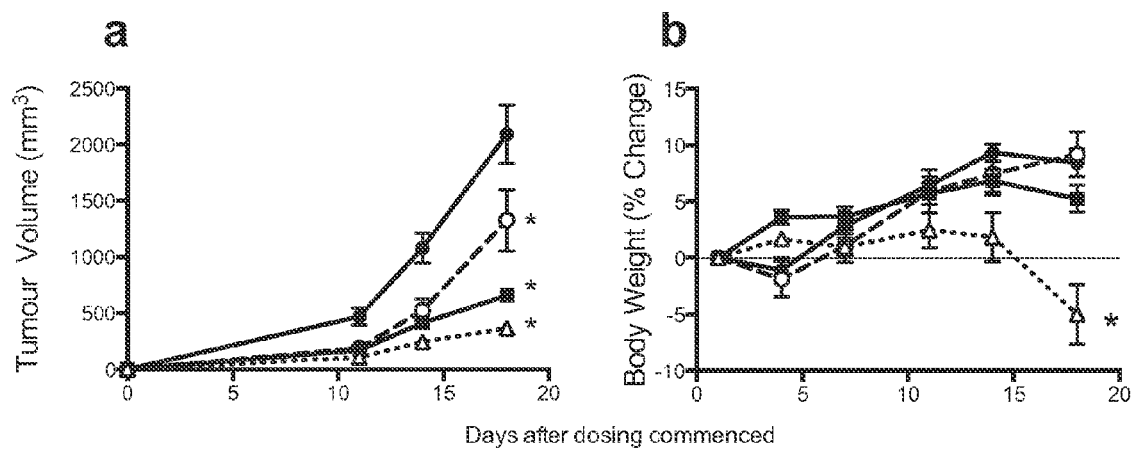
FIG. 2 shows the effect of a vehicle (HPMC-SV), Compound 3 (40mg/kg p.o. BID) and/or dasatinib (30mg/kg p.o. BID) on the (a) tumour volume and (b) body weight of tumour bearing mice following treatment; HPMC-SV (vehicle alone, control)-closed circles: Compound 3 in vehicle open circles; dasatinib in vehicle -closed squares; Compound 3 +dasatinib in vehicle-open triangles. All symbols represent the mean ±S.E.M of 9 mice per group.

The effect of the vehicle and drugs on (a) tumour volume and (b) body weight in female Balb/c SCID mice is shown in FIGS. 2a and 2b respectively (Vehicle—closed circles; compound 3—open circles; dasatinib—closed squares; compound 3+dasatinib—open triangles). All symbols represent the mean±S.E.M of 9 mice per group.

Figure 3:
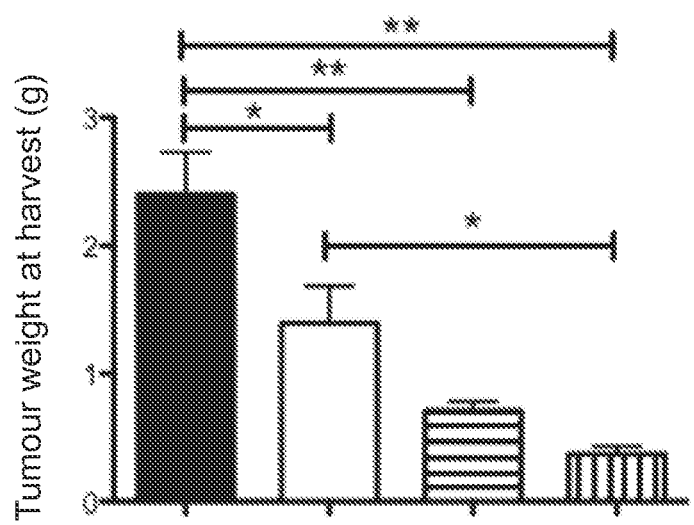
FIG. 3 shows the tumour weight at harvest for relating to the results shown in FIG. 2; HPMC-SV (vehicle, control)-black bar; compound 3-white bar; dasatinib-horizontal striped bar; compound 3 +dasatinib vertical striped bar. All symbols represent the mean ±S.E.M of 9mice per group. *p <0.05, **p <0.01 by one way ANOVA.

The effect of the vehicle and drugs on tumour weight at harvest is shown in FIG. 3. (Vehicle—black bar; compound 3—white bar; dasatinib—horizontal striped bar; compound 3+dasatinib—vertical striped bar). All symbols represent the mean±S.E.M of 9 mice per group. * p<0.05, **p<0.01 by one way ANOVA.

Figure 4:
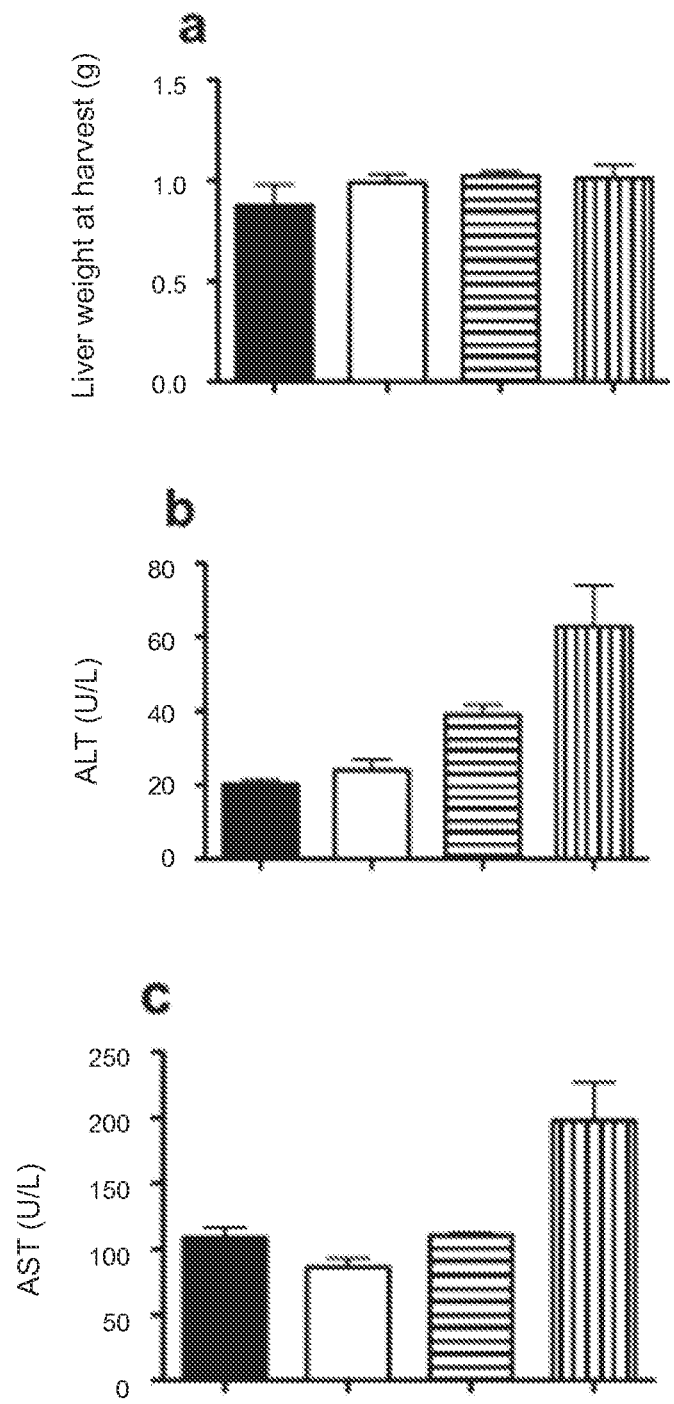
FIG. 4 shows (a) liver weight, (b) plasma alanine aminotransferase (ALT) and (c) plasma aspartate transaminase (AST) levels relating to the results shown in FIG. 2; I-IPMC-SV (vehicle, control)-black bar; compound 3-white bar; dasatinib-horizontal striped bar; compound 3 +dasatinib-vertical striped bar. All symbols represent the mean ±S.E.M of 9mice per group.

As additional markers of potential hepatotoxicity, liver weight at harvest as well as alanine aminotransferase (ALT) and aspartate transaminase (AST) levels were determined in plasma 12 hours after the final dose of drug. The results are shown in FIG. 4, in which FIG. 4a shows liver weight, FIG. 4b shows plasma ALT and FIG. 4c shows plasma AST levels (Vehicle—black bar; compound 3—white bar; dasatinib—horizontal striped bar; compound 3+dasatinib—vertical striped bar). All symbols represent the mean±S.E.M of 9 mice per group.

Compound 3 as a single agent showed a significant effect on MDA-231-LNA primary tumour growth, with a TGI of 42% based on tumour weight. Compound 3 in combination with dasatinib resulted in an 84% TGI which was significantly different to compound 3 alone. The combination of compound 3 and dasatinib was well-tolerated for most of the experiment but mice did begin losing weight towards the end of the experiment.

Combination Study—Tumour Growth Inhibition in the MDA-231-LNA Orthotopic Xenograft Model $2\times10^6$ MDA-231-LNA cells in sterile PBS were injected into the mammary fat pad of female Balb/c SCID mice (6-8 weeks, n=8 per group). Once the tumours were palpable (day 14 post injection of cells) mice were treated once daily with vehicle; hydroxypropylmethylcellulose suspension vehicle (HPMC-SV; 0.2 mL/dose), with Avastin (12.5 mg/kg i.p. twice weekly), Compound 3 p.o. 80 mg/kg QD or a combination of Avastin and compound 3 at the doses described above.

Compound 3 was given as an oral suspension in HPMC-SV (0.2 ml volume) and Avastin (bevacizumab; 12.5 mg/kg; clinical formulation; Roche, Dee Why, New South Wales, Australia) was diluted in phosphate buffered.saline and delivered as an intraperitoneal (i.p.) injection twice weekly in 0.2 ml phosphate buffered saline.

After two weeks of dosing (treatment phase), mice were either harvested (vehicle and compound 3 groups) or swapped to oral vehicle treatment (washout phase, Avastin and combination groups). Mice were weighed routinely during the treatment phase of the experiment and primary tumours were measured using electronic callipers periodically over the duration of the experiment.

When mean tumour volumes in the Avastin group reached ~1500 mm³, all remaining mice were killed by isoflurane anaesthesia and cervical dislocation (at day 42). Blood samples were taken via cardiac puncture and primary tumours were excised and weighed with samples preserved for the determination of vascular density and mature macrophage infiltration.

FIG. 5 shows the (a) tumour volume and (b) body weight of the treated mice (HPMC—closed circles; compound 3—open circles; Avastin—open squares; compound 3+Avastin—open triangles). All symbols represent the mean±SEM of 8 mice per group. * p<0.05 compared to Avastin alone by t-test.

FIG. 6 shows quantitated CD31+ blood vessel staining (left panel) and F4/80+mature macrophage staining (right panel) in MDA-231-LNA primary tumours (Vehicle—black bar; compound 3—white bar; Avastin—vertical striped bar; Avastin+compound 3—horizontal striped bar) All bars represent the mean±S.E.M of n=8 per group. * p<0.05 by one-way ANOVA.

The results show the ability of compound 3 to extend the duration of action of Avastin after cessation of drug therapy, compared to Avastin treatment alone. Tumours were significantly smaller in the combination group on day 37 and day 42, compared to Avastin alone (p<0.05).

Immunohistochemical analysis based on CD31+ staining of the tumours suggests that compound 3 in combination with Avastin may delay revascularization in the primary tumour after cessation of therapy.

The invention claimed is:

1. A compound of the formula (I):

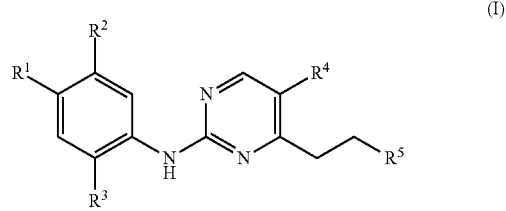

wherein:

$R^1$ is selected from: H and

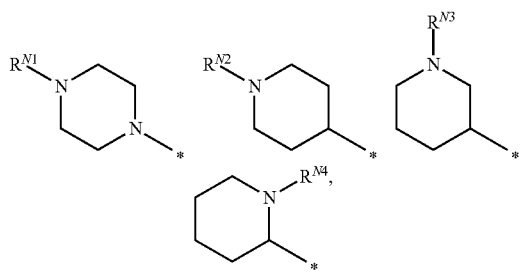

wherein:

$R^{N1}$ is selected from H, $C_{1-3}$ alkyl and $C(=O)Me$;
$R^{N2}$ is selected from H, $C_{1-3}$ alkyl and $C(=O)Me$;
$R^{N3}$ is selected from H, $C_{1-3}$ alkyl and $C(=O)Me$;
$R^{N4}$ is selected from H and $CH_3$;

$R^2$ is selected from H and wherein:

$R^{N5}$ is selected from H, $C_{1-3}$ alkyl and $C(=O)Me$;
$R^{N6}$ is selected from H, $C_{1-3}$ alkyl and $C(=O)Me$;

and wherein only one of $R^1$ and $R^2$ is H;

$R^3$ is selected from $O-C_{1-2}$ alkyl, $C_{1-2}$ alkyl, halo, cyano, where the $C_{1-2}$ alkyl group may be substituted by one or more fluoro groups;

$R^4$ is selected from $CF_3$, halo, $CF_2H$ and CN; and $R^5$ is selected from groups of the following formulae:

($R^{5a}$)

($R^{5b}$)

wherein:

$R^6$ is selected from H, $(CHR^{C1})_{n1}C(O)N(R^{N6})Z^1$ and $(CH_2)_{n2}C(O)OZ^2$; wherein:
  n1 is 1;
  $R^{C1}$ is H or Me;
  $R^{N6}$ is H or $CH_3$;
  $Z^1$ is H, $CH_3$ or $OCH_3$;
  n2 is 1; and
  $Z^2$ is $CH_3$;
and where only one of $R^{N6}$ and $Z^1$ can be $CH_3$, $R^7$ is selected from H, and $(CH_2)_{m1}C(O)N(R^{M1})Y^1$, wherein:
  m1 is 0 or 1;
  $R^{M1}$ is H; and
  $Y^1$ is H, Me or $OCH_3$;
and only one of $R^6$ and $R^7$ is H; and $R^8$ is H or, when $R^7$ is $C(=O)NH_2$, $R^8$ is selected from H and $C_{1-2}$ alkyl.

2. A compound according to claim 1, wherein $R^2$ is H and $R^1$ is:

wherein $R^{N1}$ is $C(=O)Me$.

3. A compound according to claim 1, wherein $R^2$ is H and $R^1$ is:

wherein $R^{N1}$ is H, methyl or ethyl.

4. A compound according to claim 1, wherein $R^2$ is H and $R^1$ is:

wherein $R^{N2}$ is selected from H, methyl and ethyl.

5. A compound according to claim 1, wherein $R^2$ is H and $R^1$ is:

wherein $R^{N3}$ is selected from H and methyl.

6. A compound according to claim 1, wherein $R^2$ is H and $R^1$ is:

wherein $R^{N4}$ is selected from H and methyl.

7. A compound according to claim 1, wherein $R^1$ is H and $R^2$ is:

where $R^{N5}$ is selected from H and methyl.

8. A compound according to claim 1, wherein $R^1$ is H and $R^2$ is:

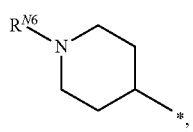

where $R^{N6}$ is selected from H and methyl.

9. A compound according to claim 1, wherein $R^3$ is selected from F, Me, Et, OMe and $OCF_3$.

10. A compound according to claim 1, wherein $R^3$ is OMe.

11. A compound according to claim 1, wherein $R^4$ is selected from $CF_3$, Cl and $CF_2H$.

12. A compound according to claim 11, wherein $R^4$ is $CF_3$.

13. A compound according to claim 1, wherein $R^5$ is a group of the following formula:

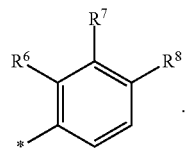

($R^{5a}$)

14. A compound according to claim 13, wherein $R^7$ is H and $R^6$ is selected from $CH_2C(O)NH_2$, $CH_2C(O)NHCH_3$, $CHCH_3C(O)NH_2$ and $CHCH_3C(O)NHCH_3$.

15. A compound according to claim 14, wherein $R^7$ is H and $R^6$ is selected from $CH_2C(O)NH_2$, $CHCH_3C(O)NH_2$ and $CH_2C(O)NHCH_3$.

16. A compound according to claim 15, wherein $R^7$ is H and $R^6$ is selected from $CH_2C(O)NH_2$, and $CHCH_3C(O)NH_2$.

17. A compound according to claim 13, wherein $R^6$ is H and $R^7$ is selected from $C(O)NH_2$, $C(O)NHCH_3$, $CH_2C(O)NH_2$ and $CH_2C(O)NHCH_3$.

18. A compound according to claim 17, wherein $R^6$ is H and $R^7$ is $C(O)NH_2$.

19. A compound according to claim 18, wherein $R^8$ is methyl.

20. A compound according to claim 1, wherein $R^5$ is a group of the following formula:

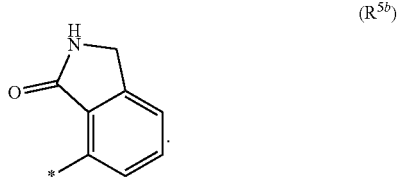 [SMILES: *c1cccc2c1C(=O)NC2]

($R^{5b}$)

21. A composition comprising a compound according to claim 1, and a pharmaceutically acceptable carrier or diluent.

22. 2-(2-(2-(2-((2-Methoxy-4-(1-methylpiperidin-4-yl)phenyl)amino)-5-(trifluo-romethyl)pyrimidin-4-yl)ethyl)phenyl)acetamide.

* * * * *

SEQUENCE LISTING

```
<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Biotin
<220> FEATURE:
<223> OTHER INFORMATION: C-term NH2

<400> SEQUENCE: 1

Glu Gly Pro Trp Leu Glu Glu Glu Glu Ala Tyr Gly Trp Met Asp
1               5                   10                  15

Phe
```